(12) United States Patent  
Nicolau et al.

(10) Patent No.: US 7,648,970 B2  
(45) Date of Patent: Jan. 19, 2010

(54) INOSITOL PYROPHOSPHATES, AND METHODS OF USE THEREOF

(75) Inventors: Yves Claude Nicolau, Newton, MA (US); Jean-Marie Lehn, Strasbourg (FR); Konstantina Fylaktakidou, Thessaloniki (GR); Ruth Greferath, Kehl (DE)

(73) Assignee: Normoxys, Inc., Brighton, MA (US)

( * ) Notice: Subject to any disclaimer, the term of this patent is extended or adjusted under 35 U.S.C. 154(b) by 0 days.

(21) Appl. No.: 11/600,685

(22) Filed: Nov. 16, 2006

(65) Prior Publication Data

US 2007/0207986 A1 Sep. 6, 2007

Related U.S. Application Data

(60) Continuation of application No. 11/328,313, filed on Jan. 9, 2006, which is a division of application No. 10/425,569, filed on Apr. 29, 2003, now Pat. No. 7,084,115.

(60) Provisional application No. 60/376,383, filed on Apr. 29, 2002, provisional application No. 60/388,851, filed on Jun. 14, 2002, provisional application No. 60/395,749, filed on Jul. 12, 2002, provisional application No. 60/424,573, filed on Nov. 7, 2002.

(51) Int. Cl.  
*A61K 31/663* (2006.01)  
*C07F 9/02* (2006.01)

(52) U.S. Cl. .......................................... 514/102; 558/77

(58) Field of Classification Search ....................... None  
See application file for complete search history.

(56) References Cited

U.S. PATENT DOCUMENTS

| | | | |
|---|---|---|---|
| 4,192,869 A | 3/1980 | Nicolau et al. |
| 4,321,259 A | 3/1982 | Nicolau et al. |
| 4,404,150 A | 9/1983 | Tsunekawa et al. |
| 4,473,496 A | 9/1984 | Scannon |
| 4,478,824 A | 10/1984 | Franco et al. |
| 4,650,786 A | 3/1987 | Wong |
| 4,652,449 A | 3/1987 | Ropars et al. |
| 4,699,926 A | 10/1987 | Abraham et al. |
| 4,710,488 A | 12/1987 | Wong |
| 4,731,381 A | 3/1988 | Abraham et al. |
| 4,731,473 A | 3/1988 | Abraham et al. |
| 4,735,936 A | 4/1988 | Sirén |
| 4,751,244 A | 6/1988 | Abraham et al. |
| 4,752,586 A | 6/1988 | Ropars et al. |
| 4,777,134 A | 10/1988 | Siren |
| 4,794,014 A | 12/1988 | Siren |
| 4,797,390 A | 1/1989 | Siren |
| 4,826,675 A | 5/1989 | Gaffar et al. |
| 4,847,082 A | 7/1989 | Sabin |
| 4,851,560 A | 7/1989 | Siren |
| 4,873,355 A | 10/1989 | Hobbs et al. |
| 4,874,690 A | 10/1989 | Goodrich, Jr. et al. |
| 4,887,995 A | 12/1989 | Abraham et al. |
| 4,924,023 A | 5/1990 | Hobbs et al. |
| 4,931,276 A | 6/1990 | Franco et al. |
| 4,952,717 A | 8/1990 | Ozaki et al. |
| 5,003,098 A | 3/1991 | Siren et al. |
| 5,015,634 A | 5/1991 | Siren |
| 5,019,566 A | 5/1991 | Siren |
| 5,023,248 A | 6/1991 | Siren |
| 5,043,261 A | 8/1991 | Goodrich et al. |
| 5,051,411 A | 9/1991 | Siren |
| 5,057,507 A | 10/1991 | Siren |
| 5,082,833 A | 1/1992 | Shamsuddin |
| 5,091,549 A | 2/1992 | Ozaki et al. |
| 5,135,923 A | 8/1992 | Siren |
| 5,151,539 A | 9/1992 | Bright et al. |
| 5,210,263 A | 5/1993 | Kozikowski et al. |
| 5,252,707 A | 10/1993 | Ozaki et al. |
| 5,260,287 A | 11/1993 | Barreto et al. |
| 5,260,472 A | 11/1993 | Chen |
| 5,264,605 A | 11/1993 | Ozaki et al. |
| 5,274,161 A | 12/1993 | Siren et al. |
| 5,292,913 A | 3/1994 | Ozaki et al. |
| 5,295,944 A | 3/1994 | Teicher et al. |
| 5,296,466 A | 3/1994 | Kilbourn et al. |
| 5,330,979 A | 7/1994 | Siren et al. |
| 5,344,393 A | 9/1994 | Roth et al. |
| 5,407,924 A | 4/1995 | Siren |
| 5,428,007 A | 6/1995 | Fischer et al. |
| 5,451,205 A | 9/1995 | Roth et al. |
| 5,545,632 A | 8/1996 | Siren |
| 5,612,207 A | 3/1997 | Nicolau et al. |
| 5,626,884 A | 5/1997 | Lockett |
| 5,720,921 A | 2/1998 | Meserol |
| 5,827,837 A | 10/1998 | Bevilacqua et al. |
| 5,846,957 A | 12/1998 | Siren |
| 5,866,548 A | 2/1999 | Tsien et al. |

(Continued)

FOREIGN PATENT DOCUMENTS

EP 0 392 697 A2 10/1990

(Continued)

OTHER PUBLICATIONS

Vincent et al. Bioorganic & Medicinal Chemistry Letters vol. 10 (9) pp. 2825-2834, (2002).*

(Continued)

*Primary Examiner*—Kamal A Saeed  
(74) *Attorney, Agent, or Firm*—King & Spalding

(57) ABSTRACT

The present invention comprises compounds, compositions thereof, and methods capable of delivering modified inositol hexaphosphate (IHP) comprising an internal pyrophosphate ring to the cytoplasm of mammalian cells. In certain embodiments, the present invention relates to compounds, compositions thereof, and methods that enhance the ability of mammalian red blood cells to deliver oxygen, by delivering IHP to the cytoplasm of the red blood cells.

13 Claims, 15 Drawing Sheets

U.S. PATENT DOCUMENTS

| | | | |
|---|---|---|---|
| 5,866,557 | A | 2/1999 | Persson et al. |
| 5,880,099 | A | 3/1999 | Traynor-Kaplan et al. |
| 5,977,078 | A | 11/1999 | Traynor-Kaplan et al. |
| 6,004,938 | A | 12/1999 | Frick et al. |
| 6,074,605 | A | 6/2000 | Meserol et al. |
| 6,096,916 | A | 8/2000 | Aneja |
| 6,187,335 | B1 | 2/2001 | Brey et al. |
| 6,610,702 | B2 | 8/2003 | Lehn et al. |
| 7,084,115 | B2 | 8/2006 | Nicolau et al. |
| 7,084,126 | B1 | 8/2006 | Frey, II et al. |
| 2002/0028786 | A1 | 3/2002 | Frey, II et al. |
| 2002/0142995 | A1 | 10/2002 | Nicolau et al. |
| 2002/0173494 | A1 | 11/2002 | Lehn et al. |
| 2003/0017150 | A1 | 1/2003 | Torphy |
| 2003/0147937 | A1 | 8/2003 | Schwarz |
| 2004/0014642 | A1 | 1/2004 | Nicolau et al. |
| 2004/0072801 | A1 | 4/2004 | Nicolau et al. |
| 2004/0147487 | A1 | 7/2004 | Traylor-Kaplan et al. |
| 2005/0020542 | A1 | 1/2005 | Traynor-Kaplan et al. |
| 2005/0227946 | A1 | 10/2005 | Siren |
| 2005/0250743 | A1 | 11/2005 | Lehn et al. |
| 2005/0272642 | A1 | 12/2005 | Frey, II et al. |
| 2006/0009413 | A1 | 1/2006 | Frey, II et al. |
| 2006/0014716 | A1 | 1/2006 | Frey, II et al. |
| 2006/0030542 | A1 | 2/2006 | Frey, II et al. |

FOREIGN PATENT DOCUMENTS

| | | |
|---|---|---|
| EP | 0 508 488 B1 | 10/1992 |
| JP | 52-107239 | 9/1977 |
| JP | 1-175989 | 7/1989 |
| WO | WO 87/05598 A1 | 9/1987 |
| WO | WO 92/20369 | 11/1992 |
| WO | WO 94/21117 A1 | 9/1994 |
| WO | WO 95/03068 | 2/1995 |
| WO | WO 95/05830 A1 | 3/1995 |
| WO | WO 96/32136 | 10/1996 |
| WO | WO 01/13933 | 3/2001 |
| WO | WO 01/15738 | 3/2001 |
| WO | WO 01/24830 A2 | 4/2001 |
| WO | WO 01/82932 A2 | 11/2001 |
| WO | WO 02/10177 A1 | 2/2002 |
| WO | WO 03/092700 A1 | 11/2003 |

OTHER PUBLICATIONS

Johnson L. Canadian Journal of Chemistry, 47, 63 pp. 63-73 (1969).*
EntreMed Annual Report, *EDGAR Online*, pp. 1-40, Mar. 3, 2000.
Adachi et al., Nucleation-Controlled Aggregation of Deoxyhemoglobins—Effect of Organic Phosphates on the Kinetics of Aggregation of Deoxyhemoglobin S in Concentrated Phosphate Buffer, *Biochimica et Biophysica Acta*, vol./Iss: 624, pp. 372-377, Aug. 21, 1980.
Amorino et al., Enhancement of Tumor Oxygenation and Radiation Response by the Allosteric Effector of Hemoglobin, RSR13, *Radiation Research*, vol./Iss: 156, pp. 1, Oct. 12, 2000.
Arnone, A., X-ray Diffraction Study of Binding of 2,3-Diphosphoglycerate to Human Deoxyhaemoglobin, *Nature*, vol./Iss: 237 (5350), pp. 146-149, May 12, 1972.
Benesch et al., The Effect of Organic Phosphates from the Human Erythrocyte on the Allosteric Properties of Hemoglobin, *Biochemical and Biophysical Research Communications*, vol./Iss: 26 (2), pp. 162-167, Jan. 23, 1967.
Benesch et al., Intracellular Organic Phosphates as Regulators of Oxygen Release by Haemoglobin, *Nature*, vol./Iss: 221, pp. 618-622, Feb. 15, 1969.
Cosgrove, D.J., The Phosphorylation of *epi*-Inositol and *muco*-Inositol with Polyphosphoric Acid, *Carbohydrate Research*, vol./Iss: 40, pp. 380-384, Jan. 1, 1975.
Desai et al., The Preparation, Resolution, and Phosphorylation of Some Benzyl Ethers of *myo*-Inositol: Intermediates for the Synthesis of *myo*-Inositol Phosphates of the Phosphotidylinositol Cycle, *Carbohydrate Research*, vol./Iss: 225, pp. 209-228, Mar. 1, 1992.
Dinkel et al., Membrane-Permeant 3-OH-Phosphorylated Phosphoinositide Derivatives, *Angewandte Chemie Intenational Edition*, vol./Iss: 40 (16), pp. 3004-3008, Aug. 17, 2001.
Gersonde et al., Modification of the Oxygen Affinity of Intracellular Haemoglobin by Incorporation of Polyphosphates into Intact Red Blood Cells and Enhanced $O_2$ Release in theCapillary System, *Bibliotheca Haematologica*, vol./Iss: 46, pp. 81-92, Sep. 1, 1980.
Huang et al., Identification and Purification of Diphosphoinositol Pentakisphosphate Kinase, Which Synthesizes the Inositol Pyrophosphate Bis(diphospho)inositol Tetrakisphosphate, *Biochemistry*, vol./Iss: 37, pp. 14998-15004, Jan. 1, 1998.
Johnson, L.F., Structure of "Phytic Acids", *Canadian Journal of Chemistry*, vol./Iss: 47, pp. 63-73, Jan. 1, 1969.
Kilgore et al., RSR13, a Synthetic Allosteric Modifier of Hemoglobin, Improves Myocardial Recovery Following Hypothermic Cardiopulmonary Bypass, *Circulation*, vol./Iss: 100:II-351, pp. 1-15, Jan. 1, 1999.
Lee et al., Synthesis of Mono and Unsymmetrical Bis Ortho Esters of scyllo-Inositol, *Journal of Organic Chemistry*, vol./Iss: 50, pp. 4402-4404, Jan. 1, 1985.
Lu et al., Molecular Interactions of Endogenous D-*myo*-Inositol Phosphates with the Intracellular D-*myo*-Inositol 1,4,5-Trisphosphate Recognition Site, *Biochemistry*, vol./Iss: 33, pp. 11586-11597, Jan. 1, 1994.
Luo et al., Inositol Pyrophosphates are Required for DNA Hyper-recombination in Protein Kinase C1 Mutant Yeast, *Biochemistry*, vol./Iss: 41, pp. 2509-2515, Jan. 1, 2002.
Menniti et al., Turnover of Inositol Polyphosphate Pyrophosphates in Pancreatoma Cells, *The Journal of Biological Chemistry*, vol./Iss: 68 (6), pp. 3850-3856, Jan. 1, 1993.
Montchamp et al., Butane, 2,3-Bisacetal Protection of Vicinal Diequatorial Diols, *Journal of Organic Chemistry*, vol./Iss: 61, pp. 3897-3899, Jan. 1, 1996.
Nicolau et al., Incorporation of Allosteric Effectors of Hemoglobin in Red Blood Cells. Physiologic Effects, *Bibliotheca Haematologica*, vol./Iss: 51, pp. 92-107, Jan. 1, 1985.
Noble et al., Total Synthesis of Myo-Inositol-1-Phosphate-4,5-Pyrophosphate, a Novel Second Messenger Analogue, via Myo-Inositol-1-Phosphate-4,5-Bisphosphorthioate, *Bioorganic & Medicinal Chemistry Letters*, vol./Iss: 2 (5), pp. 471-476, Jan. 1, 1992.
Oshiro et al., Regulation of the *DPPI*-encoded Diacyglycerol Pyrophosphate (DGPP) Phosphatase by Inositol and Growth Phase, *The Journal of Biological Chemistry*, vol./Iss: 275 (52), pp. 40887-40896, Dec. 29, 2000.
Pagel et al., RSR13, a Synthetic Modifier of Hemoglobin-Oxygen Affinity, Enhances the Recovery of Stunned Myocardium in Anesthetized Dogs (Applicants do not have complete copy), *Pharmacology*, vol./Iss: 285 (1), pp. 1-8, Apr. 1, 1998.
Poillon et al., Deoxygenated Sickle Hemoglobin. Modulation of its Solubility by 2,3-diphosphoglycerate and other Allosteric Polyanions (Appliants do not have complete copy), *The Journal of Biological Chemistry*, vol./Iss: 260 (26), pp. 13897-13900, Nov. 15, 1985.
Ruckpaul et al., Interaction of Hemoglobin with Ions Allosteric Effects of the Binding of Anions, *Biochimica et Biophysica Acta*, vol./Iss: 236, pp. 211-221, Jan. 1, 1971.
Saiardi et al., Mammalian Inositol Polyphosphate Multikinase Synthesizes Inositol 1,4,5-Trisphosphate and an Inositol Pyrophosphate, *Proceedings of the National Academy of Sciences of the USA*, vol./Iss: 98 (5), pp. 2306-2311, Feb. 27, 2001.
Teicher et al., Allosteric Effectors of Hemoglobin as Modulators of Chemotherapy and Radiation Therapy in Vitro and in Vivo (Applicants do not have complete copy), *Cancer Chemotherapy Pharmacology*, vol./Iss: 42 (1), pp. 24-30, Jan. 1, 1998.
Teisseire et al., Physiological Effects of High-$P_{50}$ Erythrocyte Transfusion on Piglets, *Journal of Applied Physiology*, vol./Iss: 58 (6), pp. 1810-1817, Jun. 1, 1985.
Teisseire et al., Long-Term Physiological Effects of Enhanced $O_2$ Release by Inositol Hexaphosphate-Loaded Erythrocytes, *Proceed-* ings of the National Academy of Sciences of the USA, vol./Iss: 84 (19), pp. 6894-6898, Oct. 1, 1987.

Vacca et al., The Total Synthesis of myo-Inositol Polyphosphates, *Tetrahedron*, vol./Iss: 45 (17), pp. 5679-5702, Jan. 1, 1989.

Vacca et al., Chapter 5: Synthesis of myo-Inositol Polyphosphates, *ACS Symposium Series*, pp. 67-85, Aug. 26, 1990.

Ye et al., Inhibition of Clathrin Assembly by High Affinity Binding of Specific Inositol Polyphosphates to the Synapse-specific Clathrin Assembly Protein AP-3, *The Journal of Biological Chemistry*, vol./Iss: 270 (4), pp. 1564-1568, Jan. 1, 1995.

Gutman et al., Failure of Thalidomide to Inhibit Tumor Growth and Angiogenesis in Vivo, *Anticancer Research*, vol./Iss: 16, pp. 3673-3678, Jan. 1, 1996.

Hockel et al., Tumor Hypoxia: Definitions and Current Clinical, Biologic, and Molecular Aspects, *Journal of the National Cancer Institute*, vol./Iss: 93(4), pp. 266-276, Feb. 21, 2001.

Ishii et al., Decreased Medial Temporal Oxygen Metabolism in Alzheimer's Disease Shown by PET, *The Journal of Nuclear Medicine*, vol./Iss: 37(7), pp. 1159-1165, Jul. 1, 1996.

Thomas et al., Current Role of Thalidomide in Cancer Treatment, *Current Opinions in Oncology*, vol./Iss: 12, pp. 564-573, Jan. 1, 2000.

PCT Search Report PCT/US08/05603, Jul. 16, 2008.

PCT Search Report PCT/US07/08112, Sep. 24, 2008.

PCT Search Report PCT/US07/26495, Aug. 1, 2008.

PCT Search Report PCT/US2008/006837, Aug. 15, 2008.

U.S. Appl. No. 11/328,313—Office Action, *USPTO*, pp. 1-8, Dec. 10, 2008.

U.S. Appl. No. 11/600,685- Office Action, *USPTO*, pp. 1-7, Nov. 28, 2008.

U.S. Appl. No. 11/384,012—Final Office Action, *USPTO*, pp. 1-5, Nov. 17, 2008.

U.S. Appl. No. 11/384,012—Office Action, *USPTO*, pp. 1-6, Apr. 29, 2008.

U.S. Appl. No. 11/175,979—Office Action, *USPTO*, pp. 1-10, Jul. 22, 2008.

U.S. Appl. No. 11/384,012—Office Action, *USPTO*, pp. 1-7, Jul. 8, 2009.

U.S. Appl. No. 11/396,338—Final Office Action, *USPTO*, pp. 1-7, Aug. 20, 2008.

* cited by examiner

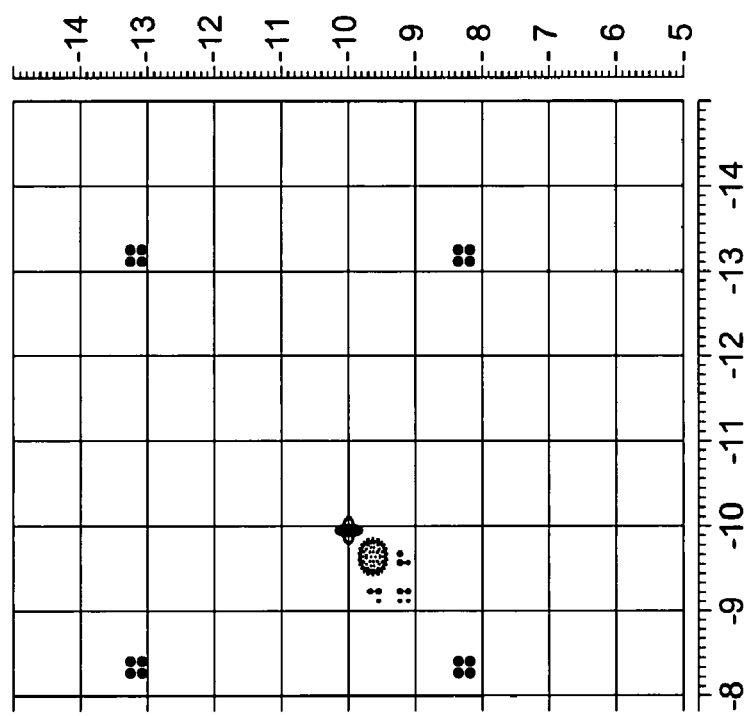
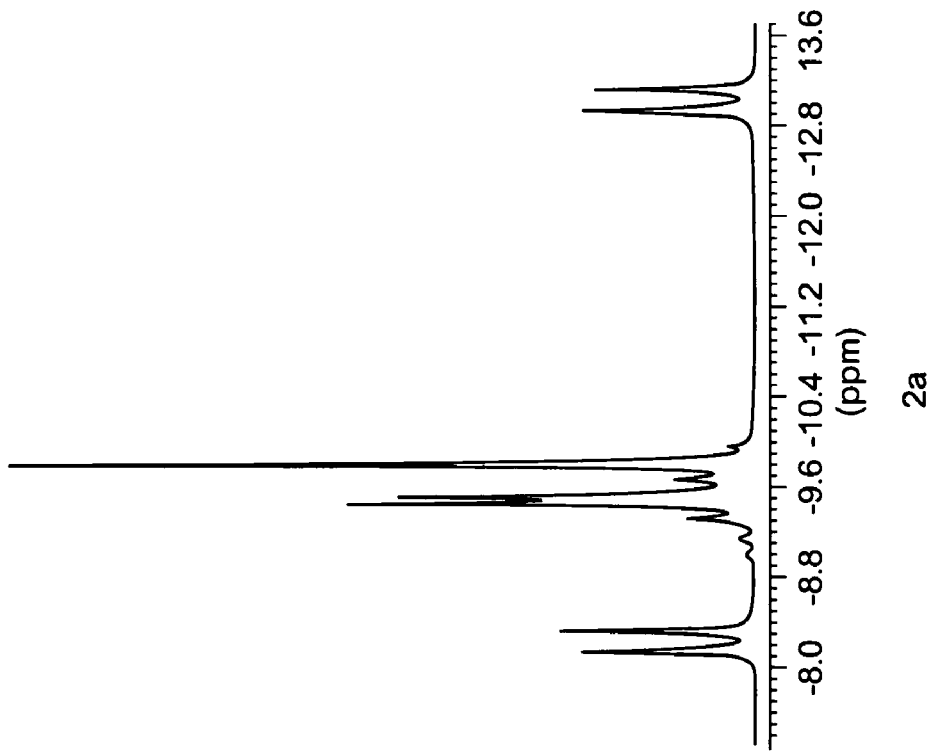
Figure 8

Figure 10 - General Scheme for the synthesis of phytic acid derivatives
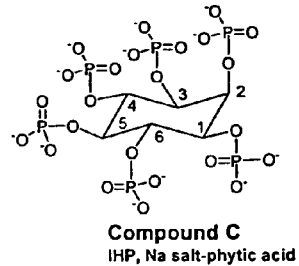
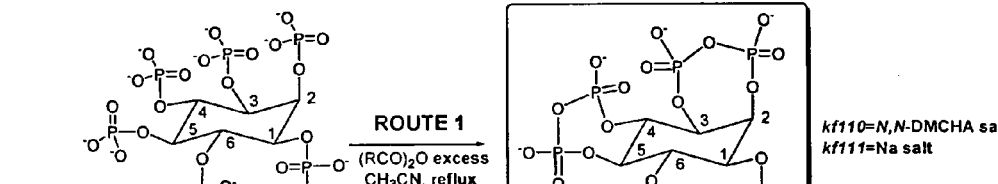
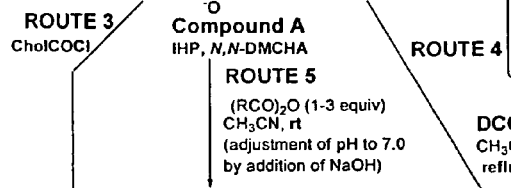
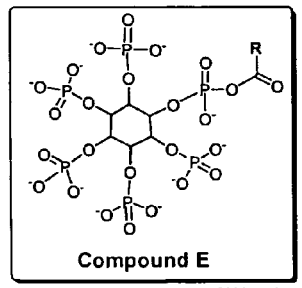

INOSITOL PYROPHOSPHATES, AND METHODS OF USE THEREOF

RELATED APPLICATION INFORMATION

This application is a continuation of U.S. patent application Ser. No. 11/328,313, filed Jan. 9, 2006, which is a divisional of U.S. patent application Ser. No. 10/425,569, filed Apr. 29, 2003, now U.S. Pat. No. 7,084,115, which application claims the benefit of U.S. Provisional Application No. 60/376,383, filed Apr. 29, 2002, U.S. Provisional Application No. 60/388,851, filed Jun. 14, 2002, U.S. Provisional Application No. 60/395,749, filed Jul. 12, 2002, and U.S. Provisional Application No. 60/424,573, filed Nov. 7, 2002, each of which are hereby incorporated by reference.

BACKGROUND OF THE INVENTION

I. Ischemia

Ischemic insult, i.e., the localized deficiency of oxygen to an organ or skeletal tissue, is a common and significant problem in many clinical conditions. The problem is especially acute in organ transplant operations in which a harvested organ is removed from a body, isolated from a blood source, and thereby deprived of oxygen and nutrients for an extended period of time. Ischemic insult also occurs in certain clinical conditions, such as sickle cell anemia and septic shock, which may result from hypotension or organ dysfunction. Depending on the duration of the insult, the ischemia can disturb cellular metabolism and ion gradients, and ultimately cause irreversible cellular injury and death.

Arguably, heart attacks and stroke are the most widely recognized example of the damage resulting from ischemia. Myocardial ischemia is a condition wherein there is insufficient blood supply to the myocardium (the muscles of the heart) to meet its demand for oxygen. The ultimate result of persistent myocardial ischemia is necrosis or death of a portion of cardiac muscle tissue, known as a myocardial infarct, commonly known as a heart attack.

Insufficient blood supply to the myocardium is generally due to an obstruction or thrombus in an artery supplying blood to the myocardium. Another cause can be atrial fibrillation, wherein the increased heart rate associated with atrial fibrillation increases the work, and hence the blood demand of the myocardium, while the atrial fibrillation at the same time reduces the blood supply.

Whereas stroke is defined as a sudden impairment of body functions caused by a disruption in the supply of blood to the brain. For instance, a stroke occurs when blood supply to the brain is interrupted for any reason, including hemorrhage, low blood pressure, clogging by atherosclerotic plaque, a blood clot, or any particle. Because of the blockage or rupture, part of the brain fails to get the supply of blood and oxygen that it requires. Brain tissue that receives an inadequate supply of blood is said to be ischemic. Deprived of oxygen and nutrients, nerve cells and other cell types within the brain begin to fail, creating an infarct (an area of cell death, or necrosis). As the neurons fail and die, the part of the body controlled by those neurons can no longer function. The devastating effects of ischemia are often permanent because brain tissue has very limited repair capabilities and lost neurons are typically not regenerated.

Cerebral ischemia may be incomplete (blood flow is reduced but not entirely cut off), complete (total loss of tissue perfusion), transient or permanent. If ischemia is incomplete and persists for no more than ten to fifteen minutes, neural death may not occur. More prolonged or complete ischemia results in infarction. Depending on the site and extent of the infarction, mild to severe neurological disability or death will follow.

To a modest extent, the brain is protected against cerebral ischemia by compensatory mechanisms, including collateral circulation (overlapping local blood supplies), and arteriolar auto-regulation (local smooth muscle control of blood flow in the smallest arterial channels). If compensatory mechanisms operate efficiently, slightly diminished cerebral blood flow produces neither tissue ischemia nor abnormal signs and symptoms. Usually, such mechanisms must act within minutes to restore blood flow if permanent infarction damage is to be avoided or reduced. Arteriolar auto-regulation works by shunting blood from noncritical regions to infarct zones.

Even in the face of systemic hypotension, auto-regulation may be sufficient to adjust the circulation and thereby preserve the vitality and function of brain or heart tissue. Alternatively, ischemia may be sufficiently prolonged and compensatory mechanisms sufficiently inadequate that a catastrophic stroke or heart attack results.

Ischemia is also associated with various clinical conditions, such as septic shock. Septic shock as a result of hypotension and organ dysfunction in response to infectious sepsis is a major cause of death. The manifestations of sepsis include those related to the systemic response to infection (tachycardia, tachypnea alterations in temperature and leukocytosis) and those related to organ-system dysfunction (cardiovascular, respiratory, renal, hepatic and hematologic abnormalities). Furthermore, the lipopolysaccharide (LPS) of gram-negative bacteria is considered to be the most important exogenous mediator of acute inflammatory response to septic shock. The LPS or endotoxin released from the outer membrane of gram-negative bacteria results in the release of cytokines and other cellular mediators, including tumor necrosis factor alpha (TNF alpha), interleukin-1 (Il-1), interleukin-6 (Il-6) and thromboxane A2. Extreme levels of these mediators are known to trigger many pathological events, including fever, shock, and intravascular coagulation, leading to ischemia and organ failure.

II. Hemoglobin

Hemoglobin is a tetrameric protein which delivers oxygen via an allosteric mechanism. Oxygen binds to the four hemes of the hemoglobin molecule. Each heme contains porphyrin and iron in the ferrous state. The ferrous iron-oxygen bond is readily reversible. Binding of the first oxygen to a heme releases much greater energy than binding of the second oxygen molecule, binding of the third oxygen releases even less energy, and binding of the fourth oxygen releases the least energy.

In blood, hemoglobin is in equilibrium between two allosteric structures. In the "T" (for tense) state, hemoglobin is deoxygenated. In the "R" (for relaxed) state, hemoglobin is oxygenated. An oxygen equilibrium curve can be scanned to observe the affinity and degree of cooperativity (allosteric action) of hemoglobin. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined (i.e., this is the pressure in mm Hg when the scanned hemoglobin sample is 50% saturated with oxygen). Under physiological conditions (i.e., 37° C., pH=7.4, and partial carbon dioxide pressure of 40 mm Hg), the $P_{50}$ value for normal adult hemoglobin (HbA) is around 26.5 mm Hg. If a lower than normal $P_{50}$ value is obtained for the hemoglobin being tested, the scanned curve is considered to be "left-shifted" and the presence of high oxygen-affinity hemoglobin is indicated. Conversely, if a higher than normal $P_{50}$ value is obtained for the hemoglobin being tested, the scanned curve is considered to be "right-shifted", indicating the presence of low oxygen-affinity hemoglobin.

It has been proposed that influencing the allosteric equilibrium of hemoglobin is a viable avenue of attack for treating diseases. The conversion of hemoglobin to a high affinity state is generally regarded to be beneficial in resolving problems with (deoxy)hemoglobin-S (i.e., sickle cell anemia). The conversion of hemoglobin to a low affinity state is believed to have general utility in a variety of disease states where tissues suffer from low oxygen tension, such as ischemia and radio sensitization of tumors. Several synthetic compounds have been identified which have utility in the allosteric regulation of hemoglobin and other proteins. For example, several new compounds and methods for treating sickle cell anemia which involve the allosteric regulation of hemoglobin are reported in U.S. Pat. No. 4,699,926 to Abraham et al., U.S. Pat. No. 4,731,381 to Abraham et al., U.S. Pat. No. 4,731,473 to Abraham et al., U.S. Pat. No. 4,751,244 to Abraham et al., and U.S. Pat. No. 4,887,995 to Abraham et al. Furthermore, in both Perutz, "Mechanisms of Cooperativity and allosteric Regulation in Proteins", *Quarterly Reviews of Biophysics* 22, 2 (1989), pp. 163-164, and Lalezari et al., "LR16, a compound with potent effects on the oxygen affinity of hemoglobin, on blood cholesterol, and on low density lipoprotein", *Proc. Natl. Acad. Sci., USA* 85 (1988), pp. 6117-6121, compounds which are effective allosteric hemoglobin modifiers are discussed. In addition, Perutz et al. has shown that a known antihyperlipoproteinemia drug, bezafibrate, is capable of lowering the affinity of hemoglobin for oxygen (See "Bezafibrate lowers oxygen affinity of hemoglobin", *Lancet* 1983, 881).

Human normal adult hemoglobin ("HbA") is a tetrameric protein comprising two alpha chains having 141 amino acid residues each and two beta chains having 146 amino acid residues each, and also bearing prosthetic groups known as hemes. The erythrocytes help maintain hemoglobin in its reduced, functional form. The heme-iron atom is susceptible to oxidation, but may be reduced again by one of two systems within the erythrocyte, the cytochrome b5, and glutathione reduction systems.

Hemoglobin is able to alter its oxygen affinity, thereby increasing the efficiency of oxygen transport in the body due to its dependence on 2,3-DPG, an allosteric regulator. 2,3-DPG is present within erythrocytes at a concentration that facilitates hemoglobin to release bound oxygen to tissues. Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two alpha- and two beta-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

It is known that hemoglobin specifically binds small polyanionic molecules, especially 2,3-diphosphoglycerate (DPG) and adenosine triphosphate (ATP), present in the mammalian red cell (Benesch and Benesch, *Nature*, 221, p. 618, 1969). This binding site is located at the centre of the tetrameric structure of hemoglobin (Arnone, A., *Nature*, 237, p. 146, 1972). The binding of these polyanionic molecules is important in regulating the oxygen-binding affinity of hemoglobin since it allosterically affects the conformation of hemoglobin leading to a decrease in oxygen affinity (Benesch and Benesch, *Biochem. Biophys. Res. Comm.*, 26, p. 162, 1967). Conversely, the binding of oxygen allosterically reduces the affinity of hemoglobin for the polyanion. (Oxy) hemoglobin therefore binds DPG and ATP weakly. This is shown, for example, by studies of spin-labeled ATP binding to oxy- and deoxyhemoglobin as described by Ogata and McConnell (*Ann. N.Y. Acad. Sc.*, 222, p. 56, 1973). In order to exploit the polyanion-binding specificity of hemoglobin, or indeed to perform any adjustment of its oxygen-binding affinity by chemically modifying the polyanion binding site, it has been necessary in the prior art that hemoglobin be deoxygenated. However, hemoglobin as it exists in solutions, or mixtures exposed to air, is in its oxy state, i.e., (oxy)hemoglobin. In fact it is difficult to maintain hemoglobin solutions in the deoxy state, (deoxy)hemoglobin, throughout a chromatographic procedure. Because of these difficulties, the technique of affinity chromatography has not been used in the prior art to purify hemoglobin.

Hemoglobin has also been administered as a pretreatment to patients receiving chemotherapeutic agents or radiation for the treatment of tumors (U.S. Pat. No. 5,428,007; WO 92/20368; WO 92/20369), for prophylaxis or treatment of systemic hypotension or septic shock induced by internal nitric oxide production (U.S. Pat. No. 5,296,466), during the perioperative period or during surgery in a method for maintaining a steady-state hemoglobin concentration in a patient (WO 95/03068), and as part of a perioperative hemodilution procedure used prior to surgery in an autologous blood use method (U.S. Pat. Nos. 5,344,393 and 5,451,205). When a patient suffers a trauma (i.e., a wound or injury) resulting, for example, from surgery, an invasive medical procedure, or an accident, the trauma disturbs the patient's homeostasis. The patient's body biologically reacts to the trauma to restore homeostasis. This reaction is referred to herein as a naturally occurring stress response. If the body's stress response is inadequate or if it occurs well after the trauma is suffered, the patient is more prone to develop disorders.

III. Reduction of the Oxygen-Affinity of Hemoglobin

The major function of erythrocytes consists in the transport of molecular oxygen from the lungs to the peripheral tissues. The erythrocytes contain a high concentration of hemoglobin (30 pg per cell=35.5 g/100 ml cells) which forms a reversible adduct with $O_2$. The $O_2$-partial pressure in the lung is about 0.100 mm Hg, in the capillary system is about 0.70 mm Hg, against which $O_2$ must be dissociated from the oxygenated hemoglobin. Under physiological conditions, only about 25% of the oxygenated hemoglobin may be deoxygenated; about 0.75% is carried back to the lungs with the venous blood. Thus, the major fraction of the hemoglobin-$O_2$ adduct is not used for the $O_2$ transport.

Interactions of hemoglobin with allosteric effectors enable an adaptation to the physiological requirement of maximum $O_2$ release from the hemoglobin-$O_2$ adduct with simultaneous conservation of the highest possible $O_2$ partial pressure in the capillary system. 2,3-Diphosphoglycerate increases the half-saturation pressure of stripped hemoglobin at pH 7.4 from $P(O_2)$ (½)=9.3 mm Hg (37° C.), and 4.3 mm Hg (25° C.) to $P(O_2)$ (½)=23.7 mm Hg (37° C.), and 12.0 mm Hg (25° C.), respectively (Imai, K. and Yonetani, T. (1975), *J. Biol. Chem.* 250, 1093-1098). A significantly stronger decrease of the $O_2$ affinity, i.e., enhancement of the $O_2$ half-saturation pressure has been achieved for stripped hemoglobin by binding of inositol hexaphosphate (phytic acid; IHP) (Ruckpaul, K. et al. (1971) *Biochim. Biophys. Acta* 236, 211-221) isolated from vegetal tissues. Binding of IHP to hemoglobin increases the $O_2$ half-saturation pressure to $P(O_2)$ (½)=96.4 mm Hg (37° C.), and $P(O_2)$ (½)=48.4 mm Hg (25° C.), respectively. IHP, like 2,3-diphosphoglycerate and other polyphosphates cannot penetrate the erythrocyte membrane.

Furthermore, the depletion of DPG and ATP in stored red cells leads to a progressive increase of the oxygen affinity of hemoglobin contained therein (Balcerzak, S. et al. (1972) *Adv. Exp. Med. Biol.* 28, 453-447). The $O_2$-binding isotherms are measured in the absence of $CO_2$ and at constant pH (pH 7.4) in order to preclude influences of these allosteric effectors on the half-saturation pressure. The end point of the progressive polyphosphate depletion is defined by $P(O_2)$ (½)=4.2 mm Hg, which is the half-saturation pressure of totally phosphate-free (stripped) hemoglobin; the starting point, i.e., $P(O_2)$ (½) of fresh erythrocytes, depends on the composition of the suspending medium. From these polyphosphate depletion curves a new functional parameter of stored erythrocytes can be determined, the so-called half-life time of intra-erythrocytic polyphosphate: 9 d (days) in isotonic 0.1 M bis-Tris buffer pH 7.4; and 12 d (days) in acid-citrate-dextrose conservation (ACD) solution.

Several years ago, it was discovered that the antilipidemic drug clofibric acid lowered the oxygen affinity of hemoglobin solutions (Abraham et al., *J. Med. Chem.* 25, 1015 (1982), and Abraham et al., *Proc. Natl. Acad. Sci. USA* 80, 324 (1983)). Bezafibrate, another antilipidemic drug, was later found to be much more effective in lowering the oxygen affinity of hemoglobin solutions and suspensions of fresh, intact red cells (Perutz et al., *Lancet,* 881, Oct. 15, 1983). Subsequently, X-ray crystallographic studies have demonstrated that clofibric acid and bezafibrate bind to the same sites in the central water cavity of deoxyhemoglobin, and that one bezafibrate molecule will span the sites occupied by two clofibric acid molecules. Bezafibrate and clofibric acid act by stabilizing the deoxy structure of hemoglobin, shifting the allosteric equilibrium toward the low affinity deoxy form. Bezafibrate and clofibric acid do not bind in any specific manner to either oxy- or carbonmonoxyhemoglobin.

In more recent investigations, a series of urea derivatives [2-[4-[[(arylamino)carbonyl]amino]phenoxy]-2-methylpropionic acids] was discovered that has greater allosteric potency than bezafibrate at stabilizing the deoxy structure of hemoglobin and shifting the allosteric equilibrium toward the low oxygen affinity form (Lalezari, *Proc. Natl. Acad. Sci. USA* 85, 6117 (1988)).

Drugs which can allosterically modify hemoglobin toward a lower oxygen affinity state hold potential for many clinical applications, such as for the treatment of ischemia, shock, and polycythemia, and as radiosensitizing agents. Unfortunately, the effects of bezafibrate and the urea derivatives discussed above have been found to be significantly inhibited by serum albumin, the major protein in blood serum (Lalezari et al., *Biochemistry,* 29, 1515 (1990)). Therefore, the clinical usefulness of these drugs is seriously undermined because in whole blood and in the body, the drugs would be bound by serum albumin instead of reaching the red cells, crossing the red cell membrane, and interacting with hemoglobin protein molecule to produce the desired effect.

There has been considerable interest in medicine, the military health services, and the pharmaceutical industry in finding methods to increase blood storage life; to discover radio sensitization agents; and to develop new blood substitutes. In all these instances, the availability of either autologous blood or recombinant Hb solutions is of major interest, provided the oxygen affinity can be decreased to enhance oxygen delivery to the tissues.

2,3-Diphosphoglycerate (2,3-DPG) is the normal physiological ligand for the allosteric site on hemoglobin. However, phosphorylated inositols are found in the erythrocytes of birds and reptiles. Specifically, inositol hexaphosphate (IHP), as known as phytic acid, displaces hemoglobin-bound 2,3-DPG, binding to the allosteric site with one-thousand times greater affinity. Unfortunately, IHP is unable to pass unassisted across the erythrocyte membrane.

IV. Enhanced Oxygen Delivery in Mammals

The therapy of oxygen deficiencies requires the knowledge of parameters which characterize both the $O_2$ transport capacity and the $O_2$ release capacity of human RBCs. The parameters of the $O_2$ transport capacity, i.e., Hb concentration, the number of RBCs, and hemocrit, are commonly used in clinical diagnosis. However, the equally important parameters of the $O_2$ release capacity, i.e., $O_2$ half-saturation pressure of Hb and RBCs, and the amounts of high and low oxygen affinity hemoglobins in RBCs, are not routinely determined and were not given serious consideration until pioneering work by Gerosonde and Nicolau (*Blut,* 1979, 39, 1-7).

In the 1980s, Nicolau et al. (*J. Appl. Physiol.* 58:1810-1817 (1985); "PHYTIC ACID: Chemistry and Applications"; Graf, E., Ed.; Pilatus Press, Minneapolis, Minn., USA; 1986; and *Proc. Natl. Acad. Sci. USA* 1987, 84, 6894-6898) reported that the encapsulation in red blood cells (RBCs) of IHP, via a technique of controlled lysis and resealing, results in a significant decrease in the hemoglobin affinity for oxygen. The procedure yielded RBCs with unchanged life spans, normal ATP and K+ levels, and normal rheological competence. Enhancement of the $O_2$-release capacity of these cells brought about significant physiological effects in piglets: 1) reduced cardiac output, linearly dependent on the $P_{50}$ value of the RBCs; 2) increased arteriovenous difference; and 3) improved tissue oxygenation. Long term experiments showed that in piglets the high $P_{50}$ value of IHP-RBCs was maintained over the entire life spans of the RBCs.

More recently, Nicolau et al. (*TRANSFUSION* 1995, 35, 478-486; and U.S. Pat. No. 5,612,207) reported the use of a large-volume, continuous-flow electroporation system for the encapsulating IHP in human RBCs. These modified RBCs possess $P_{50}$ values of approximately 50 torr, roughly twice that of unmodified human RBCs. Additionally, 85% of the RBCs survived the electroporation process, displaying hematologic indices nearly identical to those of unmodified RBCs. Nicolau's electroporation system processes one unit of blood every ninety minutes.

Although it is evident that methods of enhancing oxygen delivery to tissues have potential medical applications, currently there are no methods clinically available for increasing tissue delivery of oxygen bound to hemoglobin. Transient, e.g., 6 to 12 hour, elevations of oxygen deposition have been described in experimental animals using either DPG or molecules that are precursors of DPG. However, the natural regulation of DPG synthesis in vivo and its relatively short biological half-life limit the DPG concentration and the duration of increased tissue $P(O_2)$, and thus limit its therapeutic usefulness.

Additionally, as reported in *Genetic Engineering News*, Vol. 12, No. 6, Apr. 15, 1992, several groups are attempting to engineer free oxygen-carrying hemoglobin as a replacement for human blood. Recombinant, genetically modified human hemoglobin that does not break down in the body and that can readily release up to 30% of its bound oxygen is currently being tested by Somatogen, Inc., of Boulder Colo. While this product could be useful as a replacement for blood lost in traumatic injury or surgery, it would not be effective to increase $PO_2$ levels in ischemic tissue, since its oxygen release capacity is equivalent to that of natural hemoglobin (27-30%). As are all recombinant products, this synthetic hemoglobin is also likely to be a costly therapeutic.

Synthetic human hemoglobin has also been produced in neonatal pigs by injection of human genes that control hemoglobin production. This product may be a less expensive product than the Somatogen synthetic hemoglobin, but it does not solve problems with oxygen affinity and breakdown of hemoglobin in the body.

V. Specific Clinical Applications of Enhanced Oxygen Delivery

There are numerous clinical conditions that would benefit from treatments that would increase tissue delivery of oxygen bound to hemoglobin. For example, the leading cause of death in the United States today is cardiovascular disease. The acute symptoms and pathology of many cardiovascular diseases, including congestive heart failure, myocardial infarction, stroke, intermittent claudication, and sickle cell anemia, result from an insufficient supply of oxygen in fluids that bathe the tissues. Likewise, the acute loss of blood following hemorrhage, traumatic injury, or surgery results in decreased oxygen supply to vital organs. Without oxygen, tissues at sites distal to the heart, and even the heart itself, cannot produce enough energy to sustain their normal functions. The result of oxygen deprivation is tissue death and organ failure.

Although the attention of the American public has long been focused on the preventive measures required to alleviate heart disease, such as exercise, appropriate dietary habits, and moderation in alcohol consumption, deaths continue to occur at an alarming rate. Since death results from oxygen deprivation, which in turn results in tissue destruction and/or organ dysfunction, one approach to alleviate the life-threatening consequences of cardiovascular disease is to increase oxygenation of tissues during acute stress. The same approach is also appropriate for persons suffering from blood loss or chronic hypoxic disorders, such as congestive heart failure.

SUMMARY OF THE INVENTION

One aspect of the present invention relates to inositol hexaphosphate (IHP) derivatives comprising an internal pyrophosphate moiety. Another aspect of the present invention relates to compositions, consisting essentially of aliphatic ammonium cations or of metal cations, such as sodium cations, and IHP derivatives comprising an internal pyrophosphate moiety. The present invention also relates to methods for modulating the oxygen affinity of hemoglobins comprising the use as allosteric effectors of hemoglobin of the aforementioned IHP derivatives and the compositions comprising them.

An aliphatic ammonium cation is substituted with one or more aliphatic groups, which can be the same or different. In certain embodiments, the aliphatic ammonium cation is a primary ammonium cation represented by the general formula $RN^+H_3$, wherein R is an aliphatic group, preferably an alkyl, preferably a lower alkyl, i.e., a $C_1$-$C_8$ alkyl, and more preferably a $C_3$-$C_{10}$ cycloalkyl. In certain preferred embodiments, the ammonium cation is derived from cyclic amines.

In certain embodiments, the present invention relates to compounds, and compositions thereof, that deliver IHP into erythrocytes in vivo or ex vivo, for lowering the oxygen affinity of hemoglobin in red blood cell suspensions and whole blood. It is an object of this invention to provide methods for delivering IHP into erythrocytes in whole blood, utilizing compounds or compositions thereof that do not lose their effectiveness in the presence of whole blood.

In certain embodiments, the present invention relates to a method of treating a subject suffering from one or more diseases where an increase in oxygen delivery of hemoglobin would be beneficial, comprising the steps of treating red blood cells or whole blood ex vivo with one or more compounds or compositions of the present invention, followed by suitably purifying said red blood cells or whole blood, and administering the prepared red blood cells or whole blood to said subject. By 'suitably purifying' it is meant a method of washing and separating, for example by centrifugation, the red blood cell-allosteric effector or whole blood-allosteric effector suspension, and discarding the supernatant until no non-encapsulated allosteric effector can be detected. An exemplary method is presented in detail by Nicolau et al. in U.S. Pat. No. 5,612,207, which is incorporated by reference herein.

Ligands for the allosteric site of hemoglobin interact with the hemoglobin molecule and impact its ability to bind oxygen. This invention is particularly concerned with the delivery of IHP derivatives comprising an internal pyrophosphate moiety, thereby causing oxygen to be bound relatively less tightly to hemoglobin, such that oxygen is off-loaded from the hemoglobin molecule more easily.

The process of allosterically modifying hemoglobin towards a lower oxygen affinity state in whole blood may be used in a wide variety of applications, including treatments for ischemia, heart disease, wound healing, radiation therapy of cancer, and adult respiratory distress syndrome (ARDS). Furthermore, a decrease in the oxygen affinity of hemoglobin in whole blood will extend its useful shelf-life vis-à-vis transfusions, and/or restore the oxygen carrying capacity of aged blood.

Another condition which could benefit from an increase in the delivery of oxygen to the tissues is anemia. A significant portion of hospital patients experience anemia or a low "crit" caused by an insufficient quantity of red blood cells or hemoglobin in their blood. This leads to inadequate oxygenation of their tissues and subsequent complications. Typically, a physician can temporarily correct this condition by transfusing the patient with units of packed red blood cells.

Enhanced blood oxygenation may also reduce the number of heterologous transfusions and allow use of autologous transfusions in more cases. The current method for treatment of anemia or replacement of blood loss is transfusion of whole human blood. It is estimated that three to four million patients receive transfusions in the U.S. each year for surgical or medical needs. In situations where there is more time it is advantageous to avoid the use of donor or heterologous blood, instead using autologous blood. However, often the amount of blood which can be drawn and stored prior to surgery limits the use of autologous blood. Typically, a surgical patient does not have enough time to donate a sufficient quantity of blood prior to surgery. A surgeon would like to have several units of blood available. As each unit requires a period of several weeks between donations, and because a unit can not be drawn less than two weeks prior to surgery, it is often impossible to sequester an adequate supply of blood. By processing autologous blood with an IHP derivative comprising an internal pyrophosphate moiety, less blood is required and it becomes possible to avoid the transfusion of heterologous blood.

Because IHP-treated RBCs may release up to 2-3 times as much oxygen as untreated red cells, in many cases, a physician will need to transfuse fewer units of IHP-treaded red cells. This exposes the patient to less heterologous blood, decreases the extent of exposure to diseases from blood donors and minimizes immune function disturbances secondary to transfusions. The ability to infuse more efficient red blood cells is also advantageous when the patients blood volume is excessive. In more severe cases, where oxygen transport is failing, the ability to improve rapidly a patient's tissue oxygenation may be life saving.

BRIEF DESCRIPTION OF THE FIGURES

FIG. 8 depicts 2a): mixed $^{31}$P NMR of all compounds 5 (kf31, kf53, kf56); 2b): 2D $^{31}$P NMR COSY experiment of compound kf53.

FIG. 10 depicts the general scheme for the synthesis of IHP derivatives.

DETAILED DESCRIPTION OF THE INVENTION

I. Overview

Figure 1:
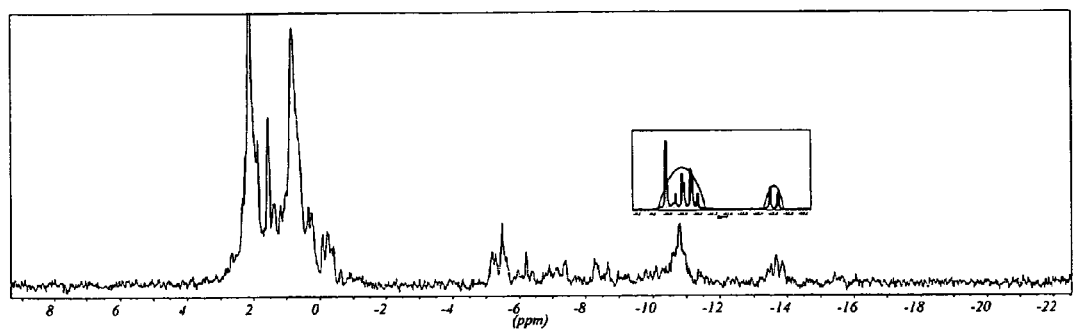
FIG. 1 depicts the $^{31}$P NMR spectrum of IHP-cholesteryloxy carbonyl hepta N,N-dimethylcyclohexylammonium salt and the $^{31}$P NMR spectrum of IHP-tripyrophosphate ("ITPP").

The process of allosterically modifying hemoglobin towards a low oxygen affinity state in whole blood could be used in a wide variety of applications including in treatments for ischemia, heart disease, complications associated with angioplasty, wound healing, radiation therapy of cancer, adult respiratory distress syndrome (ARDS), etc., in extending the shelf-life of blood or restoring the oxygen carrying capacity of out-dated blood, and as sensitizers for x-ray irradiation in cancer therapy, as well as in many other applications.

This invention is related to the use of allosteric hemoglobin modifier compounds in red blood cell suspensions, e.g., in whole blood. Serum albumin, which is the most abundant protein in blood plasma, has been identified as inhibiting the allosteric effects of clofibric acid, bezafibrate, and L3,5/L3, 4,5. The precise nature of this inhibition is not fully understood, but appears to be related to these compounds binding to the serum albumin. In contrast, the subject compounds have been found to be relatively unaffected by the presence of serum albumin. Ligands for the allosteric site of hemoglobin that are not adversely effected by serum albumin represent particularly good candidates for drug applications, since the performance of the drug will not be frustrated by the presence of serum albumin present in a patient's blood.

This invention relates to the incorporation of a wide variety of therapeutically useful substances into mammalian red blood cells (RBCs), which could not previously be accomplished without unacceptable losses of RBC contents and/or integrity. In particular, the compounds and methods of the present invention make possible the introduction or incorporation into RBCs of anionic agents, such as DNA, RNA, chemotherapeutic agents, and antibiotic agents. These and other water-soluble substances may be used for a desired slow continuous delivery or targeted delivery when the treated and purified RBC carrier is later injected in vivo. The particular anion or polyanion to be selected can be based on whether an allosteric effector of hemoglobin would be desirable for a particular treatment.

The present invention provides a novel method for increasing the oxygen-carrying capacity of erythrocytes. In accordance with the method of the present invention, the IHP combines with hemoglobin in a stable way, and shifts its oxygen releasing capacity. Erythrocytes with IHP-hemoglobin can release more oxygen per molecule than hemoglobin alone, and thus more oxygen is available to diffuse into tissues for each unit of blood that circulates. IHP is preferably added to red blood cells in vitro or ex vivo, as it appears that it is toxic to animals under certain circumstances.

Another advantage of IHP-treated red blood cells is that they show the Bohr effect in circulation and when stored. Normal red blood cells that have been stored do not regain their maximum oxygen carrying capacity in circulation for approximately 24 hours. This is because the DPG present in normal red blood cells is degraded by native enzymes, e.g., phosphatases, during storage and must be replaced by the body after transfusion. In contrast, red blood cells treated according to the present invention retain their maximum oxygen carrying capacity during storage and therefore can deliver oxygen to the tissues in response to demand immediately after transfusion into a human or animal because there are no native enzymes in erythrocytes which degrade IHP.

IHP-treated RBCs may be used in the treatment of acute and chronic conditions, including, but not limited to, hospitalized patients, cardiovascular operations, chronic anemia, anemia following major surgery, coronary infarction and associated problems, chronic pulmonary disease, cardiovascular patients, autologous transfusions, as an enhancement to packed red blood cells transfusion (hemorrhage, traumatic injury, or surgery) congestive heart failure, myocardial infarction (heart attack), stroke, peripheral vascular disease, intermittent claudication, circulatory shock, hemorrhagic shock, anemia and chronic hypoxia, respiratory alkalemia, metabolic alkalosis, sickle cell anemia, reduced lung capacity caused by pneumonia, surgery, complications associated with angioplasty, pneumonia, trauma, chest puncture, gangrene, anaerobic infections, blood vessel diseases such as diabetes, substitute or complement to treatment with hyperbaric pressure chambers, intra-operative red cell salvage, cardiac inadequacy, anoxia-secondary to chronic indication, organ transplant, carbon monoxide, nitric oxide, and cyanide poisoning.

This invention is related to a method of treating a subject for any one or more of the above diseases comprising the steps of treating red blood cells or whole blood ex vivo with one or more compounds or compositions of the present invention, followed by suitably purifying said red blood cells or whole blood, and administering the thus prepared red blood cells or whole blood to said subject. By 'suitably purifying' it is meant a method of washing and separating the red blood cell- or whole blood-allosteric effector suspension and discarding the supernatant until no non-encapsulated allosteric effector can be detected, e.g., as devised by Nicolau et al. in U.S. Pat. No. 5,612,207. Alternatively, a compound comprised of an allosteric effector can be administered directly to a subject if the compound does not have toxic effects in the subject, or at least its beneficial effects predominate over its toxicity in a subject. Toxicity of a compound in a subject can be determined according to methods known in the art.

Treating a human or animal for any one or more of the above disease states is done by transfusing into the human or animal between approximately 0.1 and 6 units (1 unit=500 mL) of IHP-treated blood that has been prepared according to the present invention. In certain cases, blood exchange with IHP-treated blood may be possible. The volume of IHP-treated red blood cells that is administered to the human or animal will depend upon the value of $P_{50}$ for the IHP-treated RBCs. It is to be understood that the volume of IHP-treated red blood cells that is administered to the patient can vary and still be effective. IHP-treated RBCs are similar to normal red blood cells in every respect except that their $P_{50}$ value is shifted towards higher partial pressures of $O_2$. Erythrocytes release oxygen only in response to demand by organs and tissue. Therefore, the compounds, compositions thereof, and methods of the present invention will only restore a normal level of oxygenation to healthy tissue, avoiding the cellular damage that is associated with an over-abundance of oxygen.

Because the compounds, compositions, and methods of the present invention are capable of allosterically modifying hemoglobin to favor the low oxygen affinity "T" state (i.e., right shifting the equilibrium curve), RBC's or whole blood treated with the compounds of the present invention and subsequently purified will be useful in treating a variety of disease states in mammals, including humans; wherein tissues suffer from low oxygen tension, such as cancer and ischemia. Furthermore, as disclosed by Hirst et al. (Radiat. Res., 112, (1987), pp. 164), decreasing the oxygen affinity of hemoglobin in circulating blood has been shown to be beneficial in the radiotherapy of tumors. RBC's or whole blood treated with the compounds of the present invention and subsequently purified may be administered to patients in whom the affinity of hemoglobin for oxygen is abnormally high. For example, certain hemoglobinopathies, certain respiratory distress syndromes, e.g., respiratory distress syndromes in new born infants aggravated by high fetal hemoglobin levels, and conditions in which the availability of hemoglobin/oxygen to the tissues is decreased (e.g., in ischemic conditions such as peripheral vascular disease, coronary occlusion, cerebral vascular accidents, or tissue transplant). The compounds and compositions may also be used to inhibit platelet aggregation, antithrombotic purposes, and wound healing.

Additionally, the compounds and compositions of the present invention can be added to whole blood or packed cells preferably at the time of storage or at the time of transfusion in order to facilitate the dissociation of oxygen from hemoglobin and improve the oxygen delivering capability of the blood. When blood is stored, the hemoglobin in the blood tends to increase its affinity for oxygen by losing 2,3-diphosphoglycerides. As described above, the compounds and compositions of this invention are capable of reversing and/or preventing the functional abnormality of hemoglobin observed when whole blood or packed cells are stored. The compounds and compositions may be added to whole blood or red blood cell fractions in a closed system using an appropriate reservoir in which the compound or composition is placed prior to storage or which is present in the anticoagulating solution in the blood collecting bag.

Administration to a patient can be achieved by intravenous or intraperitoneal injection where the dose of treated red blood cells or whole blood and the dosing regiment is varied according to individual's sensitivity and the type of disease state being treated. Solid tumors are oxygen deficient masses. The compounds, compositions and methods of this invention may be exploited to cause more oxygen to be delivered to tumors, increasing radical formation and thereby increasing tumor killing during radiation. In this context, such IHP-treated blood will only be used in conjunction with radiotherapy.

The compounds, compositions and methods of this invention may be exploited to cause more oxygen to be delivered at low blood flow and low temperatures, providing the ability to decrease or prevent the cellular damage, e.g., myocardial or neuronal, typically associated with these conditions.

The compounds, compositions and methods of this invention may be exploited to decrease the number of red blood cells required for treating hemorrhagic shock by increasing the efficiency with which they deliver oxygen.

Damaged tissues heal faster when there is better blood flow and increased oxygen tension. Therefore, the compounds, compositions and methods of this invention may be exploited to speed wound healing. Furthermore, by increasing oxygen delivery to wounded tissue, the compounds, compositions and methods of this invention may play a role in the destruction of infection causing bacteria at a wound.

The compounds, compositions and methods of this invention may be effective in enhancing the delivery oxygen to the brain, especially before complete occlusion and reperfusion injuries occur due to free radical formation. Furthermore, the compounds, compositions and methods of this invention of this invention should reduce the expansion of arterioles under both hypoxic and hypotensive conditions.

The compounds, compositions and methods of this invention of this invention should be capable of increasing oxygen delivery to blocked arteries and surrounding muscles and tissues, thereby relieving the distress of angina attacks.

Acute respiratory disease syndrome (ARDS) is characterized by interstitial and/or alveolar edema and hemorrhage as well as perivascular lung edema associated with the hyaline membrane, proliferation of collagen fibers, and swollen epithelium with increased pinocytosis. The enhanced oxygen delivering capacity provided to RBCs by the compounds, compositions and methods of this invention could be used in the treatment and prevention of ARDS by militating against lower than normal oxygen delivery to the lungs.

There are several aspects of cardiac bypass surgery that make attractive the use of compounds or compositions or methods of the present invention. First, the compounds and compositions of the present invention may act as neuroprotective agents. After cardiac bypass surgery, up to 50-70% of patients show some signs of cerebral ischemia based on tests of cognitive function. Up to 5% of these patients have evidence of stroke. Second, cardioplegia is the process of stopping the heart and protecting the heart from ischemia during heart surgery. Cardioplegia is performed by perfusing the coronary vessels with solutions of potassium chloride and bathing the heart in ice water. However, blood cardioplegia is also used. This is where potassium chloride is dissolved in blood instead of salt water. During surgery the heart is deprived of oxygen and the cold temperature helps slow down metabolism. Periodically during this process, the heart is perfused with the cardioplegia solution to wash out metabolites and reactive species. Cooling the blood increases the oxygen affinity of its hemoglobin, thus making oxygen unloading less efficient. However, treatment of blood cardioplegia with RBC's or whole blood previously treated with compounds or compositions of the present invention and subsequently purified will counteract the effects of cold on oxygen affinity and make oxygen release to the ischemic myocardium more efficient, possibly improving cardiac function after the heart begins to beat again. Third, during bypass surgery the patient's blood is diluted for the process of pump prime. This hemodilution is essentially acute anemia. Because the compounds and compositions of the present invention make oxygen transport more efficient, their use during hemodilution (whether in bypass surgery or other surgeries, such as orthopedic or vascular) would enhance oxygenation of the tissues in an otherwise compromised condition. Additionally, the compounds and methods of the present invention will also find use in patients undergoing angioplasty, who may experience acute ischemic insult, e.g., due to the dye(s) used in this procedure.

Additionally, microvascular insufficiency has been proposed by a number of investigators as a possible cause of diabetic neuropathy. The interest in microvascular derangement in diabetic neuropathic patients has arisen from studies suggesting that absolute or relative ischemia may exist in the nerves of diabetic subjects due to altered function of the endo- and/or epineurial blood vessels. Histopathologic studies have shown the presence of different degrees of endoneurial and epineurial microvasculopathy, mainly thickening of blood vessel wall or occlusion. A number of functional disturbances have also been demonstrated in the microvasculature of the nerves of diabetic subjects. Studies have demonstrated decreased neural blood flow, increased vascular resistance, decreased $pO_2$ and altered vascular permeability characteristics such as a loss of the anionic charge barrier and decreased charge selectivity. Abnormalities of cutaneous blood flow correlate with neuropathy, suggesting that there is a clinical counterpart to the microvascular insufficiency that may prove to be a simple non-invasive test of nerve fiber dysfunction. Accordingly, patients suffering from diabetic neuropathies and/or other neurodegenerative disorders will likely benefit from treatment based on the compounds and methods of the present invention.

Red blood cells or whole blood previously treated with the compounds of the present invention and subsequently suitably purified may be used to enhance oxygen delivery in any organism, e.g., fish, that uses a hemoglobin with an allosteric binding site.

II. Definitions

For convenience, certain terms employed in the specification, examples, and appended claims are collected here. As used throughout this specification and the claims, the following terms have the following meanings:

The term "hemoglobin" includes all naturally- and non-naturally-occurring hemoglobin.

The term "hemoglobin preparation" includes hemoglobin in a physiologically compatible carrier or lyophilized hemoglobin reconstituted with a physiologically compatible carrier, but does not include whole blood, red blood cells or packed red blood cells.

The term "toxic" refers to a property where the deleterious effects are greater than the beneficial effects.

The term "nontoxic" refers to a property where the beneficial effects are greater than the deleterious effects.

The term "whole blood" refers to blood containing all its natural constituents, components, or elements or a substantial amount of the natural constituents, components, or elements. For example, it is envisioned that some components may be removed by the purification process before administering the blood to a subject.

"Purified", "purification process", and "purify" all refer to a state or process of removing one or more compounds of the present invention from the red blood cells or whole blood such that when administered to a subject the red blood cells or whole blood is nontoxic.

"Non-naturally-occurring hemoglobin" includes synthetic hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, transgenic DNA technology, protein synthesis, and other mutation-inducing methods.

"Chemically-modified hemoglobin" is a natural or non-natural hemoglobin molecule which is bonded to another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin.

"Oxygen affinity" means the strength of binding of oxygen to a hemoglobin molecule. High oxygen affinity means hemoglobin does not readily release its bound oxygen molecules.

The $P_{50}$ is a measure of oxygen affinity.

"Cooperativity" refers to the sigmoidal oxygen-binding curve of hemoglobin, i.e., the binding of the first oxygen to one subunit within the tetrameric hemoglobin molecule enhances the binding of oxygen molecules to other unligated subunits. It is conveniently measured by the Hill coefficient (n[max]). For Hb A, n[max]=3.0.

The term "treatment" is intended to encompass also prophylaxis, therapy and cure. "Ischemia" means a temporary or prolonged lack or reduction of oxygen supply to an organ or skeletal tissue. Ischemia can be induced when an organ is transplanted, or by conditions such as septic shock and sickle cell anemia.

"Skeletal tissue" means the substance of an organic body of a skeletal organism consisting of cells and intercellular material, including but not limited to epithelium, the connective tissues (including blood, bone and cartilage), muscle tissue, and nerve tissue.

"Ischemic insult" means damage to an organ or skeletal tissue caused by ischemia.

"Subject" means any living organism, including humans, and mammals.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

As used herein, the term "surgery" refers to the treatment of diseases, injuries, and deformities by manual or operative methods. Common surgical procedures include, but are not limited to, abdominal, aural, bench, cardiac, cineplastic, conservative, cosmetic, cytoreductive, dental, dentofacial, general, major, minor, Moh's, open heart, organ transplantation, orthopedic, plastic, psychiatric, radical, reconstructive, sonic, stereotactic, structural, thoracic, and veterinary surgery. The method of the present invention is suitable for patients that are to undergo any type of surgery dealing with any portion of the body, including but not limited to those described above, as well as any type of any general, major, minor, or minimal invasive surgery.

"Minimally invasive surgery" involves puncture or incision of the skin, or insertion of an instrument or foreign material into the body. Non-limiting examples of minimal invasive surgery include arterial or venous catheterization, transurethral resection, endoscopy (e.g., laparoscopy, bronchoscopy, uroscopy, pharyngoscopy, cystoscopy, hysteroscopy, gastroscopy, coloscopy, colposcopy, celioscopy, sigmoidoscopy, and orthoscopy), and angioplasty (e.g., balloon angioplasty, laser angioplasty, and percutaneous transluminal angioplasty).

The term "$ED_{50}$" means the dose of a drug that produces 50% of its maximum response or effect. Alternatively, the dose that produces a pre-determined response in 50% of test subjects or preparations.

The term "$LD_{50}$" means the dose of a drug that is lethal in 50% of test subjects.

The term "therapeutic index" refers to the therapeutic index of a drug defined as $LD_{50}/ED_{50}$.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "structure-activity relationship (SAR)" refers to the way in which altering the molecular structure of drugs alters their interaction with a receptor, enzyme, etc.

The term "pyrophosphate" refers to the general formula below:

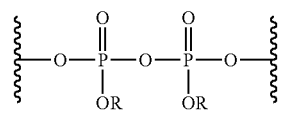

wherein R is selected independently for each occurrence from the group consisting of H, cations and hydrocarbon groups.

The terms "internal pyrophosphate moiety", "internal pyrophosphate ring", and "cyclic pyrophosphate" refer to the structure feature below:

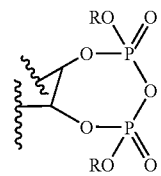

wherein R is selected independently for each occurrence from the group consisting of H, cations, alkyl, alkenyl, alkynyl, aralkyl, aryl, and acyl groups.

The term "IHP-monopyrophosphate" (abbreviated as "IMPP") refers to inositol hexaphosphate where two orthopyrophosphates were condensed to one internal pyrophosphate ring.

The term "IHP-tripyrophosphate" or "inositol tripyrophosphate" (both abbreviated as "ITPP") refers to inositol hexaphosphate with three internal pyrophosphate rings.

The term "2,3-diphosph-D-glyceric acid" (DPG) refers to the compound below:

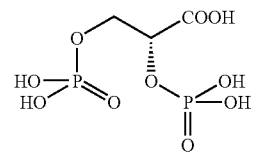

The term "2,3-cyclopyrophosphoglycerate" (CPPG) refers to the compound below:

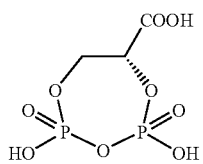

The term "ammonium cation" refers to the structure below:

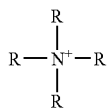

wherein R represents independently for each occurrence H or a substituted or unsubstituted aliphatic group. An "aliphatic ammonium cation" refers to the above structure when at least one R is an aliphatic group. A "quaternary ammonium cation" refers to the above structure when all four occurrences of R independently represent aliphatic groups. R can be the same for two or more occurrences, or different for all four.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, Advanced Organic Chemistry, McGraw Hill Book Company, New York, (1977 edition) pp. 251-259. The Hammett constant values are generally negative for electron donating groups (σ[P]=−0.66 for $NH_2$) and positive for electron withdrawing groups (σ[P]=0.78 for a nitro group), (σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

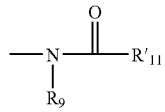

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

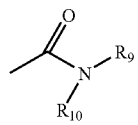

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S—alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

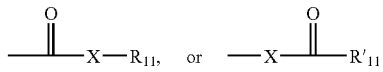

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$^{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

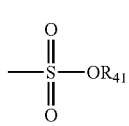

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

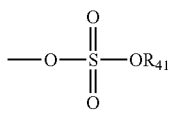

in which $R_{41}$ is as defined above.

The term "sulfonamido" is art recognized and includes a moiety that can be represented by the general formula:

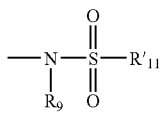

in which $R_9$ and $R'_{11}$ are as defined above.

The term "sulfamoyl" is art-recognized and includes a moiety that can be represented by the general formula:

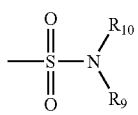

in which $R_9$ and $R_{10}$ are as defined above.

The term "sulfonyl", as used herein, refers to a moiety that can be represented by the general formula:

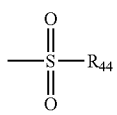

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

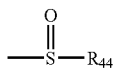

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Ele-

III. Compounds of the Invention

Several years ago, it was discovered that the antilipidemic drug clofibric acid lowered the oxygen affinity of hemoglobin solutions (Abraham et al., *J. Med. Chem.* 25, 1015 (1982), and Abraham et al., *Proc. Natl. Acad. Sci. USA* 80, 324 (1983)). Bezafibrate, another antilipidemic drug, was later found to be much more effective in lowering the oxygen affinity of hemoglobin solutions and suspensions of fresh, intact red cells (Perutz et al., *Lancet,* 881, Oct. 15, 1983). Subsequently, X-ray crystallographic studies have demonstrated that clofibric acid and bezafibrate bind to the same sites in the central water cavity of deoxyhemoglobin, and that one bezafibrate molecule will span the sites occupied by two clofibric acid molecules. Bezafibrate and clofibric acid act by stabilizing the deoxy structure of hemoglobin, shifting the allosteric equilibrium toward the low affinity deoxy form. Bezafibrate and clofibric acid do not bind in any specific manner to either oxy- or carbonmonoxyhemoglobin.

In later investigations, a series of urea derivatives [2-[4-[[(arylamino)carbonyl]-amino]phenoxy]-2-methylpropionic acids] was discovered that has greater allosteric potency than bezafibrate at stabilizing the deoxy structure of hemoglobin and shifting the allosteric equilibrium toward the low oxygen affinity form (Lalezari, Proc. Natl. Acad. Sci. USA 85, 6117 (1988)).

It has been determined that certain allosteric hemoglobin modifier compounds are hydrophobic molecules that can be bound to the body's neutral fat deposits and lipophilic receptors sites, thus lowering their potency due to a decreased concentration in RBCs. Administration of a hydrophobic compound, such as a mixture of anesthetic molecules, will saturate the body's neutral fat deposits and lipophilic receptor sites, and thereby increase the concentration of this type of allosteric modifiers in RBCs, where higher concentrations of effector will increase its ability to interact with hemoglobin, causing delivery of more oxygen. Ligands for the allosteric site of hemoglobin, also known as allosteric effectors of hemoglobin, include 2,3-diphosphoglycerate (DPG), inositol hexakisphosphate (IHP), bezafibrate (Bzf), LR16 and L35 (two recently synthesized derivatives of Bzf), and pyridoxal phosphate. Additionally, hemoglobin's affinity for oxygen can be modulated through electrostatic interactions with chloride and/or organophosphate anions present in RBCs. These effectors, which bind preferentially to the deoxy-Hb tetramers at a distance from the heme groups, play a major role in the adaptation of the respiratory properties of hemoglobin to either allometric-dependent oxygen needs or to various hypoxic environments. Additionally, protons and carbon dioxide are physiological regulators for the oxygen affinity of hemoglobin. The heterotropic allosteric interaction between the non-heme ligands and oxygen, collectively called the Bohr effect, facilitates not only the transport of oxygen but also the exchange of carbon dioxide.

The present invention relates to compositions, and methods of use thereof, consisting essentially of a nontoxic ammonia cation (preferably water-soluble), and inositol hexaphosphate (IHP, phytic acid) derivatives comprising an internal pyrophosphate ring. IHP is the most abundant form of phosphate in plants. IHP binds hemoglobin 1000 times more tightly than DPG and therefore triggers a decrease of the $O_2$/hemoglobin affinity with a subsequent release of oxygen. Because of IHP's superior hemoglobin binding properties over DPG, IHP represents a good pharmaceutical candidate for diseases characterized by a limited oxygen flow to organ tissues. Under normal physiological conditions, IHP bears at least 7 charges, making it very difficult for it to be transported across cell membranes. In order to answer the IHP delivery problem two approaches have been investigated: a) the ionic approach, which is based on a non-covalent interaction between IHP and the transport molecules, and b) the prodrug approach, which is based on the idea that a linker covalently bound to IHP will facilitate the transport of the polyphosphate inside the red blood cells. Approach a) was realized with the synthesis of a library of IHP derivatives ionically bound to lipophilic and non lipidic ammonium or polyammonium salts in U.S. application Ser. Nos. 09/920,310 and 09/920,140. The present invention expands upon approach b) wherein the covalently bound linker is an adjacent phosphate group or an acyl phosphate group including a cholesteryloxy carbonyl group, which under certain conditions eliminate to give an internal pyrophosphate ring.

In certain embodiments, the nontoxic ammonium cation is represented by the general formula $N^+(R)_4$, wherein R is, independently for each occurrence, H or an aliphatic group, which aliphatic group is preferably an alkyl, preferably a lower (C1-C8) alkyl, and more preferably a C3-C10 cyclic alkyl. In certain preferred embodiments, the ammonium cation is preferably derived from cyclic organic bases. In a particularly preferred embodiment, the ammonium cation is N,N-dimethylcyclohexylammonium (N,N-DMCHA) for the following reasons: a) it increases the lipophilisity of IHP and makes the molecule soluble in all organic solvents, without affecting its solubility in water, and b) as an ammonium salt of a tertiary amine, it doesn't react with the acyl anhydrides or alkyl formates.

In certain embodiments, the present invention is related to compounds, and compositions thereof, which deliver IHP into erythrocytes in vivo, in vitro, or ex vivo. Additionally, the invention is directed to the use of the compounds or compositions thereof that are effective in delivering IHP into erythrocytes, lowering the oxygen affinity state in red blood cell suspensions and whole blood. It is an object of this invention to provide methods for delivering IHP into erythrocytes in whole blood, utilizing compounds or compositions thereof that do not lose their effectiveness in the presence of normal concentrations of the remaining components of whole blood.

In certain embodiments, the present invention is related to a method of treating red blood cells or whole blood in vivo, in vitro, or ex vivo with one or more nontoxic compounds or compositions of the present invention, suitably purifying said red blood cells or whole blood, and administering said purified red blood cells or whole blood to a subject for any treatment where an increase in oxygen delivery by hemoglobin would be a benefit.

In part, the present invention is directed toward the design of water-soluble membrane compatible molecules comprising ammonium cationic moieties, e.g., lipophilic ammonium groups. These molecules form complexes with IHP derivatives comprising an internal pyrophosphate ring; such complexes are useful for the delivery of IHP into the cytoplasm of erythrocytes. In the cases of the monopyrophospate and tripyrophosphate derivatives and acylated derivatives of IHP, metal cations, e.g., sodium cations, may allow deliver of IHP into the cytoplasm of erythrocytes.

The ammonium group of the cationic component of the compounds of the present invention is particularly well suited for interaction with the phosphate residues of IHP and congeners thereof because of the coulombic interactions, i.e., the attraction between opposite charges, that can be established between the two moieties. The use of ammonium salts for the efficient delivery of IHP into mammalian erythrocytes is reported. Our data demonstrate the usefulness, convenience, and versatility of ammonium salts for delivery of IHP into the cytoplasm of mammalian cells.

In certain embodiments, the compounds of the present invention are represented by generalized structure I:

  I wherein $C^+$ represents independently for each occurrence an aliphatic ammonium cation, an alkali metal cation, an alkaline earth cation, or other suitable metal cation; and $A^{n-}$ represents a conjugate base of inositol hexaphosphate comprising an internal pyrophosphate ring or an acyl group, wherein n equals the number of cations comprised by $nC^+$.

In certain embodiments, the present invention relates to a pharmaceutical composition, comprising a nontoxic compound of the present invention; and a pharmaceutically acceptable excipient.

IV. Preparation of IHP Derivatives Containing Internal Pyrophosphate Rings

Our synthetic efforts toward acylated IHP derivatives was expected to have competition from two side reactions. One was hydrolysis of the acyl phosphates in water, a reaction dependent to some extent on pH. The other competitive reaction was the formation of an internal pyrophosphate ring via elimination of the carbonyl adducts by a vicinal phosphate group. The latter reaction proved to be characteristic of the IHP derivatives.

In certain embodiments, IHP derivatives comprising an internal pyrophosphate ring were prepared by heating IHP with acyl anhydrides or acyl chlorides as depicted in Scheme 1.

Scheme 1.
Synthesis of IHP-tripyrophosphate.

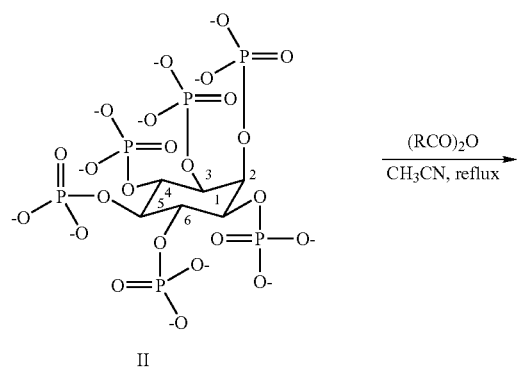

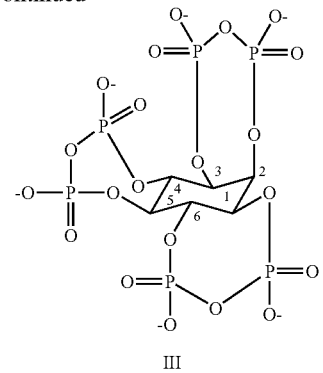

III

The proposed mechanism for this reaction is depicted in Scheme 2. The key step is presumed to be conversion of a phosphate oxygen into a leaving group by forming an acyl phosphate ester. Once the acyl phosphate ester forms, a vicinal phosphate group is well positioned to attack nucleophilically the central phosphorous atom and form the internal pyrophosphate ring.

Scheme 2.
Mechanism of internal pyrophosphate formation.

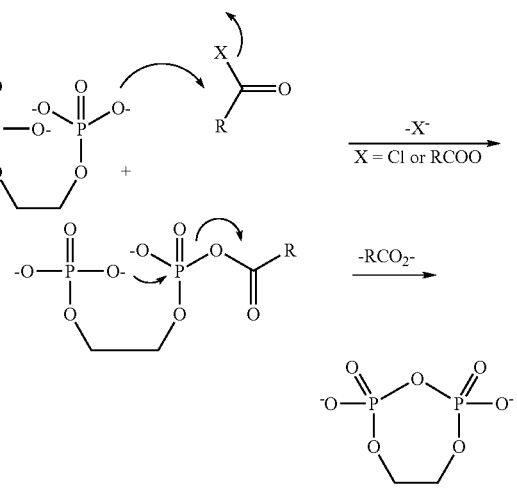

V. Synthesis of the IHP tripyrophosphate (ITPP) Na Salt

Identification of the Products of the Reactions of IHP with Excess of Acyl Anhydrides The literature procedures for the synthesis of the IHP tripyrophosphate include the conversion of the crystalline sodium phytate 1 to the free acid 2, by passage through a column of Dowex 50 H$^+$, Scheme 3. L. F. Johnson, M. E. Tate, *Can. J. Chem.*, 1969, 47, 63. The column eluate was adjusted to pH 8 with pyridine and evaporated to dryness to give compound 3. The residue was dissolved in water and pyridine containing N,N-dicyclohexylcarbodiimide (DCC) was added. The reaction mixture was heated at 50-60° C. for 6 h and evaporated to dryness to give product 4 (kf50A) as a pyridinium salt (checked by $^1$H, $^{31}$P, $^{13}$C NMR—all phosphorus moieties absorbed from −7 to −14 ppm at a pH range 2-3). The residue was extracted with water, filtered and the filtrate adjusted to pH 10 with 5 M NaOH. The sodium salt was precipitated by the addition of methanol and separated by centrifugation to give product 5 (kf56) (checked by $^1$H, $^{31}$P, NMR—all phosphorus moieties absorbed from −7 to −14 ppm at a pH 9, see FIG. 7, spectrum 1a for the $^{31}$P NMR spectrum of compound 5 (kf56).

Figure 7:
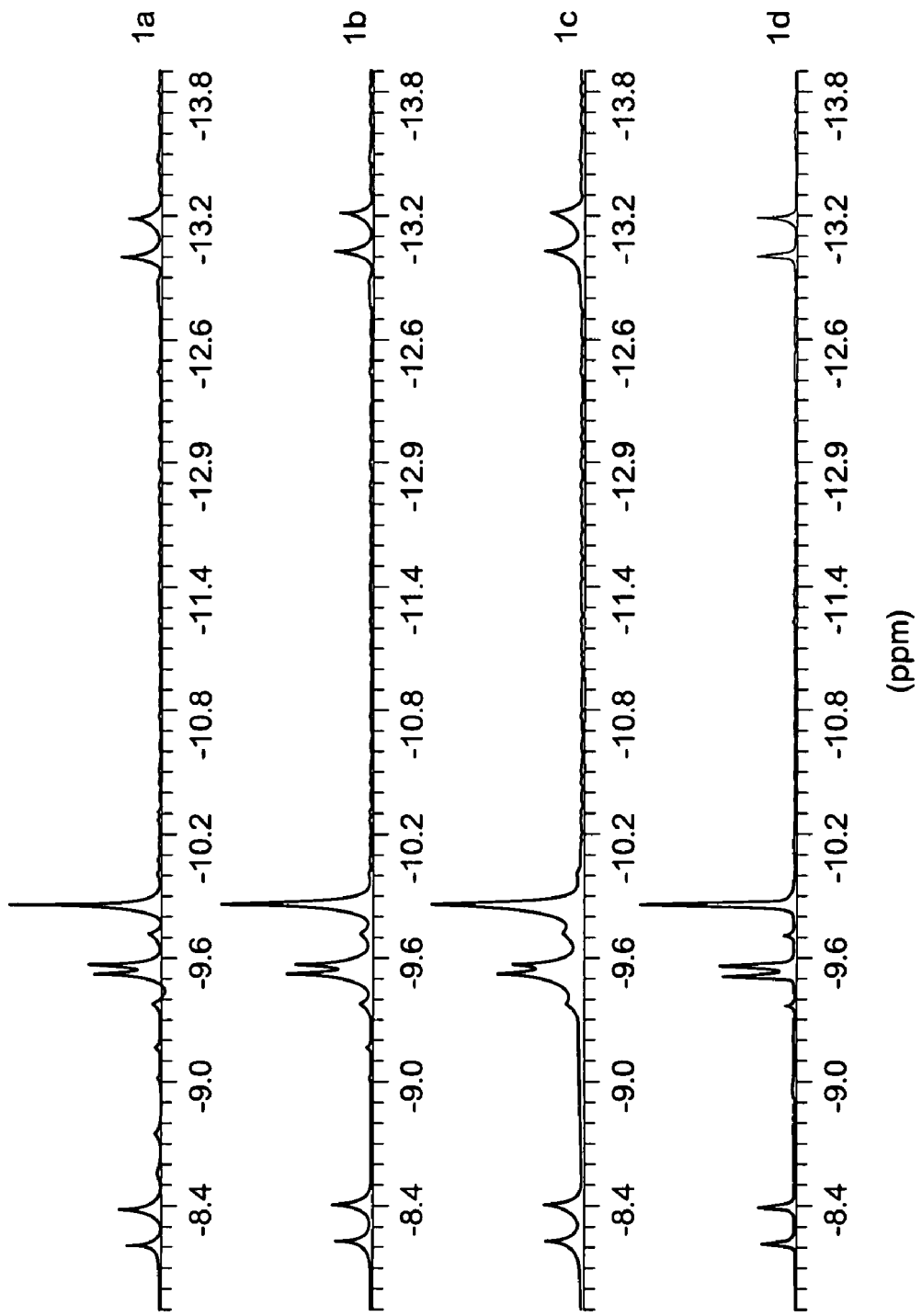
FIG. 7 depicts the $^{31}$P NMR spectra of kf56, kf53, kf31, kf31A, respectively.

To further prove the synthesis of the tripyrophosphate sodium salt, part of compound 4 (kf50A) was passed through a Dowex Na$^+$ exchange column and the sodium salt 5 (kf53) was formed (Scheme 3, checked by $^1$H, $^{31}$P, NMR—all phosphorus moieties absorbed from −7 to −14 ppm at a pH 6-7, see FIG. 7, spectrum 1b for the $^{31}$P NMR spectrum of compound 5 (kf53)).

On the other hand, compound 6 (kf22) has been synthesized from the IHP octa N,N-dimethylcyclohexylammonium salt 7 (kf36A), with excess of benzoic anhydride in refluxing acetonitrile for 24 h, while the Na salt was derived from ion exchange of the mother compound after passing through a Dowex Na$^+$ exchange resin column to give product 5 (kf31) (Scheme 3, checked by $^1$H, $^{31}$P, NMR—all phosphorus moieties absorbed from −7 to −14 ppm at a pH 6-7, see FIG. 7, spectrum 1c for the $^{31}$P NMR spectrum of compound kf31). The pyrophosphate nature of the latter product 5 (kf31) was also revealed, when the pH was adjusted to 10 with addition of 5 M NaOH (see FIG. 7, spectrum 1d for the $^{31}$P NMR spectrum of compound kf31A in pH 10).

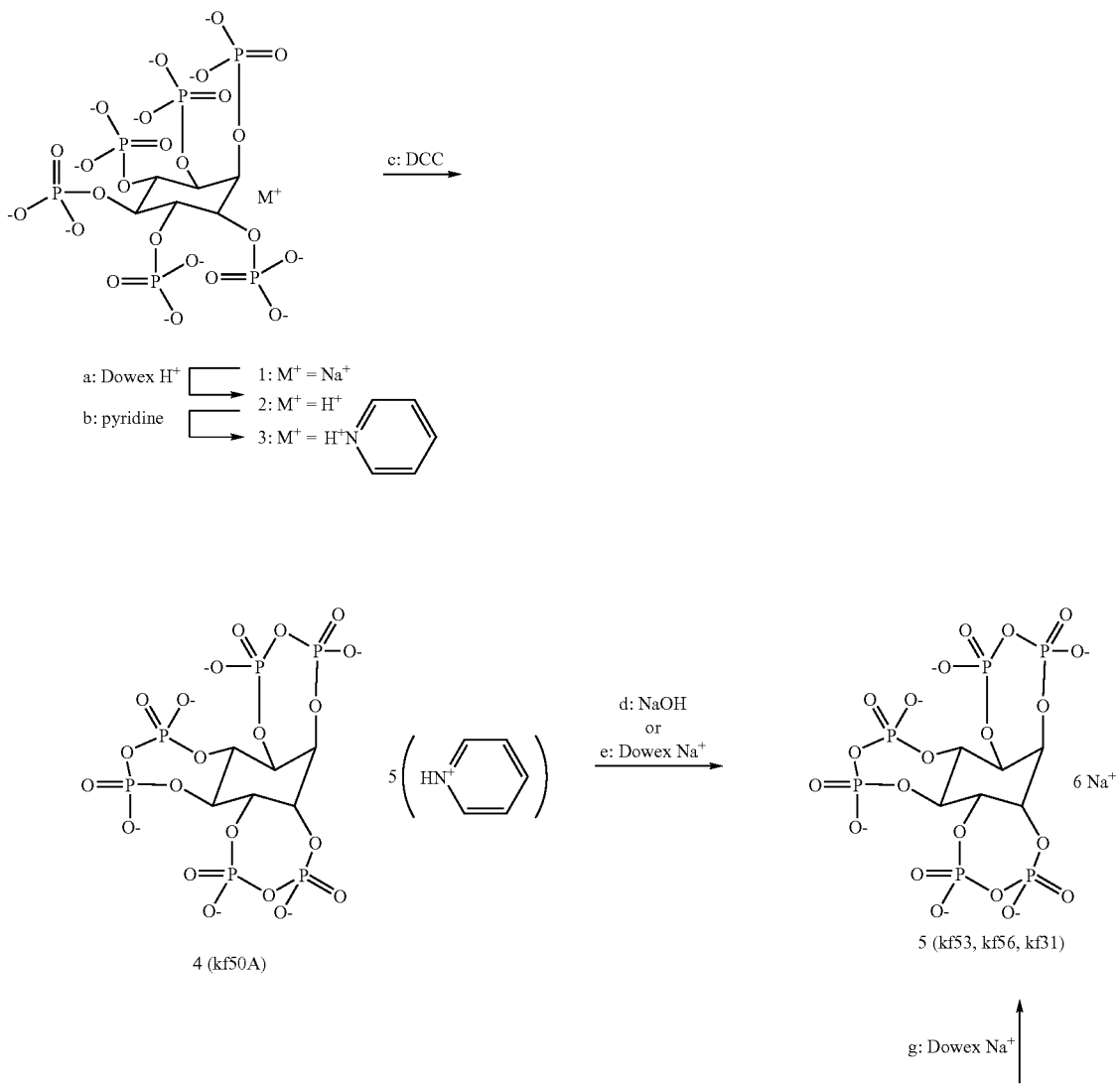

Scheme 3.
The ITPP Na salts formation.

-continued

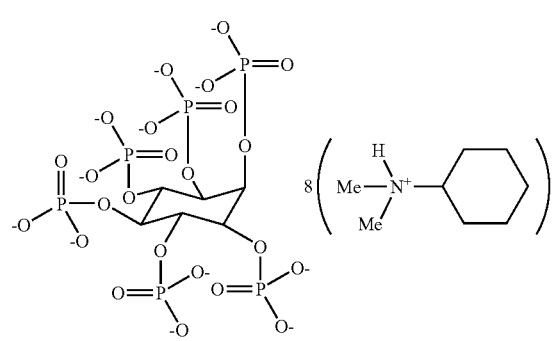

7 (kf36A)

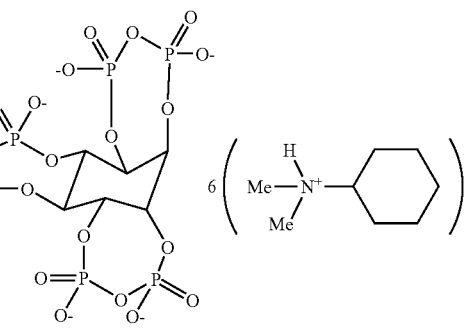

6 (kf22)

Samples of all batches of compound 5 (kf31, kf53 and kf56) were mixed together and a mixed $^{31}$P NMR was run at pH 10, (see FIG. 8, spectrum 2a). Both $^1$H and $^{31}$P spectra of compounds kf31, kf53 and kf56 as well as of their mixture were found identical. The fact that the chemical shifts of the compounds were insensitive to pH 6-10 suggests that all the phosphates were esterified.

Furthermore, a 2D $^{31}$P NMR COSY experiment of compound kf53 was performed, FIG. 8, spectrum 2b, showing a near classical pattern of three pairs of AB systems, with a strong correlation between the doublets with centers at −8.40 and −13.19 ppm and J=21.2 Hz, and a correlation between the doublets with centers at −9.58 and −9.71 ppm and J=17.8 Hz. This exhibits another proof that pyrophosphates are present in the molecule.

The synthesis of the pyrophosphates with DCC is explained with the mechanistic scheme shown in Scheme 4, while the mechanistic scheme for the reaction with acyl anhydrides and formates had been shown in Scheme 2.

was a trivial reaction in phosphate chemistry, DPG was exposed to the same conditions as with IHP, i.e. heating with an excess of acyl anhydride. Interestingly, no sign of pyrophosphate CPPG was found in the reaction mixture. The difference between DPG and IHP in the behavior towards acyl anhydrides is that DPG can have a free rotation around the bond connecting the two phosphate moieties, Scheme 5. This allows the two highly charged groups to adopt a conformation where the two phosphates are far away from each, thus promoting substitution rather than cyclization. Contrastly, in the case of IHP, the six member carbocyclic ring forces the phosphates to stay in a close proximity. When a good leaving group is attached on one of the phosphates, the vicinal phosphate group attacks, and with elimination of the inserted group, the pyrophosphate is formed and the molecule is more stable energetically.

Scheme 4.
Mechanistic pathways of the formation of pyrophosphate through a reaction with DCC.

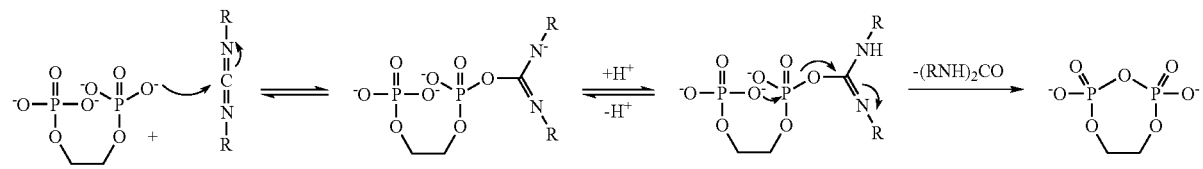

It is believed that the mechanism of Scheme 2 corresponding to formation of pyrophosphate upon reaction with acyl anhydrides under the conditions presented herein is not presented in the literature. N. Li, R. F. Pratt, *J. Am. Chem. Soc.,* 1998, 120, 4264-4268; M. Ahlmark, J. Versäläinen, H. Taipale, R. Niemi, T. Järvien, *J. Med. Chem.,* 1999, 42, 1473-1476. Under different conditions the synthesis of linear pyrophosphates to some extent was demonstrated, but such a formation was not observed here. H. G. Khorana, J. P. Vizsoyi, *J. Am. Chem. Soc.,* 1959, 81, 4660. In one example, a 7 membered pyrophosphate ring of 1,4,5 myo-inositol triphosphate was formed as a byproduct in a sequence of reactions where acetic anhydride was involved. S. Ozaki, Y. Kondo, N. Shiotani, T. Ogasawara, Y. Watanabe, *J. Chem. Soc. Perkin Trans.* 1, 1992, 729-737. In order to investigate whether this Scheme 5.
Explanation of the behaviour of DPG and IHP toward acyl anhydrides.

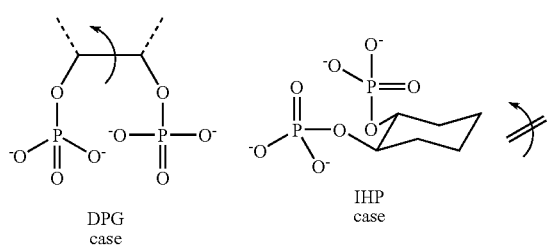

DPG case

IHP case

The orientation of IHP is such that pyrophosphates can form even without heating. In two control experiments, IHP octa N,N-dimethyl-cyclohexylammonium salt, 7 (kf36A), reacted with $Ac_2O$ (6 equiv in $CH_2Cl_2$ at rt for 4 days). The $^{31}P$ NMR showed a very complex mixture due to the uncompleted reaction but the doublets of the pyrophosphates were clearly observed. The other control experiment consisted of a reaction of the IHP octa N,N-dimethylcyclohexylammonium salt, 7 (kf36A), with DCC in $CH_2Cl_2$ at rt for 17 h. The reaction was also not completed but again the pyrophosphate doublets were detected. The same behavior of IHP was observed in the reactions with triphosgene and formates.

VI. Synthesis of Inositol Tripyrophosphate (ITPP) Ammonium Salts from Phytic Acid and ITPP Pyridinium Salt The synthesis of ITPP derivatives through the two routes shown in Scheme 6 were investigated. The first approach, Route A, led to the final ITPP compound III following the pathway 1 to 2 to IV to III, while the second one, Route B, was according to the pathway 1 to 2 to 4 to 8 to III.

Route A starts with compound 2, the perprotonated IHP molecule, and proceeds to the corresponding IHP compound IV. Compound IV bears the maximum of the counter cations they can hold. Compound IV was treated with DCC to give various results depending on the nature of the counter cation. For example, in the case of the N,N-dimethylcyclohexylammonium salt of compound IV, the reaction goes to almost completion. In the case of the n-hexylammonium-, cycloheptylammonium-, or cyclooctylammonium salts, 50% of the pyrophosphate product is hydrolyzed. The primary amine salt solutions are strongly basic (pH>10) and it is believed that the high basicity causes hydrolysis of the initially formed pyrophosphates. To address this problem compound IV bearing 6 or less counter cations were synthesized. Their reactions with DCC gave much better results, but not the desirable pure compounds, (except in the case of the tertiary ammonium salt). Furthermore, this route was more strenuous because each pyrophosphate had to be synthesized individually from its corresponding IHP ammonium salt in 3 steps. On the other hand, the more advanced compound 4 having the pyrophosphates already formed, could be used as a starting material for the construction of desired compounds III. Additionally, 4 can be synthesized in large quantities and in very clean form. These advantages prompted the investigation of alternative Route B.

Scheme 6.
General routes for the synthesis of ITPP ammonium salts

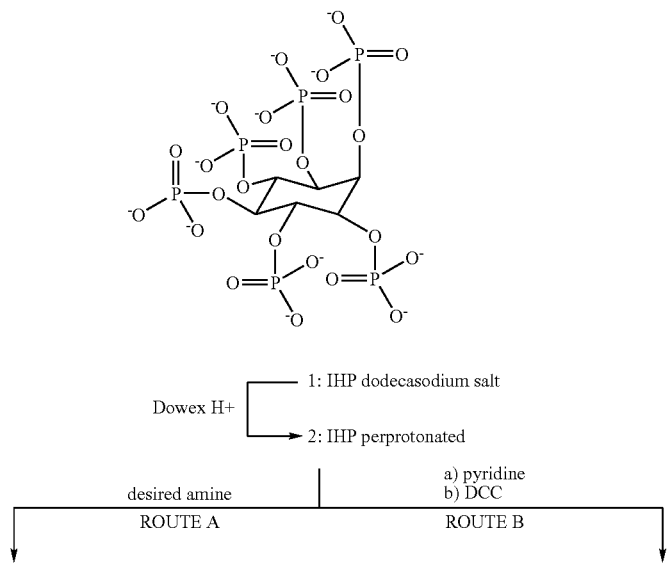

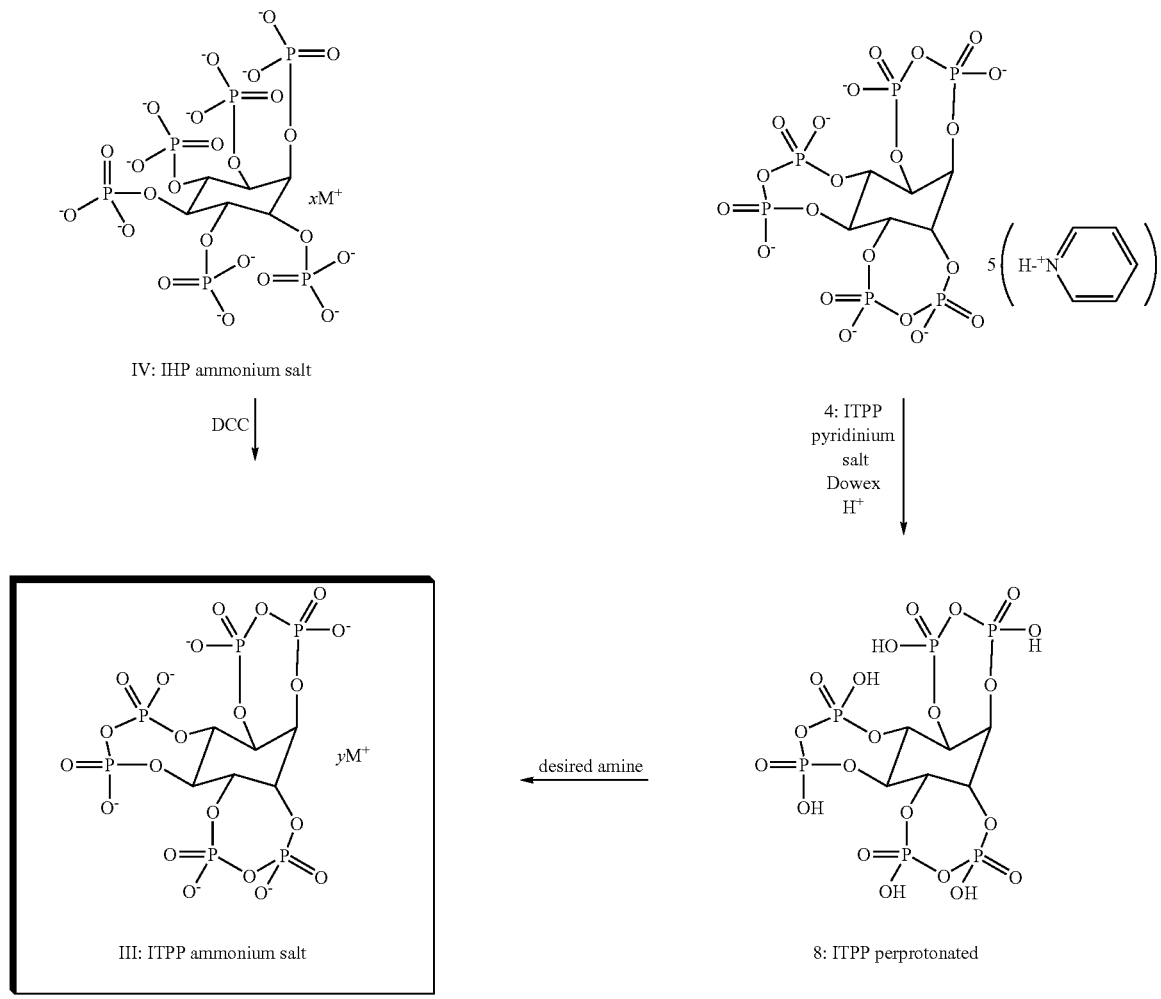

In Route B, the ITPP pyridinium salt 4 was synthesized according to the literature procedure and is shown in detail in Scheme 3. L. F. Johnson, M. E. Tate, *Can. J. Chem.,* 1969, 47, 63. The latter compound was passed through an ion exchange Dowex H$^+$ to give the perprotonated ITPP compound 8. Attempts to isolate this compound failed because pyrophosphates are very vulnerable to acidic conditions and hydrolyze to IHP. Thus, when an aqueous solution of 8 was concentrated by evaporation and reacted with the desired amine, part of the pyrophosphate was hydrolyzed giving mixtures of IHP and ITPP ammonium salts IV and III respectively. However, when the reaction was carried out immediately, with freshly prepared and non isolated perprotonated 8, the ITPP salts III were synthesized in excellent yields and in high purity.

General Route B has yielded 3 new ITPP salts of general structure III, bearing N,N-dimethylcyclohexylammonium (kf74), cycloheptylammonium (kf75) and cyclooctylammonium (kf76) counter cations (y=6). From the ITPP pyridinium salt 4 (kf50A) the Na salt 5 (kf77) was prepared in the way shown in Scheme 3. All five compounds were initially examined in vitro with free hemoglobin and whole blood.

VII. Solvent Effects on IHP-Acyloxy Carbonyl Formation vs. IHP-Pyrophosphate Formation According to the mechanism proposed in Scheme 2, the first step in forming an internal pyrophosphate ring is acyl phosphoester formation. This mechanism also applies to compounds comprising an alkyloxy carbonyl group. Experiments were carried out to determine what conditions favored the acyl or alkyloxy carbonyl intermediate versus internal pyrophosphate ring formation. The effect of solvent on internal pyrophosphate ring formation was determined for $CH_2Cl_2$/1,4-dioxane, $CH_3CN$, and $CH_3CN$/THF. The effect of these solvents during purification was also investigated, as well as the stability of the acyl phosphoesters in water.

IHP octa N,N-dimethyl-cyclohexylammonium salt 7, reacted with 1 equiv of RCOCl (R=cholesteryloxy) in a mixture of $CH_2Cl_2$ and 1,4-dioxane in a ratio 2.5/1 for 5 days to give, as was identified by mass spectroscopy, the corresponding cholesteryloxycarbonyl derivative, Scheme 7.

Scheme 7.
Synthesis of IHP-Cholesteryloxy carbonyl hepta
N,N-dimethyl-cyclohexyl-ammonium salt.

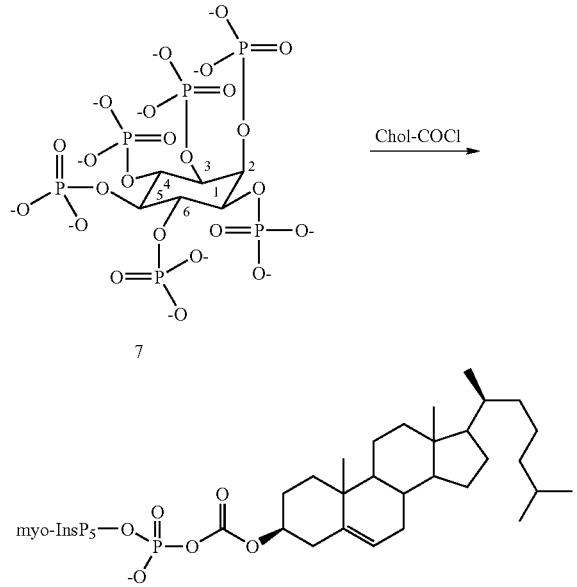

In all cases the $^{31}$P-NMR spectra of the crude compounds were found similar. However, they were all very complicated and could not be explained as having a mixture of the 4 isomeric derivatives or combinations of bis and/or mono cholesteryloxy carbonyl derivatives. FIG. 1 depicts a representative example of the $^{31}$P-NMR spectrum.

The spectra depict 3 bands of peaks. The first band covered the area 4 to −1 ppm, that is the part of the spectrum where the orthophosphates absorb. The second band covered the area −4 to −9 ppm, and the third one covered the area from −9 to −14 ppm. The last two bands were not found in the $^{31}$P-NMR of the starting material (IHP) and therefore, belong to the products of the reaction, meaning substituted phosphates. All reactions, after purification, showed an increase in intensity of the band −9 to −14 ppm at the expense of the band −4 to −9 ppm. This transformation is likely of compounds that appear in the latter band (probably the cholesterol derivatives) to compounds that absorb in the former band (internal pyrophosphate ring). Importantly, although 1 equivalent of cholesteryl chloroformate was used as reagent, a significant amount of cholesterol was always extracted during the purification procedures.

In a first series of experiments, the same reaction conditions as reported above (1 eq CholCOCl, CH$_2$Cl$_2$/1,4-dioxane at r.t. for 5 days) were carried out, but purification was carried out under various conditions, Table 1. Since there was pyrophosphate formed in the reaction, our task was at least to preserve the same amount of pyrophosphate but not to increase it. For the purification of the reactions from cholesterol, we initially extracted with CH$_2$Cl$_2$/H$_2$O. The system was forming a milky suspension and the two phases were not easily separated. At the end of the procedure, $^{31}$P-NMR showed that all peaks had moved into the −9 to −14 ppm area, indicating formation of the internal pyrophosphate ring. It was decided to use another bi-phase system, hexanes/MeOH. Cholesterol is well soluble in hexanes and IHP compounds are well soluble in MeOH. By heating at 50° C., the two phases were completely mixed in one phase. After cooling when the two phases were reseparated, the cholesterol had transferred into the hexanes phase more efficiently. The result of this purification method, however, was the same as with CH$_2$Cl$_2$/1,4-dioxane.

More success was obtained with purifying the materials with non-protic solvents, like hexanes, or hexanes in a mixture with some CH$_2$Cl$_2$ and/or centrifugion of the mixtures, but still we were not able to retain the amount of the pyrophosphate at least at the initial portions.

TABLE 1

Synthesis of IHP Cholesteryloxy carbonyl derivatives in CH$_2$Cl$_2$/1,4-dioxane, and purification trials.

| Sample Name | Reaction Conditions | pyrophosphate before purification | Purification Conditions | Pyrophosphate after purification |
|---|---|---|---|---|
| kf16 | 1 eq CholCOCl CH$_2$Cl$_2$/1,4-dioxane 2.5/1 (0.017M to IHP salt) | + | Extraction CH$_2$Cl$_2$/H$_2$O | +++ |
| kf16a3 | 1 eq CholCOCl CH$_2$Cl$_2$/1,4-dioxane 2.5/1 (0.017M to IHP salt) | + | Extraction hexanes/MeOH heat 50° C., cool and separation | +++ |
| kf16.3 | 1 eq CholCOCl CH$_2$Cl$_2$/1,4-dioxane 2.5/1 (0.017M to IHP salt) | + | Wash with hex, hex/CH$_2$Cl$_2$ | ++ |
| kf16.4 | 1 eq CholCOCl CH$_2$Cl$_2$/1,4-dioxane 2.5/1 (0.017M to IHP salt) | + | Wash with hex, hex/CH$_2$Cl$_2$ 9/1 | ++ |
| kf49 | 1 eq CholCOCl CH$_2$Cl$_2$/1,4-dioxane 2.5/1 (0.017M to IHP salt) | +/+++ | Wash with hex, hex/CH$_2$Cl$_2$ 9/1 centrifugion | ++++ |
| kf96 | 1 eq CholCOCl CH$_2$Cl$_2$/1,4-dioxane 2.5/1 (0.017M to IHP salt) | + | Wash with hex, hex/CH$_2$Cl$_2$ 9/1 centrifugion | ++ |

Interestingly, we found out, that samples kept in sealed vials-under air, were changing composition after a period of some weeks, giving more pyrophosphate.

In Table 2, we see the effect of the reaction time on the side pyrophosphate reaction using our classical conditions, as well as a synthesis using a different solvent. It was obvious from reactions kf16, kf16a3, kf16.3, kf16.4, kf49, and kf96 that by increasing the reaction time from 1 day to 3 days, the amount of the pyrophosphate was increased as well. By changing the solvent from CH$_2$Cl$_2$/1,4-dioxane to CH$_3$CN (kf83) we realized for the first time a very clean reaction, although uncompleted in 22 h, because cholesteryl chloroformate was not very well soluble in CH$_3$CN.

TABLE 2

Synthesis of IHP Cholesteryloxy carbonyl derivatives under various conditions with 1 equivalent of cholesteryl chloroformate.

| Sample Name | Reaction Conditions | Pyrophosphate |
|---|---|---|
| kf81A | 1 eq CholCOCl CH$_2$Cl$_2$/1,4-dioxane 2.5/1 (0.017M to IHP salt) 1 day | + |

TABLE 2-continued

Synthesis of IHP Cholesteryloxy carbonyl derivatives under various conditions with 1 equivalent of cholesteryl chloroformate.

| Sample Name | Reaction Conditions | Pyrophosphate |
|---|---|---|
| kf81B | 1 eq CholCOCl<br>$CH_2Cl_2$/1,4-dioxane<br>2.5/1<br>(0.017M to IHP salt)<br>2 days | ++ |
| kf81C | 1 eq CholCOCl<br>$CH_2Cl_2$/1,4-dioxane<br>2.5/1<br>(0.017M to IHP salt)<br>3 days | +++ |
| kf83 | 1 eq. Chol.<br>$CH_3CN$, 22 h | − |

However, by using a combination of THF, which dissolves the cholesterol reagent well, and $CH_3CN$, which dissolves the IHP starting material well, we were able to have again a clean reaction, kf88. Unfortunately, although kf88 was free of pyrophosphate, some was created during the purification using the best conditions found at that moment. The concentration of the reaction in such dilute conditions is not important since kf91 also gave the same good results. As it was expected, the reaction time proved once again critical (kf99). See Table 3.

TABLE 3

Synthesis of IHP cholesteryloxycarbonyl derivatives in THF/$CH_3CN$.

| Sample Name | Reaction Conditions | Pyrophosphate before purification | Purification Conditions | Pyrophosphate after purification |
|---|---|---|---|---|
| kf88 | 1 eq of Chol<br>THF:$CH_3CN$ 1:1<br>22 h<br>(0.012M to IHP) | − | Washings with hexanes and hexanes/$CH_2Cl_2$ 9/1, centrifugation | + |
| kf91 | 1 eq of Chol<br>THF:$CH_3CN$ 1:1<br>22 h<br>(0.024M to IHP) | − | none | − |
| kf99 | 1 eq of Chol<br>THF:$CH_3CN$ 1:1<br>22 h<br>3 days | ++ | none | − |

Finally, the results of changing the number of equivalents of cholesteryl chloroformate are presented in Table 4.

TABLE 4

Synthesis of IHP cholesteryl derivatives under THF/$CH_3CN$ conditions with 1.5 and 2 equivalents of cholesterol chloroformate, and purification trials.

| Sample Name | Reaction Conditions | Pyrophosphate before purification | Purification conditions | Pyrophosphate after purification |
|---|---|---|---|---|
| kf89 | 1.5 eq Chol<br>THF:$CH_3CN$ 1:1<br>22 h<br>(0.012M IHP) | − | Wash with hexanes,<br>Hexanes/$CH_2Cl_2$ 9/1 centrifugation | + |
| kf92 | Same as kf89<br>(0.024M IHP) | − | None | |
| kf92p | Same as kf92 | − | Wash with hexanes,<br>hexanes/THF 9/1 Centrifugation | − |
| kf100 | Same as kf92<br>3 days | ++ | None | |
| kf90 | 2 eq Chol<br>THF:$CH_3CN$ 1:1<br>22 h<br>(0.012M IHP) | − | Wash with hexanes,<br>hexanes/$CH_2Cl_2$ 9/1 Centrifugation | + |
| kf93 | Same as kf90<br>(0.024M IHP) | − | None | |
| kf93p | Same as kf93 | − | Wash with hexanes,<br>hexanes/THF 9/1 Centrifugation | − |
| kf101 | Same as kf93 | ++ | None | |

For reaction kf89 1.5 equiv of cholesteryl chloroformate was used. According to the integration values of the $^{31}$P-NMR spectrum, in 22 h statistically 1 cholesterol moiety was attached on IHP. The reaction was not forced to proceed for a longer period of time. Although the concentration of the reaction mixture in these dilute conditions had no effect (see reaction kf92), the increase of the reaction time was acting against the cholesterol derivatives (see reaction kf100). Reactions kf90, kf93, kf93p, and kf101 represent analogous reactions using 2 eq of cholesteryl chloroformate.

When purification of kf89 and kf90 was attempted, pyrophosphates formed like in case kf88. In all experiments using $CH_2Cl_2$, pyrophosphates formed either in the reaction and/or in the purification. It is possible then, that $CH_2Cl_2$ accelerates the rate of pyrophosphate formation. Indeed, when THF was used in the purification step instead of $CH_2Cl_2$, pyrophosphate formation was avoided, and we were able to purify the already pyrophosphate free products. The conclusion of the experiments described above is that alkyloxy carbonyl and acyl derivatives of IHP are relatively stable in organic solvents.

After completing the optimization and purification conditions, it was time to check the behavior of the purified compounds in water. Based on the stability that ATP cholesteryloxy carbonyl derivatives display in water, it was assumed that the alkyloxy carbonyl IHP derivatives would behave similarly. Because the biological applications of the present invention take place in water and in neutral pH, these parameters had to be considered as well.

Figure 2:
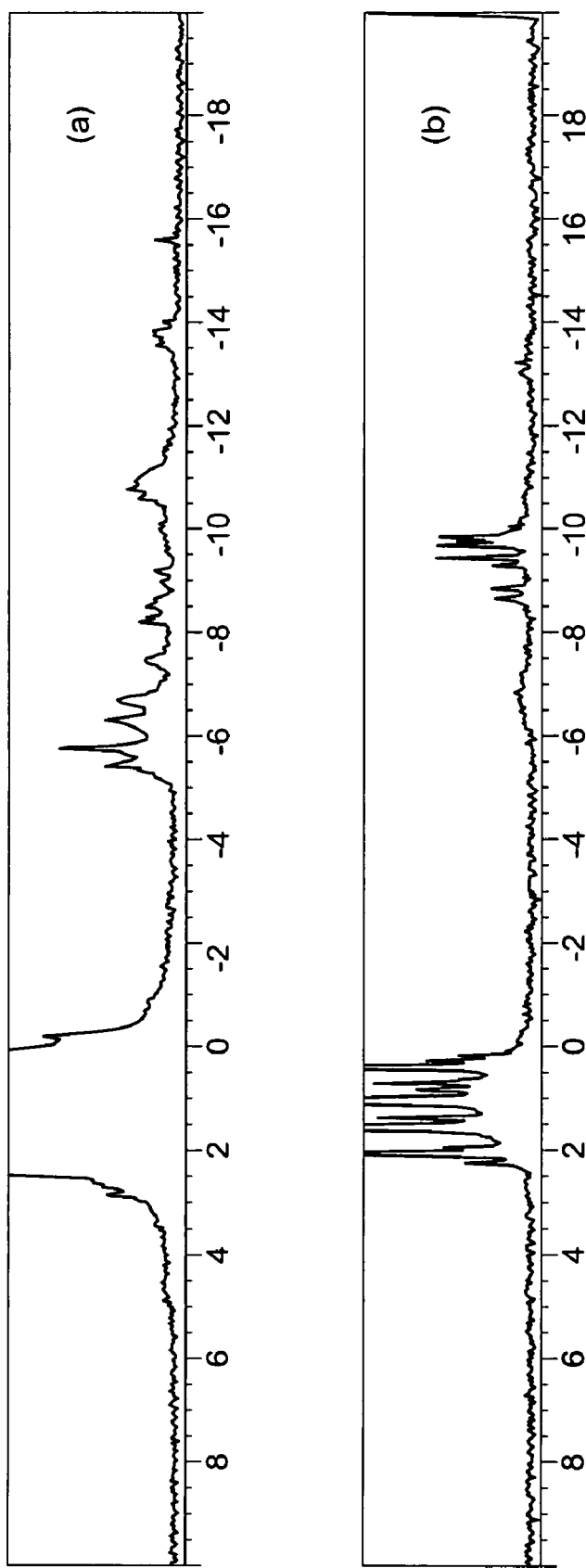
FIG. 2 depicts the crude and purified $^{31}$P NMR spectra of IHP-cholesteryloxy carbonyl in various deuterated solvents.

FIG. 2 depicts (a) the $^{31}$P NMR spectrum of the compound from kf96 in $CDCl_3$, and (b) the same purified compound in $D_2O$.

Figure 3:
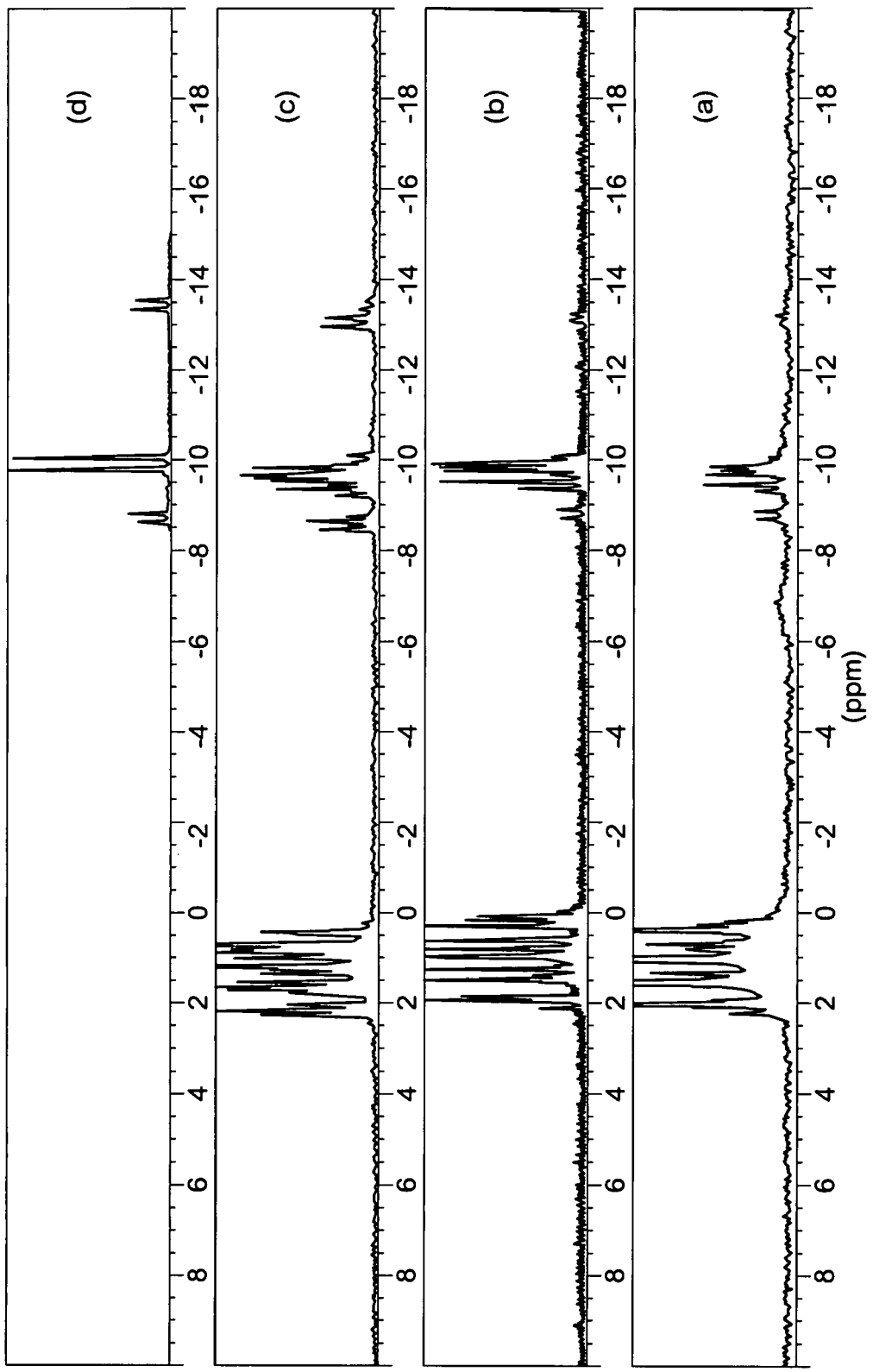
FIG. 3 depicts the $^{31}$P NMR spectrum of purified IHP-cholesteryloxy carbonyl; the $^{31}$P NMR spectrum of highly purified IHP-cholesteryloxy carbonyl; the $^{31}$P NMR spectrum of IHP-monopyrophosphate ("IMPP"); and the $^{31}$P NMR spectrum of ITPP.

The difference observed in the absorption and the shape of the peaks was due to the $D_2O$. Interestingly, the spectrum of kf96 appeared less complex in $D_2O$. The characteristic doublets of the pyrophosphates were clearly detected, but the absence of peaks in the area at −4 to −8 ppm was puzzling. The IHP monopyrophosphate was synthesized through a reaction of IHP octa N,N-dimethyl-cyclohexylammonium salt 7 with 1 equivalent of DCC (vide infra), and its spectrum is given in FIG. 3(c). Despite the fact that the spectra were complex due to the non selective formation of the pyrophosphates, they were all quite similar and closely related to the ITPP N,N-dimethyl-cyclohexylammonium salt in $D_2O$ (FIG. 3(d)), as it is shown from the comparison of spectra (a), (b) and (c) with (d). See FIG. 3.

Therefore, we concluded that IHP alkyloxy carbonyl derivatives are quite unstable in water. They hydrolyse immediately either to pyrophosphate through an intramolecular attack from a neighboring phosphate, or to orthophosphate through an intermolecular attack from water. (The latter transformation was hypothesized due to the loss of the 5:1 ratio of the integration between orthophosphates and pyrophosphates in the spectra). This observation also explained, why prolonged storage in air was changing the composition of the highly hygroscopic cholesteryloxycarbonyl compounds like kf49 in Table 1.

VIII. Synthesis of IHP Monopyrophosphate (IMPP)

Further experimentation led to control over the number of internal pyrophosphate rings formed. The synthesis of IHP-monopyrophosphate was carried out using 1 equivalent of DCC (as activator of the phosphates) with 1 equivalent of IHP octa N,N-dimethyl-cyclohexyl ammonium salt in a refluxing mixture of $CH_3CN/H_2O$ in a 2/1 ratio. See Scheme 8.

Scheme 8.
Synthesis of hexa N,N-dimethylcyclohexylammonium salts of IHP monopyrophosphates.

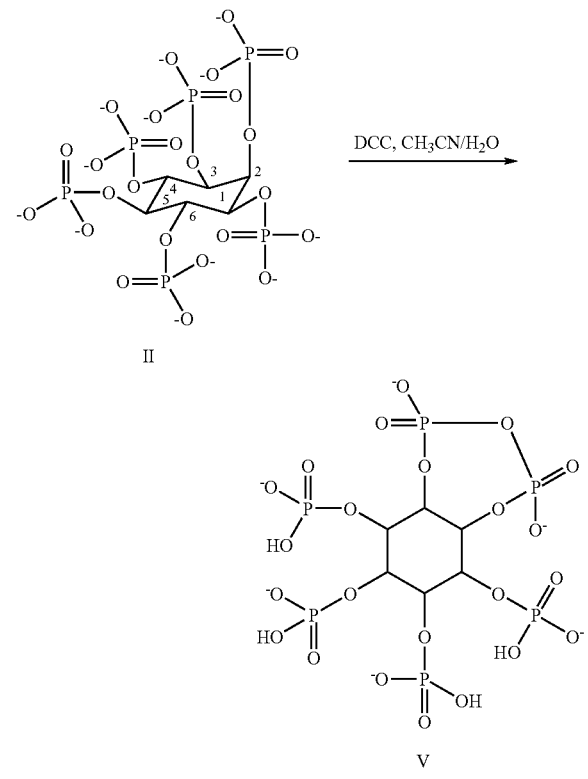

The synthesis is not selective, as it was revealed by the $^{31}P$ NMR, see FIG. 3(c), because all 6 phosphates of IHP have similar reactivity. Compound V passed through a Dowex $Na^+$ exchange resin column to give the corresponding $Na^+$ salt. As will be seen in the following section, biologically active mixtures of the present compounds contain all possible isomeric pyrophosphates if IHP. Therefore, tripyrophosphates of IHP (ITPP) are advantageous because they are well defined compounds and can be synthesized in high purity. ITPP compounds prepared thus far have as their counterions N,N-dimethylcyclohexyl ammonium, pyridinium, cycloheptylammonium, cyclooctylammonium, or sodium.

IX. Detecting the acyl-IHP Derivative Intermediate

The reactions of IHP with acyl anhydrides was investigated further in light of both a) the optimization of the cholesteryloxy carbonyl IHP derivative synthesis and its behavior in both aqueous and organic solutions, and b) the ability to control the competitive pyrophosphate reaction in organic solutions. A careful study of the spectra of earlier experiments, revealed that acyl moieties do attach to IHP. However, before completely optimizing the reactions, their stability in aqueous solutions and in neutral pH had to be examined.

The use of $CH_2Cl_2$ was avoided for reasons explained before. Instead, we examined the reactions of IHP with 1-3 equivalents of $Ac_2O$, $Bz_2O$ and hexanoic anhydride in either $CH_3CN$ or a mixture of $CH_3CN/THF$. The $CH_3CN/THF$ solvent system was superior because it gave more loading of acyls on IHP in the same amount of time. No pyrophosphates formed in all cases using these solvents.

Figure 4:
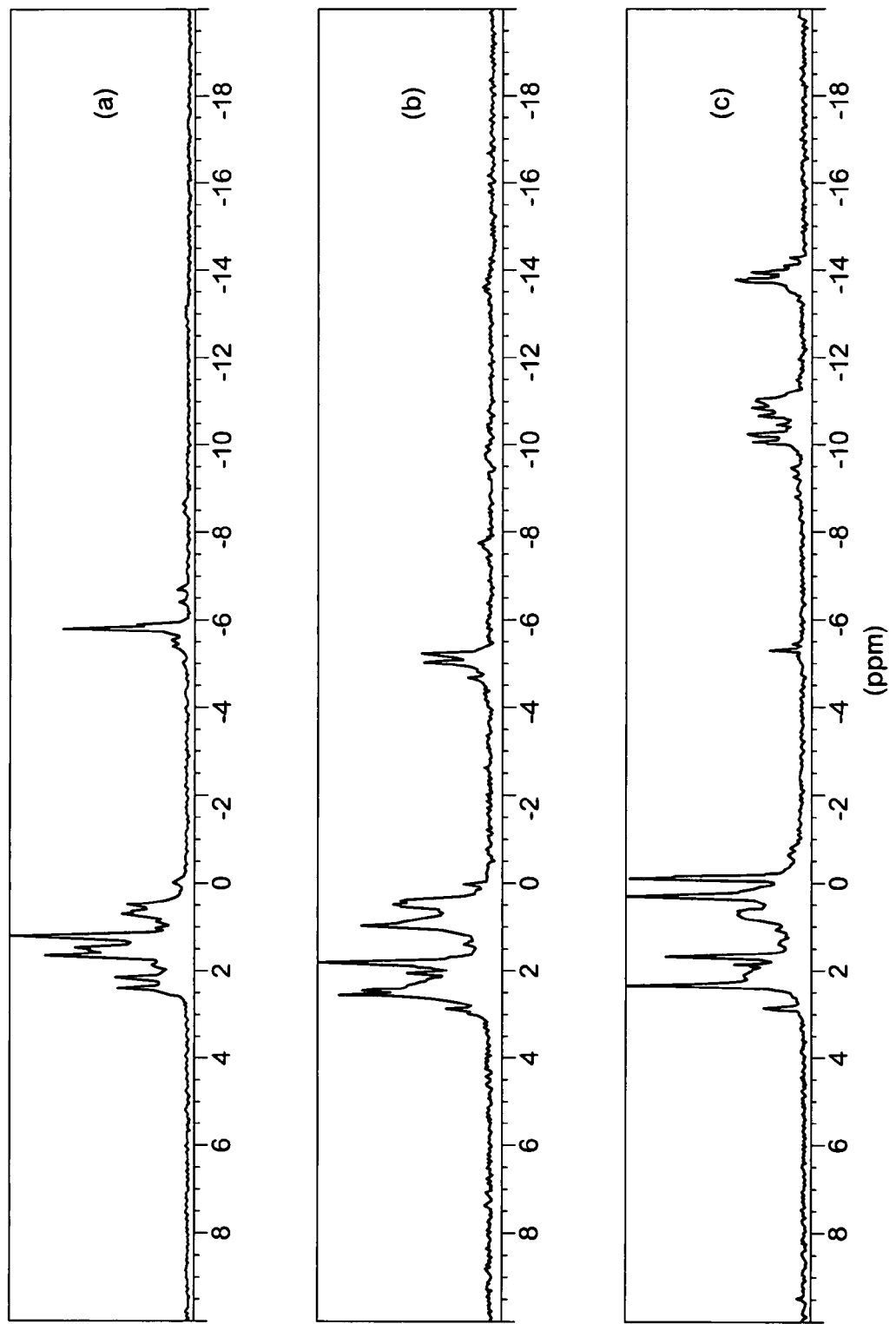
FIG. 4 depicts the $^{31}$P NMR spectra of IHP-benzoate in different solvents and the $^{31}$P NMR spectrum of IHP-benzoate after heating.

A benzoate derivative, kf105, see FIG. 10, compound E for a general structure, synthesized upon a reaction of IHP octa N,N-dimethyl-cyclohexylammonium salt with 2 equiv of $Bz_2O$ in a mixture of $CH_3CN/THF$ at r.t for 24 h, gave after concentrating the solvents a crude material. The $^{31}P$-NMR of kf105 in $CDCl_3$ is shown in FIG. 4(a). The absorption of the phosphorous peaks at −6 ppm indicates a benzoate substitution, since there was no phosphorous observed in the area of −8 to −14 ppm. For the same crude material we performed a $^{31}P$-NMR spectrum in $D_2O$ as shown in FIG. 4(b). Phosphorous absorption in the area around −5 ppm was retained which means the compound is stable in water. Finally, in order to prove that indeed we have a benzoate covalently attached on IHP, and that the formation of the pyrophosphate happens through an attack of a nearby phosphate according to mechanisms we proposed, we heated the material in $CH_3CN$ for 6 h. As was expected, we observed formation of pyrophosphates (area −9 to −14 ppm, FIG. 4(c)). The latter experiment showed that this phosphate benzoate mixed anhydride was quite stable, since after 6 h of heating its transformation to the pyrophosphate was not thoroughly completed.

Figure 5:
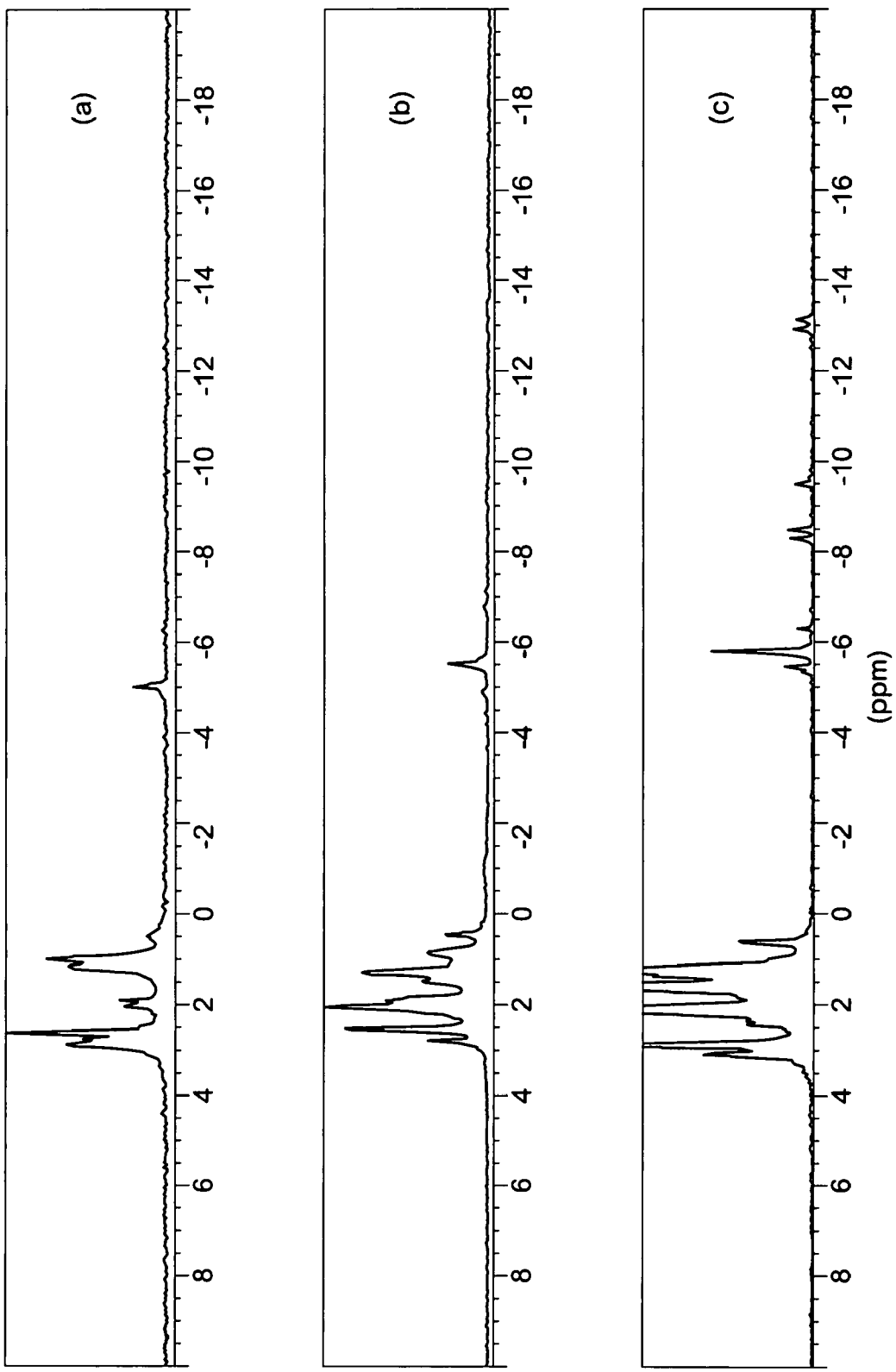
FIG. 5 depicts the $^{31}$P NMR spectrum of crude IHP-benzoate; the $^{31}$P NMR spectrum of purified IHP-benzoate; and the $^{31}$P NMR spectrum of IHP-benzoate at pH 6.9.

The next task was to determine if these compounds could tolerate concentration in water and an increase in pH. To investigate these parameters, another pilot experiment kf104, was carried out as follows: IHP octa N,N-dimethyl-cyclohexylammonium salt was reacted with 1 equiv of $Bz_2O$ in a mixture of $CH_3CN/THF$ at r.t for 24 h. This reaction gave after concentration of the solvents a crude material, the $^{31}P$-NMR of which in $CDCl_3$ is shown in FIG. 5(a). Comparing the spectra in FIG. 4(a) and FIG. 5(a) we see that using 1 equiv of $Bz_2O$ had significantly less loading of the benzoate (only approximately 20% of the reagent had reacted in 24 h). The product was purified by extracting several times with toluene and $H_2O$ in order to remove excess reagent. The aqueous phase was concentrated by rotary evaporation at 45° C. The $^{31}P$-NMR spectrum of the compound in $CDCl_3$ is depicted in FIG. 5(b). There was no obvious change and the benzoate was still attached.

This material was redissolved in water and the pH of the solution was adjusted to 6.9 with 0.2M NaOH. The mixture was concentrated as before and this time the $^{31}$P-NMR showed the characteristic doublets of the pyrophosphate and 25% hydrolysis. See FIG. 5c. Hydrolysis to such a small extent under these harsh conditions shows that it is quite possible to prepare and study these prodrug anhydride derivatives.

Figure 6:
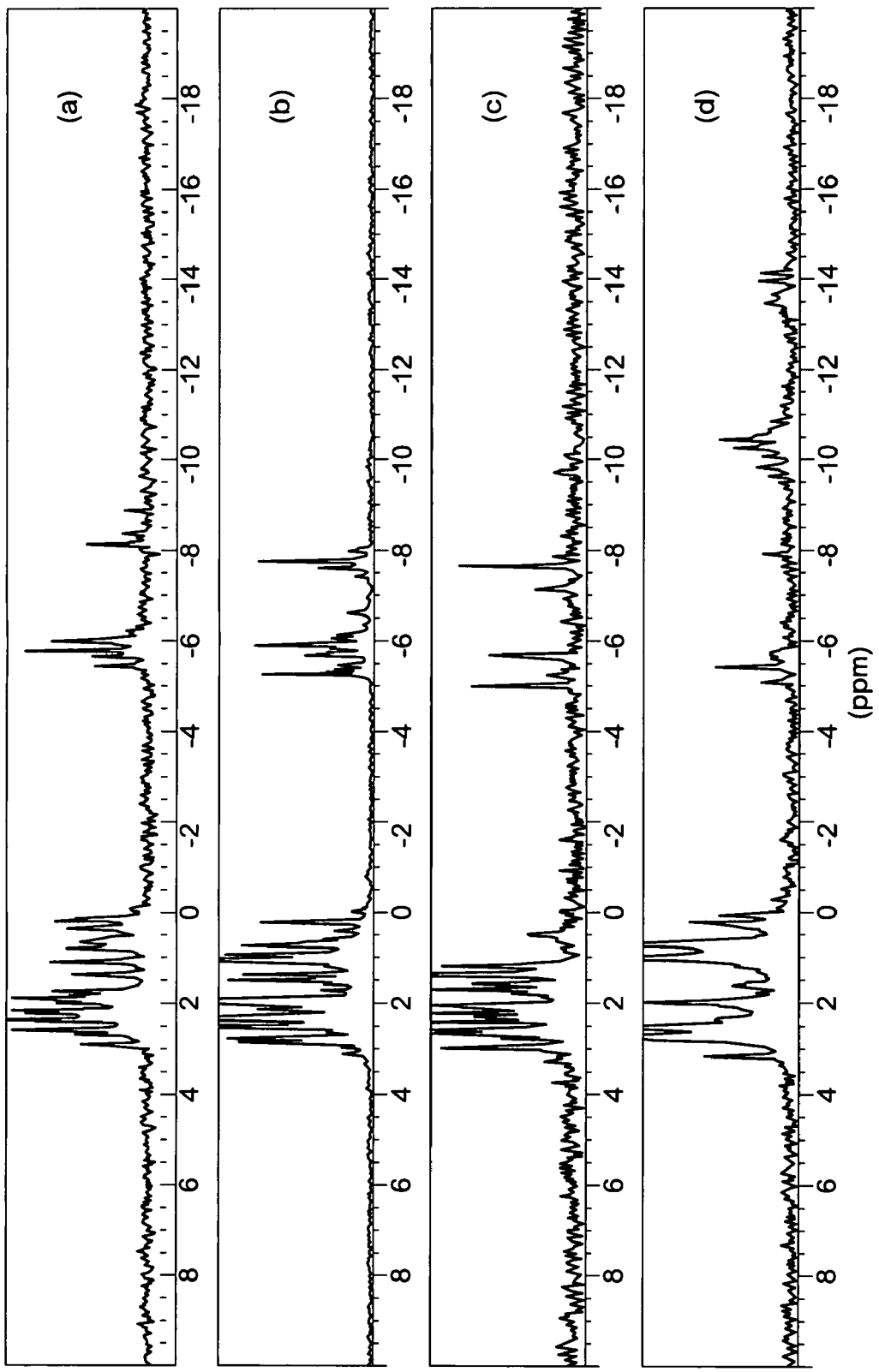
FIG. 6 depicts the $^{31}$P NMR spectrum of the crude IHP-hexanoyl derivative; the $^{31}$P NMR spectrum of the purified IHP-hexanoyl derivative; the $^{31}$P NMR spectrum of the IHP-hexanoyl derivative at pH 7.3; and the $^{31}$P NMR spectrum of the IHP-hexanoyl derivative after heating.

An n-hexanoyl derivative, see FIG. 10, compound E for a general structure, was prepared by reacting IHP octa N,N-dimethyl-cyclohexylammonium with 2 equiv of $(C_5H_{11}CO)_2O$ in $CH_3CN$ at r.t for 24 h. The $^{31}$P-NMR in $CDCl_3$ is shown in FIG. 6(a). The hexanoyl anhydride gave a higher loading than the benzoic anhydride (1 hexanoyl is statistically attached on IHP, according to the integration of the spectrum). The mixture was extracted with toluene and water and the aqueous phase was concentrated as before. In FIG. 6(b), we see that the phosphorous peaks cover a larger area of the spectrum, but still we don't see any evidence of pyrophosphate formation. It is believed that the broader coverage by the phosphorous peaks is due to migration of the hexanoyl moieties. Migration of acyl moieties is known in mediums of acidic pH, and probably leads to a less strained and more stable conformation for the molecule.

The material was redissolved in water and a solution of 0.2M NaOH was added slowly at 0° C. (not at r.t.) until the solution arrived at pH=7.3. The solution was not concentrated but was instead lyophilized. The $^{31}$P-NMR of the compound (still soluble in $CDCl_3$) is depicted in FIG. 6(c). No change was observed. The compound survived and remained intact throughout all manipulations. Additionally, it did so at the correct pH for the biological experiments.

In order to be sure that the distribution of the phosphates in the spectrum was not due to IHP transformations, the n-hexanoyl derivative was heated in refluxing $CH_3CN$ for 6 hours. It is clear from the $^{31}$P-NMR spectrum, (see FIG. 6(d)), that the acylated peaks disappeared and gave rise to pyrophosphate peaks. The reaction did not go to completion, showing that, as with the benzoate derivative, the phosphate acyl anhydrides are indeed quite stable compounds. This has been repeatedly demonstrated in the literature. N. Li, R. F. Pratt, *J. Am. Chem. Soc.*, 1998, 120, 4264-4268; M. Ahlmark, J. Versäläinen, H. Taipale, R. Niemi, T. Järvien, *J. Med. Chem.*, 1999, 42, 1473-1476.

X. Attempts for Further Derivatization of ITPP

The ability of ITPP to react further with acylating or other agents was investigated through three preliminary experiments. First, ITPP N,N-dimethylcyclohexyl ammonium salt was heated extensively with acyl anhydrides and no change was observed. The second experiment attempted to react ITPP pyridinium salt 9 with acyl anhydride in the presence of pyridine and DMAP, but solubility of the starting material in $CH_2Cl_2$ proved problematic. In the third experiment, a reaction with triphosgene (which was expected to exchange an OH with Cl) and subsequent reaction with cycloheptyl amine gave, after extraction of the reaction mixture with $H_2O$ and $CH_2Cl_2$ separately, phosphorous containing compounds in both phases (TLC, NMR). In the aqueous phase the ITPP cycloheptyl ammonium salt (instead of the pyridinium salt) was observed and in the organic phase a material absorbing in +10 ppm was observed which may be a fully substituted ITPP. Unfortunately this material is not soluble at all in water and therefore could not serve as a prodrug.

From these preliminary experiments it was concluded that the pyrophosphate's free hydroxyl group is inactivate but not inert. It is possible using the proper reagents to make ITPP even more lipophilic upon controlled substitutions and investigate the possibility of transporting these molecules into the erythrocytes.

XI. Hydrolysis of Pyrophosphates

Experiments designed to test IHP-pyrophosphate's resistance to chemical hydrolysis were conducted. ITPP N,N-dimethyl-cyclohexylammonium salt solutions were adjusted at pH 8.66, 10.20, 12.05 and 13.30. In order to avoid any damage to the NMR tubes due to the highly alkaline solutions, all samples were checked using $^{31}$P-NMR at different time intervals against an external $Ph_3PO/DMSO$ solution. This method also avoided concentrating the samples and redissolving them in a deuterated solvent, which may have led to changes in the results. No changes were observed after 3 days, except for pH=13.3 which showed 7% hydrolysis. Observing this stability, we exposed the pH=13.30 sample to heat at 60° C. for 6 h. The sample revealed a non selective hydrolysis of only 13%. After 22 h at the same temperature, hydrolysis was only 19%. Facing this extreme stability to chemical hydrolysis we concentrated to dryness both solutions of pH 10.20 and 13.30 and dissolved them in $D_2O$. Their NMR spectra showed that the sample at pH 10.20 remained unchanged, while the pH=13.30 sample completely converted to the IHP open form sodium salt, phytic acid.

XII. Enzymatic Hydrolysis of ITPP

ITPP was dissolved in a buffer solution of a pH 4.6 and heated in the presence of baker's yeast for 12 h at 45° C. Non selective hydrolysis of approximately 25% occurred.

XIII. Partition Coefficients of Pyrophosphates

Partition coefficients relate to the distribution of a solute between two immiscible liquid phases and are defined as the ratios of concentrations (or molar fraction) of the distributed solute. These data have been used to predict and rationalize numerous drug properties such as quantitative structure/activity relationship, lipophilicity, and pharmacokinetic characteristics. 1-Octanol has been found to properly mimic biological membranes, and it has been estimated that 1-octanol/water ($K_{ow}$) partition coefficients of more than 18000 substances are now available in the literature.

The partition coefficients for our compounds, $K_{ow}=[ITPP]_{1-octanol}/[ITPP]_{water}$, were measured after equilibration at a concentration of 30 mM, close to the typical concentration employed for biological evaluations.

The IMPP hexa N,N-dimethyl-cyclohexylammonium compound and ITPP compounds where the cation is pyridinium, N,N-dimethyl-cyclohexylammonium, and $Na_+$ had $K_{ow}<10^{-3}$ and could not be measured using this method. Interestingly the cycloheptylammonium ITPP salt had $K_{ow}=0.0121$ and the cyclooctylammonium ITPP salt had $K_{ow}=0.462$. This behavior is in agreement with what has been observed for IHP cycloheptyl and cyclooctyl salts for their potential ability to transfer myo-inositol through cell membranes.

XIV. Partition Coefficients of Tripyrophosphate Na Salt as a Function of a Cyclooctylammonium Concentration It has previously been reported that cyclooctylammonium ions can transport phytic acid into an octanol phase. S. P.

Figure 9:
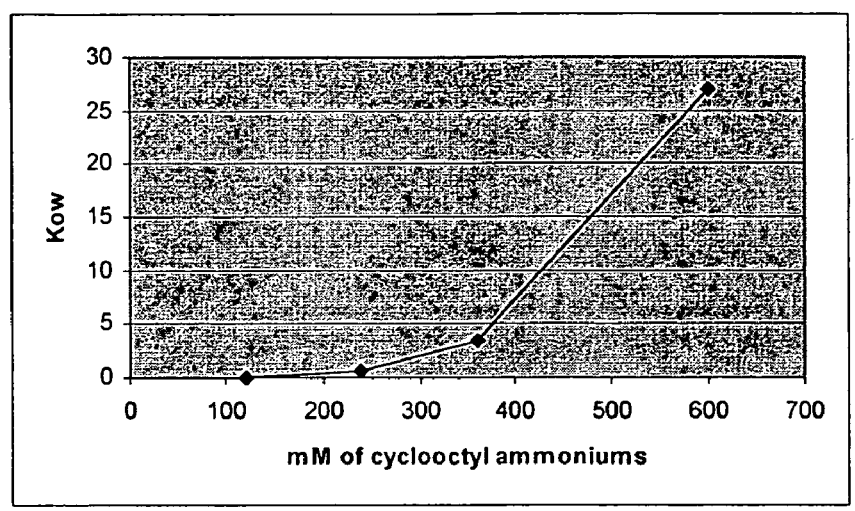
FIG. 9 depicts ITPP uptake in 1-octanol by cyclooctylammonium ions.
Figure 11:
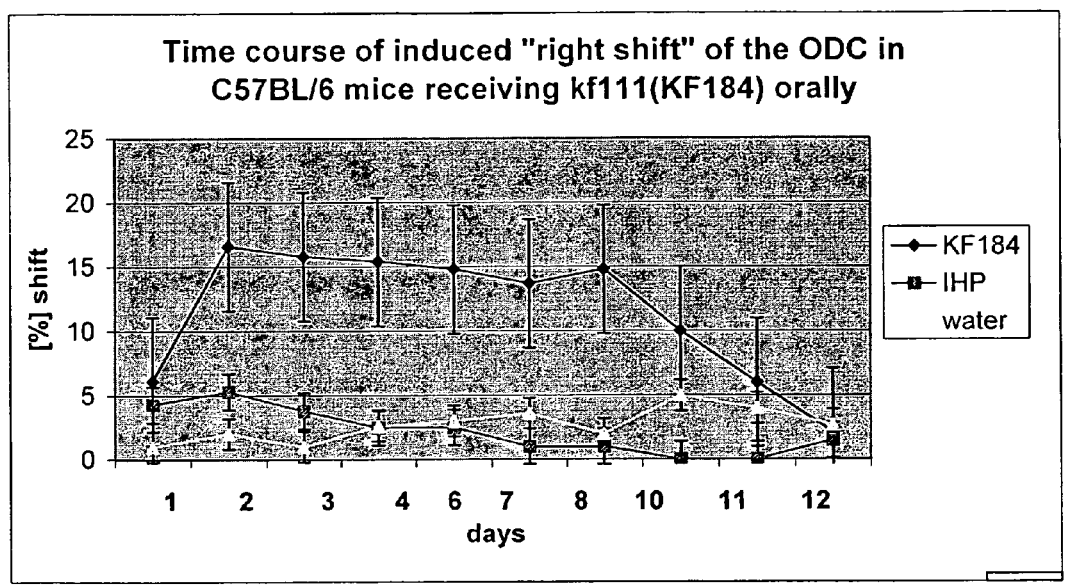
FIG. 11 depicts means of 12 $P_{50}$-values and standard deviation are shown. On day 4 the kf111-solution was replaced by water. $P_{50}$ values were measured over 12 days. Four mice received IHP in water, at the same concentration as kf111. On day 4 IHP was replaced by water. Three mice received only water during the 12 days.
Figure 12:
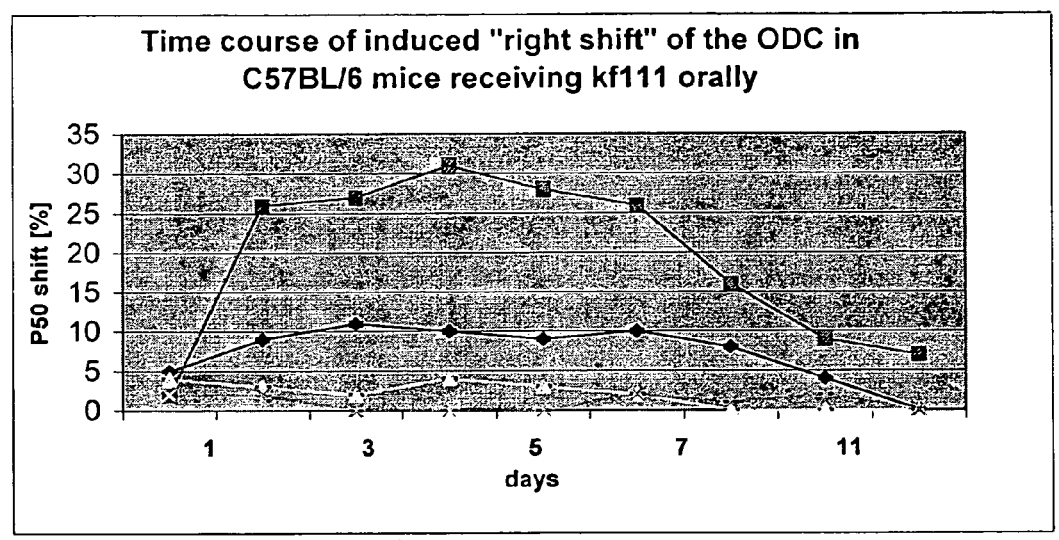
FIG. 12 depicts $P_{50}$ shifts of 4 single mice (and standard deviation are shown). Mouse 1, Mouse 12, IHP control mouse, water control mouse.
Figure 13:
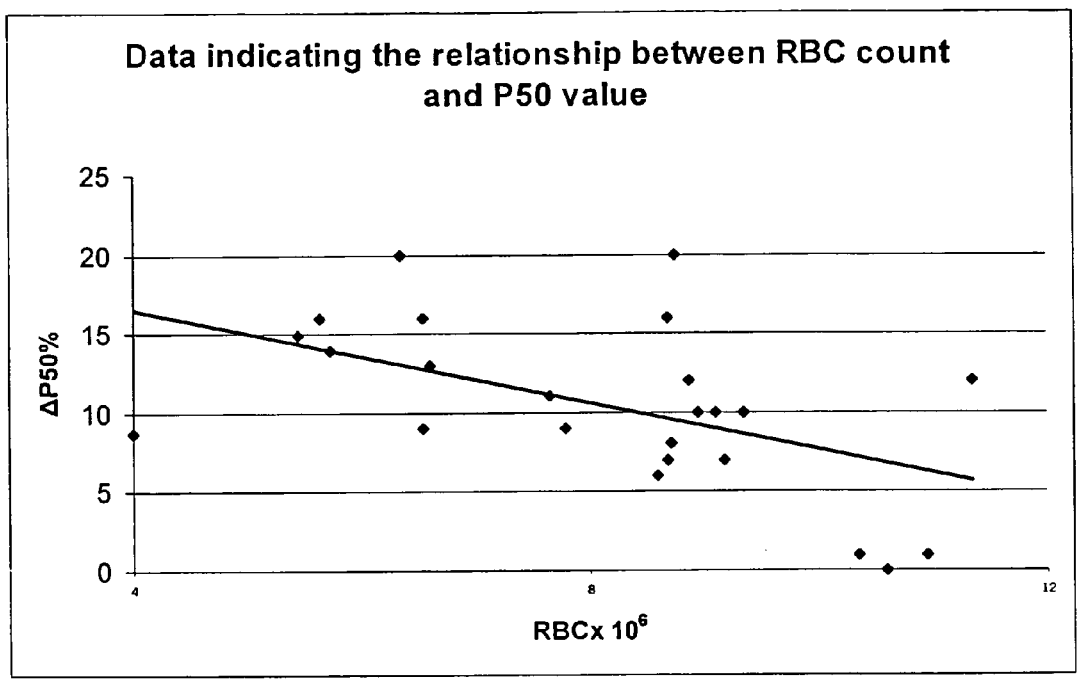
FIG. 13 depicts the relation of $P_{50}$ shift [%] to erythrocytes (values are taken from Table 1). Based upon the preliminary data reported that an inverse relationship exists between the number of RBC and shift of their $P_{50}$ value. The basal value of the RBC count is restored, once $\Delta P_{50}$ becomes 0%, 12 days after ingestion of kf111.

Vincent, Jean-Marie Lehn, J. Lazarte, C. Nicolau, *Bioorg. Med. Chem.*, 2002, 10, 2825-2834. See FIG. 9. At a constant concentration (22 mM) 8 equiv of cyclohexyl ammonium ions are required to reach a $K_{os}$ (in serum) value of 1, corresponding to an identical distribution between human serum and 1-octanol. Similar results were obtained with the Na salt of ITPP in a water/1-octanol system. Considering that PP values in serum were generally lower that the ones in water, it was concluded that the increased lipophilisity in ITPP (6 charges less than IHP) affects the transportation of the compound with cyclooctylammonoum salts. This means more equivalents of cyclooctylammoniums are needed in order to arrive at a $K_{ow}$ of 1. This property indicates the significant difference between the two compounds in terms of physical behaviour.

XV. Oral Administration of Tri-Pyrophosphates

The sodium salt of the tri-pyrophosphate derivative of IHP (kf111) was dissolved in drinking (not deionized) water at a 20 g/L-concentration (=27 mM) and offered for drinking ad libitum. As in all experiments performed before, pH was adjusted to ~7.0.

Twelve C57BL/6 mice drank kf111 over 4 days (about 25 ml/24 hrs). Three control mice drank either pure water, or a solution of IHP (inositol hexaphosphate) at the same concentration and pH as kf111 (4 mice). The amount of drunken fluid was the same when offering pure water, IHP-water or kf111-water, indicating that kf111-, or IHP-solution was not rejected by the mice. Blood was collected from the tail vein of the 19 C57BL/6 mice on day 0 (before treatment started), 1, 2, 4, 6, 7, 8, 10, 11 and 12, in order to measure $P_{50}$ values.

The following remarks can be made:
1. kf111 was not rejected by the mice apparently, when administered orally.
2. kf111 was not harmful to the animals when applied orally. No C57BL/6 mouse seemed to suffer by this treatment.
3. Oral application of kf111 caused significant right shifts of $P_{50}$ (up to 31%) in mice.

Figure 14:
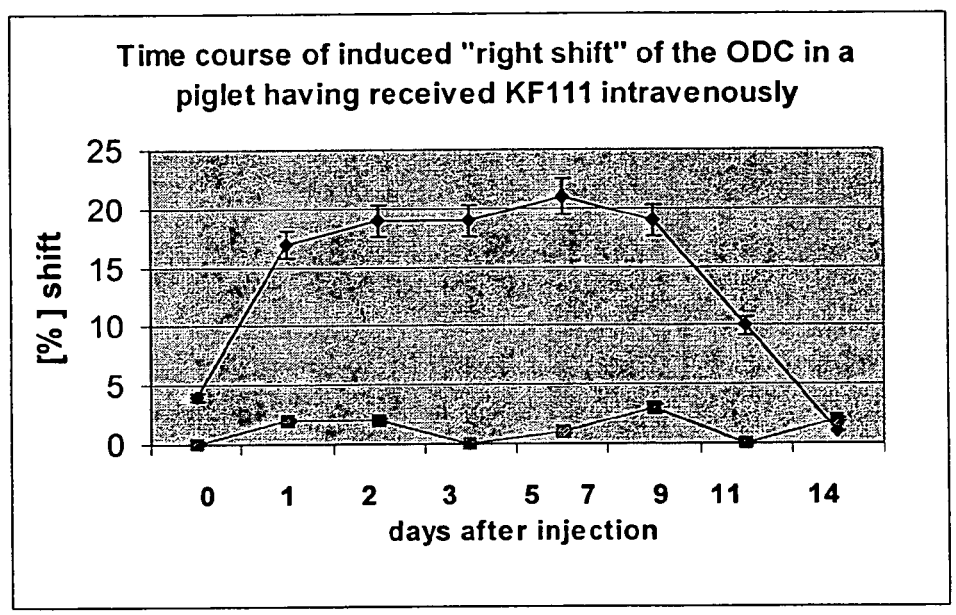
FIG. 14 depicts the $P_{50}$ shifts (means of 4 measurements) in blood from an injected, and a non injected piglet and standard deviations are shown. Value obtained on day 0=measurement 2.5 hrs after injection.

As described, the 19 C57BL/6 mice having received kf111 in water, IHP in water or pure water were observed over 12 days, the $P_{50}$ values of their circulating RBC were measured almost daily. FIG. 14 shows the time course of the induced right shift of the ODC (oxyhemoglobin dissociation curve) in the mice ingesting kf111 and the absence of shift in the control animals ingesting an aqueous solution of IHP or pure water.

It appears that all mice ingesting the aqueous solution of kf111 present a shift of the $P_{50}$ value of their circulating RBC, albeit with individual differences. None of the controls show a significant $P_{50}$ shift. FIG. 2 illustrates the individual differences in the $P_{50}$ shift induced in the mice by ingestion of the aqueous solution of kf111.

XVI. Blood Counts of kf111-Treated and Control Mice

Blood from mice, having ingested kf111 or IHP in water (for 4 days) or water only was collected on day 0, 7 and 11, in order to assess any differences in the blood count (and the amount of erythropoietin in the sera) of treated and control mice. Two major observations were made: 1.) The number of RBC in mice having ingested kf111 was reduced significantly, and 2.) There were no major differences in the number of white blood cells (e.g. granulocytes, macrophages ect.) in blood from mice in different groups. Table 1 shows the RBC counts for mice with shifted ODC as compared to controls. Erythropoietin assays in all mice sera will be reported soon.

TABLE 5

Number of RBC and $P_{50}$ shifts of treated and control animals determined on days 7 and 10 of the experiment

| kf111 | Δ $P_{50}$ 7 d % | RBC × $10^6$/mm3 | Δ $P_{50}$ 10 d % | RBC × $10^6$/mm3 |
|---|---|---|---|---|
| Mouse 1 | 7 | 7.70 | 8 | 8.73 |
| Mouse 3 | 16 | 6.54 | 11 | 7.65 |
| Mouse 4 | 9 | 6.54 | 9 | 7.80 |
| Mouse 5 | 13 | 6.60 | 10 | 9.35 |
| Mouse 6 | 14 | 5.73 | 6 | 8.60 |
| Mouse 7 | 20 | 6.35 | 10 | 8.95 |
| Mouse 8 | 16 | 5.64 | 12 | 8.88 |
| Mouse 11 | 15 | 5.45 | 10 | 8.95 |
| Mouse 12 | 20 | 8.76 | 16 | 8.70 |
| Water | 7 | 9.18 | 12 | 11.35 |
| Water | 4 | 8.7 | 1 | 10.95 |
| IHP | 3 | 9.6 | 0 | 10.77 |

Values of 9 mice having received kf111, and 2 mice having received water only and 1 mouse having received IHP/water are shown. The amount of blood from the other mice were not sufficient to determine the blood count. (On day 0 the RBC count in the mice was 8.9-11.8×$10^6$ cells/mm³).

Based on this data the following remarks can be made.
1.) kf111, when orally administered at a concentration of 27 mM, causes a significant right shift of the $P_{50}$ value in murine circulating RBC. There is a time lag of about 48 hrs before the maximum shift is attained, contrarily to the observations made after ip inoculation of kf111, where the $P_{50}$ shifts appears 2 hrs after inoculation.
2.) Maximal $P_{50}$ shifts are reached between day 2 and day 4 after beginning oral administration of kf111.
3.) After 12 days $P_{50}$ values are back to control values (taken on day 0), when ingestion is stopped on day 4.
4.) There is a significant effect of kf111 ingestion on the number of RBC.
5.) The reason of this reduction has to be clarified: Hemolysis of the RBC may be ruled out, as lysis of RBC never occurred in vitro. The amount of erythropoietin in treated and control animals will be reported soon.

It appears, that orally administered kf111 is effective in shifting the ODC of circulating RBC in mice, even at modest concentrations of the compound (27 mM).

XVII. Intravenous Injection of kf111 in Normal Pigs

An in vivo-experiment was performed on one 8 week-old normal piglet (body weight: 17 kg). The piglet was anaesthesized with 5% Isoflurane, 0.7 L/min $N_2O$ and 2.0 L/min $O_2$ for 20-30 minutes, when kf111 was injected, or blood was taken from the ear vein, respectively. The compound injected iv at a concentration of 27 g kf111/100 ml water (volume injected: 63 ml, pH 6.5, containing 17 g kf111=1 g/1 kg body weight) was not harmful to the animal, when injected into the piglet's ear vein over at least 10 minutes. The $P_{50}$ values of the porcine blood obtained over 2 weeks after iv-injection are shown in FIG. 14.

XVIII. Blood Counts of the kf111 Treated Piglets

Blood from the 2 piglets, having received kf111 (1 g/kg body weight) was collected before injection, 2 hrs after, and daily over a period of 14 days after injection, in order to assess any differences in the blood counts of treated and non treated piglets. The following conclusions for piglets having received 1 g kf111 per kg body weight can be drawn:

1. A slight decrease in hematocrit and in the number of RBC was observed in the first days after injection.
2. A tendency towards the decrease of the reticulocytes (from 1.4% to 0.5%) was observed in blood samples collected the first 3 days after injection.
3. Increasing numbers of reticulocytes were counted in blood samples of the injected animals taken 5-14 days after injection (up to 3.0% on day 14).
4. Again, no major differences in the number of other cells, such as white blood cells (e.g. granulocytes, macrophages, platelets ect.) were detected.

XIX. Dosis Effect Curve

Iv injection of 1 g kf111/kg body weight caused a significant right shift of the $P_{50}$-value (up to 20%) in porcine RBCs. An almost saturated kf111 solution, pH 6.7, was injected intravenously into two piglets (both of ~18 kg body weight) (27 g kf111/100 ml=1.5 g/kg body weight) over 20 minutes.

Both piglets died, before the injection was completed (at that time point the animals had received<1.3 g/kg body weight=70-80 ml of the saturated kf111-solution).

Figure 15:
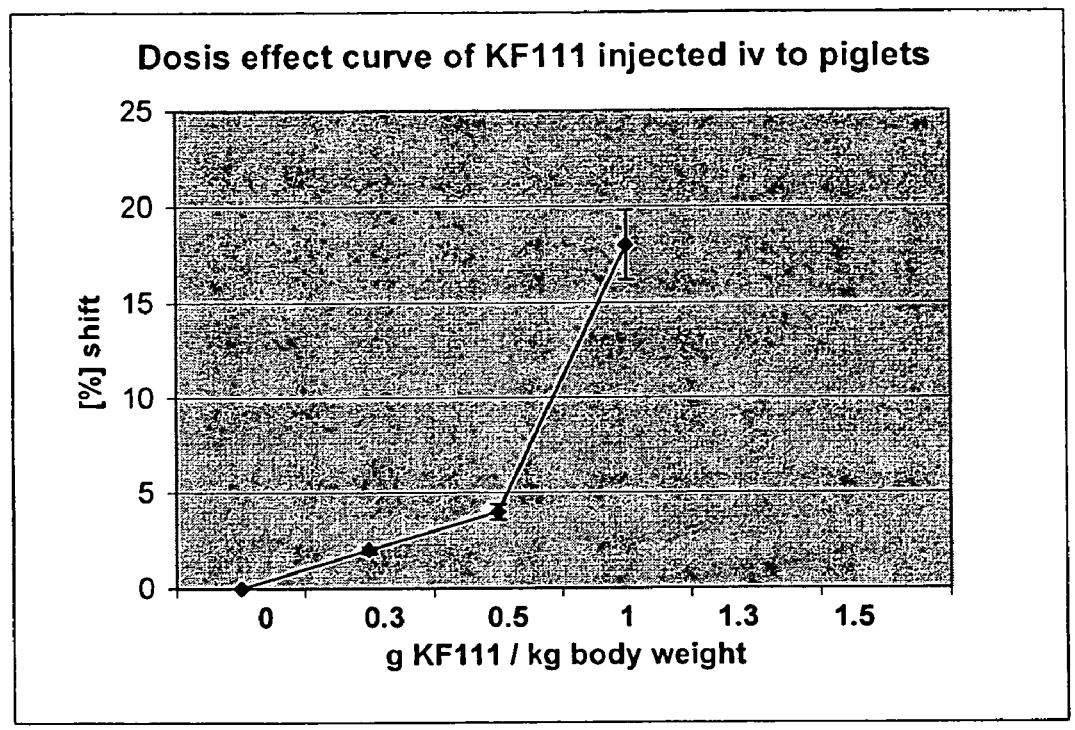
FIG. 15 depicts the dosis curve for 3 piglets injected via iv with 0.3, 0.5, 1*, 1.3 and 1.5 g kf111 per kg body weight. Means of 4 single $P_{50}$ values per blood sample and standard deviation are given. (*2 piglets injected).

Blood was taken from the heart of the dead animals for the determination of blood counts as well as the amount of sodium, potassium and calcium in the sera. All numbers of blood cells (hematocrit, white blood cells ect.) were halved. The amount of potassium and calcium was normal, while sodium was doubled (before injection: 120-140 mmol/L; after injection: 245 mmol/L). Apparently, the large amount of sodium in kf111 (6 $Na^+$/molecule) caused the death of the animals. It appears that up to 1 g kf111 per kg body weight can be injected iv, (if injected slowly) without harmful effects for the animals. The dosis effect curve is shown in FIG. 15. The following conclusions can be drawn from these results:

1. kf111 was not harmful to the piglet, when applied intravenously slowly (at least 10 min for a vol. of solution of 100 ml)) at a concentration≦1 g/kg*body weight. The piglets were thirsty after the treatment.
2. Higher amounts of kf111, injected via iv, killed the animals.
3. A 1 g kf111 per kg body weight-injection is necessary to cause a significant right shift of the $P_{50}$ value (up to 20%).
4. Pigs having received this amount of kf111, at that concentration, did not show any pathological changes of the blood counts, when injected slowly.
5. In piglets having received 1 g of kf111/kg body weight, a tendency to the decrease in hematocrit was observed.
6. No major differences in the number of white blood cells (e.g. granulocytes, macrophages, platelets ect.) in blood from the treated piglets were detectable.
7. The number of reticulocytes decreased slightly 24 to 72 hrs after injection (from 1.5% to 0.5%). Starting with day 3 after injection of the allosteric effector, the number of reticulocytes increased by about 3% for a period of 14 days.
a second piglets was injected with kf111 at this concentration, after 2 piglets had died after iv injection of 1.2 g kf111 (or even more) per kg body weight.

EXEMPLIFICATION

Preparation of Effectors

The different synthetic pathways followed during our studies on IHP molecules are briefly described in the general scheme for the synthesis of IHP derivatives. See FIG. 10.

Starting from Compound A, Route 1, upon reaction with excess of acyl anhydrides $(RCO)_2O$ (R=$CH_3$-kf12, kf20, $C_2H_5$-kf47, $C_3H_7$-kf43, $C_4H_9$-kf40, $C_5H_{11}$-kf46, $C_6H_{13}$-kf28, $C_6H_5$-kf13, kf22, $CH_2$=$C(CH_3)$-kf34 in $CH_3CN$ reflux (see experimental section at the end of this review) we were targeting a fully substituted hexa-acylated IHP that was thought to increase the lipophilicity of IHP by decreasing its charges by 6. The chemical shift of the phosphorous were resonated around 10 ppm higher field than the starting material. This fact was thought due to the shielding effect of the carboxylic substituent. However, instead of the expected products, and despite the fact that acyl anhydrides were described as stable compounds in acidic to neutral pH and under elevated temperatures, another product was formed through dehydration of IHP. This product proved to be Compound B, the tripyrophosphate of IHP (ITPP), which has also 6 charges less than the starting material.

The same Compound B can be synthesized from Compound C, phytic acid, Route 2, upon reaction with DCC. Route 2, was described in the literature—the products of Route 1 and 2 were found identical—and it was thought more preferable for the synthesis of tripyrophosphates (than the one with the acyl anhydrides) due to the inexpense of the reagents (see experimental section). Furthermore, starting from the pyridinium salt of ITPP that can be synthesized in large quantities and in a clean form, we developed a methodology to exchange the counter cations and create libraries of ITPP ionically bound to lipophilic ammoniums (see exp. sect.). These salts exhibited interesting physicochemical and biological properties. Especially the Na ITPP salt kf111 was the molecule with the best profile, showing no toxicity even in a concentration of 160 mM. The activity of the ITPP molecules was predicted from the discovery of the fate of the cholesteryloxy carbonyl derivative in aqueous solutions, Route 3.

Reaction of Compound A, Route 3, with CholCOCl, (see experimental section) gave the Cholesteryloxy carbonyl derivative-kf16, kf38, kf42, kf96, which was stable only in some organic solvents, and for limited period of time. Addition of water caused extensive hydrolysis back to the starting material, as well as the formation of a new compound, IHP-monopyrophosphate ("IMPP"), Compound D. IMPP was also formed after prolonged reaction times of compound A with CholCOCl in $CH_2Cl_2$. Therefore, all reactions made using the early procedures contained an abundant amount of IMPP. The remaining of the Chol derivative was converted to IMPP after addition of water-necessary for the biological experiments-. The same Compound D can be synthesized upon reaction of Compound A, with 1 equiv DCC, Route 4 (see exp. sect., kf109). This Route was also found more preferable due to the inexpense of the reagents and the stoichiometry of the reaction. Under DCC conditions only IMPP is formed and we run no risk of hydrolysis from water and formation of the starting material A, (like in the case of Chol derivative). Furthermore, IMPP D, can be synthesized either from A, or C-phytic acid-kf149. The exchange of the counter cations is at the same time possible and desired for the formation of more derivatives. The Na salt kf133, kf152 again was found non-toxic as compared with the N,N-DMCHA salt kf109.

The formation of the IMPP is not selective, due to the similar reactivity of all the phosphate moieties of IHP. Since all possible IHP monopyrophosphate isomers exist in the active pool of compounds, their combination literally led to the design of the tripyrophosphate of IHP B, as a more promising candidate. The molecule being an internal anhydride of IHP showed no toxicity and excellent tolerability in the in vivo biological experiments, especially with Na as counter cations, kf111. These compounds were easily synthesized as explained before using Route 2.

Finally, taking advantage of the best conditions found for the synthesis of the Chol derivative, we applied them on the synthesis of acyl derivatives of IHP, Route 5. Indeed reaction of 1-3 equiv of acyl anhydrides with Compound A gave (see exp. sect.) Compounds E in very good yields, R=$C_5H_{11}$-kf137, kf151, kf160, kf161. The latter products are relatively stable in water but with careful treatment we were able to perform extractions, and adjust their pH to 7. Furthermore we could change the counter cations to Na. Kf157-R=$C_5H_{11}$, kf158-R=$CH_3$, pH=7, kf137-R=$C_5H_{11}$, kf105-R=$C_6H_5$, upon heating in $CH_3CN$ gave Compound D via Route 6, providing more proof that indeed acyl phosphate mixed anhydrides have been formed.

Synthesis of tripyrophosphates from reactions with acyl-anhydrides. ROUTE 1

N,N-Dimethyl cyclohexyl ammonium Salt of Myo-inositol 1,6:2,3:4,5-Tripyrophosphate, Compound B IHP-octa-N,N-Dimethyl cyclohexyl ammonium salt A (1 equiv) was dissolved in $CH_3CN$ (0.02 mM) and acyl anhydride $(RCO)_2O$ (20-30 equiv) was added. The mixture was refluxed for 24 h. (R=$CH_3$-kf12, kf20, $C_2H_5$-kf47, $C_3H_7$-kf43, $C_4H_9$-kf40, $C_5H_{11}$-kf46, $C_6H_{13}$-kf28, $C_6H_5$-kf13, kf22, $CH_2$=$C(CH_3)$-kf34). (In case of R=$CH_3$ no solvent was use mixture was heated in neat acetic anhydride at 120° C. for 24 h). The reaction mixture was cooled at 0° C. and water and toluene was added and the mixture was extracted several times with toluene. The aqueous phase was concentrated to dryness, and the product was dried in vacuum to give N,N-Dimethyl cyclohexyl ammonium Salt of Myo-inositol 1,6:2,3:4,5-Tripyrophosphate.

Hexasodium Salt of Myoinositol 1,6:2,3:4,5-Tripyrophosphate, Compound B

The products of Route 1 were passing through an ion exchange Dowex 50W×8 $Na^+$ form column, and the elute was concentrated in vacuum to give hexasodium Salt of Myo-inositol 1,6:2,3:4,5-Tripyrophosphate.

Synthesis of tripyrophosphate kf111. ROUTE 2

Hexasodium Salt of Myo-inositol 1,6:2,3:4,5-Tripyrophosphate, Compound B

See *Can J. Chem.* 1969, 47, 63-73.

Crystalline sodium phytate C (4 g) was dissolved with sonication in water (20 ml) and converted to the free acid by passage through a column of Dowex 50×8-200 ion-exchange resign. The column eluate was adjusted to pH 8 with pyridine and evaporated to dryness. The residue was dissolved in water (30 ml) and pyridine (130 ml) containing N,N-dicyclohexylcarbodiimide (8 g) was added. The reaction mixture was heated to 65° C. for 18 h and evaporated to dryness. The residue was extracted with water (4×10 ml) filtered and the filtrate was evaporated to dryness to give the pentapyridinium Salt of Myo-inositol 1,6:2,3:4,5-Tripyrophosphate (3.355 g, 77% yield). $^{31}$P-NMR ($D_2O$) δ: −8.83 & −13.53 (AB, J=22.3 Hz, 2P, ax-eq), −9.82 & −10.00 (AB, J=17.8 Hz, 2P, eq-eq), −10.18 (AB as a singlet, 2P, eq-eq); $^1$H-NMR ($D_2O$) δ: 8.65 (d, J=5.6 Hz, 10H), 8.48 (dd, J=7.9, 7.9 Hz, 5H), 7.94 (dd, J=7.0, 7.0 Hz, 10H), 5.00 (bd, J=10.5 Hz, 1H), 4.57 (ddd, J=9.6, 9.6, 5.5 Hz, 1H), 4.43-4.36 (m, 2H), 4.30-4.18 (m, 2H); $^{13}$C-NMR ($D_2O$) δ: 147.0, 140.9, 127.3, 77.9 (t, J=6.8 Hz), 76.4-76.0 (m), 75.4-75.0 (m), 73.8 (t, J=6.8 Hz), 73.3 (bs), 72.8 (bs). The compound was then dissolved in water (30 ml) and passed through a column Dowex 50W×8 $Na^+$ form. The column eluate was concentrated to dryness to give Hexasodium Salt of Myo-inositol 1,6:2,3:4,5-Tripyrophosphate (2.25 g, 97%) and used for biological experiments in 98.5% purity without any further purification. The impurity is unreacted starting material (or tripyrophosphate hydrolyzed back to starting material). $^{31}$P-NMR ($D_2O$) δ: −8.34 & −13.14 (AB, J=21.7 Hz, 2P, ax-eq), −9.53 & −9.70 (AB, J=17.8 Hz, 2P, eq-eq), −9.92 (AB as a singlet, 2P, eq-eq); $^1$H-NMR ($D_2O$) δ: 5.04 (bd, J=10.5 Hz, 1H), 4.65-4.59 (m, 1H), 4.51-4.36 (m, 2H), 4.32-4.18 (m, 2H); $^{13}$C-NMR ($D_2O$) δ: 77.1-76.8 (m), 76.5-76.0 (m), 75.4-75.0 (m), 74.1-73.9 (m), 73.7-73.2 (m), 73.2-72.5 (m).

Synthesis of libraries of ammonium salts of tripyrophosphates. ROUTE 2

Ammonium Salts of Myoinositol 1,6:2,3:4,5-Tripyrophosphate, Compound B

The pentapyridinium Salt of Myo-inositol 1,6:2,3:4,5-Tripyrophosphate (the synthesis of which described before-literature procedure) converted to the free acid by passage through a column of Dowex 50×8-200 ion-exchange resign. The column eluate without any concentration was put in a round bottom flask and 6 equiv of the desired amine was added. The mixture was stirred at rt for 20 min and the mixture was evaporated to dryness to give ammonium Salts of Myo-inositol 1,6:2,3:4,5-Tripyrophosphate.

N,N-dimethyl cyclohexyl ammonium derivative $^{31}$P-NMR ($CDCl_3$) δ: −9.79 (AB as a singlet, 2P, eq-eq) −10.18 & −10.63 (AB, J=21.2 Hz, 2P, eq-eq), −10.63 & −12.66 (AB, J=25.6 Hz, 2P, ax-eq); $^1$H-NMR ($CDCl_3$) δ: 5.42 (d, J=11.2 Hz, 1H), 4.76-4.67 (m, 1H), 4.59 (ddd, J=9.9, 9.9, 5.4 Hz, 1H), 4.36 (bdd, J=8.3, 8.3 Hz, 1H), 4.31-4.21 (m, 1H), 4.05 (dd, J=9.5, 2.8 Hz, 1H), 2.95 (bs, 6H), 2.77 (s, 6×3×2 H), 2.04 (bs, 12H), 1.82 (bs, 12H), 1.60 (d, J=12.3 Hz, 6H), 1.28 (bs, 24H), 1.04 (bs, 6H); $^{13}$C-NMR ($CDCl_3$) δ: 75.2-74.9 (m), 74.2-73.7 (m), 72.8-72.3 (m), 64.6, 39.4, 26.3, 25.0, 24.7.

$^{31}$P-NMR ($D_2O$) δ: −8.76 & −13.48 (AB, J=23.4 Hz, 2P, ax-eq), −9.82 (AB as a singlet, 2P, eq-eq), −10.09 (AB as a singlet, 2P, eq-eq); $^1$H-NMR ($D_2O$) δ: 5.04 (d, J=10.7 Hz, 1H), 4.57-4.46 (m, 1H), 4.45-4.32 (m, 2H), 4.31-4.12 (m, 2H), 3.05 (bt, J=11.3 Hz, 6H), 2.69 (s, 36H), 1.90 (d, J=10.0 Hz, 12H), 1.77 (d, J=12.6 Hz, 12H), 1.54 (d, J=12.7 Hz, 6H), 1.42-0.91 (m, 30H)

Cycloheptyl Ammonium Salt $^{31}$P-NMR (D$_2$O) δ: −8.61 & −13.37 (AB, J=23.4 Hz, 2P, ax-eq), −9.72 & −9.76 (AB, J=19.5 Hz, 2P, eq-eq), −10.02 (AB as a singlet, 2P, eq-eq); $^1$H-NMR (D$_2$O) δ: 5.02 (bd, J=10.4 Hz, 1H), 4.60-4.49 (m, 1H), 4.45-4.32 (m, 2H), 4.30-4.18 (m, 2H), 3.31-3.28 (m, 6H), 1.97-1.82 (m, 12H), 1.70-1.25 (m, 60); $^{13}$C-NMR (D$_2$O) δ: 52.6, 32.29, 27.14, 23.14.

Cyclooctyl Ammonium Salt $^{31}$P-NMR (D$_2$O) δ: −8.62 & −13.38 (AB, J=23.4 Hz, 2P, ax-eq), −9.72 & −9.76 (AB, J=17.8 Hz, 2P, eq-eq), −10.03 (AB as a singlet, 2P, eq-eq); $^1$H-NMR (D$_2$O) δ: 5.02 (bd, J=10.6 Hz, 1H), 4.60-4.48 (m, 1H), 4.46-4.35 (m, 2H), 4.32-4.15 (m, 2H), 3.40-3.32 (m, 6H), 1.90-1.20 (m, 84H); $^{13}$C-NMR (D$_2$O) δ: 51.8, 30.2, 25.9, 24.96, 22.87.

Synthesis of the IHP cholesteryoxy carbonyl hepta N,N-Dimethyl cyclohexyl ammonium salt. ROUTE 3

IHP cholesteryoxy carbonyl hepta N,N-Dimethyl cyclohexyl ammonium salt

Initial conditions: material contaminated with monopyrophosphates, kf16, kf38, kf42, kf96.

IHP-octa-N,N-Dimethyl cyclohexyl ammonium salt A (3.094 g, 1.8506 mmol, 1 equiv) was dissolved in CH$_2$Cl$_2$ (76 ml) and 1,4 dioxane (30 ml), and CholCOCl (873 mg, 1.94313 mmol, 1.05 equiv) was added in one portion. The mixture was stirred at rt under argon for 5 days, and concentrated to dryness. For the purification of 1.5 g of crude material approximately 1.5 lt of hex and hex/CH$_2$Cl$_2$ 9/1 were used as follows: The solid was washed with the solvents and the supertants were removed. The remaining solid was again washed, until no cholesterol was observed by TLC.

kf96 $^{31}$P-NMR (CDCl$_3$) δ: 3.00--2.5 (m, global integration 5P), −5.55--6.7 & −7.8--9.6 & −10.2--12.1 & −13.5--14.8 (multiplets, global integration 1P); $^1$H-NMR (CDCl$_3$) δ: 4.90-0.10 (multiplets).

$^{31}$P-NMR (D$_2$O) at pH=7 δ: 4.07, 3.64, 3.49, 2.97, 2.85, 2.61, 2.48, 2.37, 1.90 (all singlets, global integration 5P), −7.80--8.45 (3 doublets, J=23.4, 22.3, 23.4 Hz), −8.74--10.03 (singlets and doublets, J=16.7, 16.7, 17.8 Hz), −12.53 (d, J=23.4 Hz), −13.01 (d, J=22.2 Hz); $^1$H-NMR (D$_2$O) δ: 4.5-3.5 (multiplets), 3.1-1.0 (peaks corresponding to N,N-DMCHA salt.

Improved conditions: material not contaminated with monopyrophosphates, kf92.

IHP-octa-N,N-Dimethyl cyclohexyl ammonium salt A (400 mg, 0.24 mmol, 1 equiv) was dissolved in CH$_3$CN (5 ml) and THF (5 ml), and CholCOCl (161 mg, 0.36 mmol, 1.5 equiv) was added in one portion. The mixture was stirred at rt under argon for 24 h and concentrated to dryness. For the purification of the crude material approximately 1 lt of hex/THF 9/1 were used. The solid was washed with the solvents, centrifuged and the supertants were removed. The remaining solid was again washed, until no cholesterol was observed by TLC.

kf92 $^{31}$P-NMR (CDCl$_3$) δ: 1.76 & −0.03 (2 broad multiplets as singlets, global integration 5P), −6.53 (bs, 1P); $^1$H-NMR (CDCl$_3$) δ: 5.31 (bs), 4.90-4.15 (m), 3.71 (bs) 3.03 (bs), 2.79 (bs), 2.4-0.5 (m).

$^{31}$P-NMR (D$_2$O) δ: 2.12-0.05 (many singlets), −8.84 (d, J=21.5 Hz), 9.46 (d, J=17.8 Hz), −9.80--10.00 (m), −13.18 (d, J=17.8 Hz); $^1$H-NMR (D$_2$O) δ: 4.90-4.73 (m, 2H), 4.49-4.38 (m), 4.30-4.20 (m), 3.06 (bs, 6H), 2.69 (s, 36H), 1.83 (bs, 12H), 1.76 (bs, 12H), 1.54 (d, J=11.9 Hz, 6H), 1.36-1.00 (m, 30H).

When the compound was dissolved in water, monopyrophosphate was formed in all cases.

Synthesis of the IHP monopyrophosphate. ROUTE 4

IHP monopyrophosphate N,N-Dimethyl cyclohexyl ammonium salt, Compound D

Procedure No. 1 from IHP-octa-N,N-Dimethyl cyclohexyl ammonium salt, reaction kf109.

IHP-octa-N,N-Dimethyl cyclohexyl ammonium salt A (1.175 g, 0.7 mmol, 1 equiv) was dissolved in CH$_3$CN (20 ml) and H$_2$O (10 ml), and DCC (146.5 mg, 0.7 mmol, 1. equiv) was added in one portion. The mixture was refluxed overnight, cooled to rt, the solid was filtrated and the filtrate was concentrated to dryness. The residue was dissolved in water and filtrated again. The filtrate was concentrated to dryness to give IHP monopyrophosphate N,N-Dimethyl cyclohexyl ammonium salt.

$^{31}$P-NMR (CDCl$_3$) δ: 2.9--1.0 (many singlets, global integration 5P), −8.50--10.9 (m, 1.4H doublets present with J=24.5, 16.7 Hz), −12.90--13.7 (m, a main doublet J=22.8 Hz, 0.2P); $^1$H-NMR (CDCl$_3$) δ: 5.5-3.0 (bm), 2.87 (bs, 6H), 2.71 (bs, 36H), 2.02 (s, 12H), 1.76 (s, 12H), 1.56 (d, J=12.1 Hz, 6H), 1.24 (bs, 24H), 1.04 (bs, 6H).

IHP monopyrophosphate pyridinium salt, Compound D

Procedure No. 2 from IHP-dodecasodium salt, based on *Can. J. Chem.* 1969, 47, 63-73, reaction kf149.

Crystalline sodium phytate C (2 g) was dissolved with sonication in water (10 ml) and converted to the free acid by passage through a column of Dowex 50×8-200 ion-exchange resign. The column eluate was adjusted to pH 8 with pyridine and evaporated to dryness. The residue was dissolved in water (14 ml) and pyridine (56 ml) containing N,N-dicyclohexyl-carbodiimide (438 mg, 1 equiv) was added. The reaction mixture was heated to 65° C. for 18 h and evaporated to dryness. The residue was extracted with water (4×10 ml) filtered and the filtrate was evaporated to dryness to give the IHP monopyrophosphate pyridinium salt.

$^{31}$P-NMR (D$_2$O) δ: 2.05--0.02 (singlets), −8.95 (d, J=21.9 Hz), −9.42--10.21 (m), −13.25 (d, J=22.3 Hz); $^1$H-NMR (D$_2$O) δ: 8.60 (d, J=5.3 Hz), 8.43 (dd, J=8.0, 8.0 Hz), 7.89 (dd, J=6.9, 6.9 Hz), 5.04 (d, J=10.4 Hz), 4.79 (d, J=11.7 Hz), 4.38-4.22 (m), 4.20-4.02 (m).

IHP monopyrophosphate sodium salt, Compound D

Compound kf109 or kf149 was dissolved in water and passed through a column Dowex 50W×8 Na$^+$ form. The column eluate was concentrated to dryness to give IHP monopyrophosphate hexasodium salt, kf133, kf152, respectively.

$^{31}$P-NMR (D$_2$O) δ: 2.26-0.42 (many singlets, 5P), −8.34 & −12.89 (AB doublet, J=22.6 Hz, 0.5P), −9.00--9.98 (m, 1.2P); $^1$H-NMR (D$_2$O) δ: 5.10 (bd, J=10.4 Hz), 4.80 (bd, J=9.9 Hz), 4.55-4.32 (m), 4.25-4.09 (m).

Synthesis of the IHP acyl compounds. ROUTE 5

IHP acyl N,N-Dimethyl cyclohexyl ammonium salt, Compound E

IHP-octa-N,N-Dimethyl cyclohexyl ammonium salt A (1 equiv) was dissolved in CH$_3$CN or CH$_3$CN/THF and (RCO)$_2$O (1-3 equiv) was added in one portion, (R=CH$_3$- kf158, $C_5H_{11}$-kf137, kf151, kf160, kf161, R=$C_6H_5$-kf105). The mixture was stirred at rt for 24 h and concentrated to dryness. Water and toluene (both ice cold) were added and the mixture was extracted several times with toluene. The aqueous phase was centrifuged to remove as much toluene as possible, and cooled to 0° C. Ice cold NaOH 0.2M was added dropwise until pH 7. The sample then was lyophilized to give IHP acyl N,N-Dimethyl cyclohexyl ammonium salt.

Samples heated in $CH_3CN$ gave monopyrophosphate
ROUTE 6 kf 159 Benzoyl-IHP Na salt $^{31}$P-NMR ($CDCl_3$) crude δ: 2.88-0.10 (many singlets), -5.09 (main singlet) ratio 7.5:1 kf 137 Hexanoy-IHP N,N-DMCHA salt $^{31}$P-NMR ($CDCl_3$) pH=7 δ: 2.96-0.48 (many singlets), -4.96 & -5.65 & -8.04 (main singlets), -5.00--7.81 (other smaller singlets) total integration ratio 5non acylated:1; $^1$H-NMR ($CDCl_3$) δ: 5.01-4.25 (3 multiplets, 6H), 2.87 (bs), 2.72 (s), 2.6-2.2 (m), 2.07 (bs), 1.84 (bs), 1.68-1.62 (m), 1.40-1.10 (m) 0.86 (m as a d); $^{13}$C-NMR ($CDCl_3$) δ: 171.2-169.8 (m).

kf158a Acetyl-IHP N,N-DMCHA salt $^{31}$P-NMR ($CDCl_3$) crude δ: 2.90--0.14 (many singlets), -5.63--8.90 (many singlets) ratio 2:1.

IHP acyl sodium salt, Compound E (Procedure like before until centrifugion). The aqueous phase was then passed through a column Dowex 50W×8 $Na^+$ form. The column eluate was cooled to 0° C. Ice cold NaOH 0.2M was added dropwise until pH 7. The sample then was lyophilized to give IHP acyl sodium salt. (R=$CH_3$-kf158, $C_5H_{11}$-kf157).

kf 157 Hexanoy-IHP Na salt $^{31}$P-NMR ($D_2O$) pH=7 δ: 3.81-0.08 (many singlets, 4.6P), -6.46 (main singlet), -5.84--7.32 (other smaller singlets) global integration 1, and 5% hydrolysed to pyrophosphate; $^1$H-NMR ($D_2O$) δ: 4.92-4.80 (m), 4.38-4.25 (m), 4.17-4.01 (m), 3.51 (q, J=7.1 Hz), 2.40 (bt, J=7.5 Hz), 2.03 (t, J=7.5 Hz), 1.58-1.35 (m), 1.30-1.11 (m, 2H), 1.04 (t, J=6.9 Hz, 5H), 0.75 (bs, 3H); $^{13}$C-NMR ($CDCl_3$) δ: 173.15 (dd as a t, J=9.4 Hz), 77.3 (m), 76.2 (m), 75.0 (m), 73.9 (m), 73.4 (m), 57.4, 37.4, 34.7 (3 peaks), 30.9, 30.4 (2 peaks), 25.4, 23.5, 21.7 (2 peaks), 16.7, 13.2 (after one month in the freezer some hydrolysis has occurred).

kf 158 Acetyl-IHP Na salt $^{31}$P-NMR ($D_2O$) pH=7 δ: 3.60-1.18 (many singlets), -613--7.90 (many singlets, main singlet -6.97), 18% hydrolysed to pyrophosphate; $^{13}$C-NMR ($D_2O$) δ: 170.86-170.45 (m).

EXPERIMENTS

A. In Vitro Experiments Performed with Whole Blood from Human, Mouse and Pig

The effectors kf96 and kf111 (60 mM) were tested for $P_{50}$ shifts in whole blood of three species: human, mouse and pig.

As usual, pH's for the compound-solutions were adjusted to ~7.0, osmolarities for both solutions were determined (325-373 mOsM) prior to effectors, and whole blood volumes at 1:1 ratios were incubated. Following incubation, blood cells were washed 3 times with Bis-Tris-buffer (no lysis of RBCs was observed). A summary of $P_{50}$ values for whole blood induced by the effectors is presented in Table 5.

TABLE 5

$P_{50}$ values in whole blood after incubation with effectors kf96 and kf92p in vitro*.

| Blood | $P_{50}$ mm Hg CONTROL | $P_{50}$ mm Hg effector kf96 | $P_{50}$ Increase % | $P_{50}$ mm Hg effector kf111 | $P_{50}$ Increase % |
|---|---|---|---|---|---|
| Human | 22.1 | 28 | 27 | 30.8 | 39 |
| Pig | 32.2 | 41.1 | 27 | 45.2 | 40 |
| Mouse | 36.7 | 43.9 | 20 | 47.4 | 29 |

*only one animal (human) for each substance.

In all blood samples a strong right shift in the Hb-$O_2$ dissociation curve was observed. The shifts obtained with kf111 (up to 40%) were even stronger than with kf96 (27%). This and the fact that kf111 is well tolerated by mice even at a concentration of 120 mM led to a study where several concentrations of kf111 (30 mM-150 mM) were injected intraperitoneally to a group of 10 C57Bl/6-mice for each concentration. At the present time we are performing this study by taking blood samples from injected mice at 2 hours, 1 day, 4 days, and 12 days after injection, in order to measure $P_{50}$ shifts in blood and to follow the decrease of $P_{50}$-shifts over time.

The concentration of the electrolytes sodium, potassium and calcium will be determined after injection, in order to investigate possible side effects.

B. Investigation of the Effects of Intraperitoneal Injections of the Effector kf111

Blood from C57Bl/6 mice collected 2 hrs and 1 day after injection of 45, 60, 120 and 150 mM solutions of kf111 was measured for $P_{50}$-shifts as reported. $P_{50}$-values of each single sample are listed in Table 6. Effector kf111 was well tolerated even at concentrations of 150 mM. No animal died or seemed to suffer from the compound. There was a shift of $P_{50}$ at all concentrations.

TABLE 6

$P_{50}$ values of circulating RBC after ip-injection of the effector kf111.

| Effector Concentration kf111 | $P_{50}$ Shift % 2 h | Mean +/- SD* | $P_{50}$ Shift % 24 h | Mean +/- SD* |
|---|---|---|---|---|
| 45 mM | 12 | 11.8 +/- 1.16 | 13 | 13.6 +/- 1.02 |
| | 11 | | 15 | |
| | 13 | | 14 | |
| | 10 | | 12 | |
| | 13 | | 14 | |
| 60 mM | 12 | 16.9 +/- 3.48 | 14 | 17.2 +/- 2.1 |
| | 14 | | 16 | |
| | 17 | | 17 | |
| | 21 | | 20 | |
| | 20.5 | | 19 | |
| 120 mM | 28 | 26.0 +/- 2.28 | 28 | 24.8 +/- 2.7 |
| | 29 | | 28 | |
| | 24 | | 22 | |

TABLE 6-continued

P$_{50}$ values of circulating RBC after
ip-injection of the effector kf111.

| Effector Concentration kf111 | P$_{50}$ Shift % 2 h | Mean +/− SD* | P$_{50}$ Shift % 24 h | Mean +/− SD* |
|---|---|---|---|---|
| 150 mM | 26 | | 24 | |
| | 23 | | 22 | |
| | 26 | 27.0 +/− 1.78 | 25 | 25.8 +/− 2.78 |
| | 28 | | 26 | |
| | 30 | | 31 | |
| | 26 | | 24 | |
| | 25 | | 23 | |

P$_{50}$ values of blood from 5 animals each are listed;
*SD = standard deviation.

C. In Vitro Experiments with Effectors kf133 and kf137 Performed with Pig Hemoglobin and Whole Blood Two further effectors, kf133 and kf137, were tested in vitro for P$_{50}$ shifts with porcine hemoglobin and whole blood. The compounds were well soluble. As usual, pH was adjusted to ~7.0 and effector solution (2.5 mM) and hemoglobin (2.5 mM) were mixed at a 1:1 ratio. Whole blood and the effector solution were mixed at iso-osmolarity at pH=7. P$_{50}$ values were measured as described in the previous experiments. A summary of P$_{50}$ values of free hemoglobin and whole blood induced by kf133 and kf137 effectors is presented in Table 7.

TABLE 7

P$_{50}$ values of porcine free hemoglobin and whole blood after incubation with the effectors kf133 and kf137 in vitro.

| Effector Name | P$_{50}$ Mm Hg Control hemoglobin | P$_{50}$ mm Hg | P$_{50}$ Increase % | P$_{50}$ mm Hg Control whole blood | P$_{50}$ mm Hg | P$_{50}$ Increase % |
|---|---|---|---|---|---|---|
| kf133 | 20.4 19.9 | 48.5 | 143 | 33.5 | 38.4 | 14.5 |
| kf137 | 20.4 19.9 | 45.1 | 120 | 33.5 | 51.5 | 53.5 |

The following remarks can be made regarding these measurements:

1. Both compounds caused a significant right shift with porcine hemoglobin and whole blood. kf133 induced a P$_{50}$ shift of 143% with hemoglobin.

2. Whole blood incubated with kf133 gave a right shift of 14.5%.

3. The new compound kf137 showed a right shift of 120% with free porcine hemoglobin and surprisingly a very strong right shift with porcine whole blood (of 53% and more) under approximately iso osmolar conditions (288 mOsM).

4. Noticeable lysis of the RBC was observed with effector kf137.

D. Investigation of the Effects of Intraperitonel Injection of the Effectors kf133 and kf137

In order to evaluate the tolerability of the compounds kf133 and kf137, both were injected ip into C57Bl/6 mice as described before. Again, the pH was adjusted to 6.8-7.2, and 200 µl of the solutions were administered ip. Intraperitoneal injection was well tolerated by mice at a concentration of up to 120 mM. P$_{50}$-shifts of circulating RBC were up 20%.

Biological Evaluation

The biological evaluation of the effectors of Tables 1-4 are based in part on results reported in U.S. provisional application 60/376,383, incorporated herein in its entirety by reference.

Effectors kf16.3, kf16.4, kf96, kf92p, and kf93p were shown to cause a right shift in the P$_{50}$ value of both, free hemoglobin and whole blood. The percentage of P$_{50}$ increase in hemoglobin was up to 225%, in whole blood was up to 48%.

In vivo administration of 200 µl of a 45 mM of kf16.3 solution showed a right shift of the whole circulating blood of the injected mice, shifts being up to 22% (demonstrating on 2 animals).

Administration of the kf16.4 compound ip showed a significant right shift in the P$_{50}$ of up to 18%, demonstrated on 6 animals).

The tolerability of the compound was tested by direct injection into the vein at 30 and 45 mM: kf16 was non-toxic at these concentrations.

The tolerability of the compound was tested also by intraperitoneal injection at 30, 45 and 60 mM. kf16 was non toxic at these 3 concentrations.

A significant right shift in the Hb-O$_2$ dissociation curve is observed in vivo upon IP injection of the highly purified kf16.5 compound. This shift is concentration dependent. The injection of 200 µl of a 30 mM-kf96 caused a shift of up to 17%, a 45 mM-solution a shift up to 22%, and a 60 mM-solution a shift up to 24%.

The decrease of the P$_{50}$ shift over time is progressive and correlates with the life-time of the mouse RBC. This indicates that we have a true shift, induced by the allosteric effector injected.

Significant right shifts of the ODC of circulating RBC could be obtained in vivo also with IHP-pyrophosphates, mainly using IHP-tris-pyrophosphates.

The shifts amounted to 24% of the basal value, either when incubated with RBC in vitro or after intraperitoneal injection.

When injected to a limited number of animals, "cholesterol" derivatives were toxic at concentrations of 45 mM or upwards, whereas tripyrophosphates appear to be non toxic at much higher concentrations (60-120 mM).

Significant right shifts, 31% of the basal value after ip injection, of the ODC of circulating RBC could be obtained in vivo with effector kf111.

When injected up to 150 mM to a limited number of mice, effector kf111 was well tolerated.

Effectors kf111 and kf96 were tested with human and porcine blood: strong right shifts (up to 40%) were observed with effector kf111 in blood of all three species.

The newly synthesized allosteric effector kf137 was tested in vitro with porcine blood. A greater than 50% increase of the P$_{50}$ value was measured, which is the strongest shift in whole blood we ever observed in vitro with any IHP-derivative. As soon as sufficient amounts of purified effector is available, experiments will be conducted with murine, human, porcine, and canine blood in vitro.

CONCLUSION

Inositol pyrophosphates represent a new class of allosteric effectors of hemoglobin. Their highly charged nature allows them to pass through erythrocyte membranes and bind to hemoglobin, resulting in a significant right $P_{50}$ value. The progressive decrease of the $P_{50}$ shift over time correlates with the life time of mouse red blood cells. This indicates a true shift, induced by the inositol pyrophosphate allosteric effector. It is envisioned by the present invention that further derivatization of ITPP, IMPP, or the synthesis of more pyrophosphate containing compounds may lead to other allosteric effectors. The understanding of the mechanism of the transportation of these IHP compounds throughout membranes is also expected to lead to compounds with interesting properties.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are encompassed by the following claims.

We claim:

1. A method of treating hypoxia or ischemia in a patient by exposing the red blood cells of the patient in need of treatment for ischemia with an effective amount of a composition comprising a compound represented by structure I:

$nC^+A^{n-}$ wherein:
  $C^+$ represents independently for each occurrence an aliphatic ammonium cation, an alkali metal cation, an alkaline earth cation, or other suitable metal cation; and
  $A^{n-}$ represents an inositol hexaphosphate comprising 1, 2, or 3 internal pyrophosphate rings or an acyl group; and
  n is an integer in the range of 1 to 10 inclusive: and wherein the compound can passively cross the red blood cell membrane and cause a reduction of the oxygen affinity of hemoglobin.

2. The method of claim 1, wherein the red blood cells are exposed to the effective amount of the composition in vitro.

3. The method of claim 1, wherein the red blood cells are exposed to the effective amount of the composition in vivo.

4. The method of claim 1 wherein the inositol hexaphosphate comprises two internal pyrophosphate rings.

5. The method of claim 4 wherein the inositol hexaphosphate comprises three internal pyrophosphate rings.

6. The method of claim 1, wherein the aliphatic ammonium cation is a lipophilic, water-soluble aliphatic ammonium cation.

7. The method of claim 1, wherein the aliphatic ammonium cation is a monoalkyl, dialkyl, trialkyl, or tetralkyl ammonium moiety.

8. The method of claim 1, wherein the aliphatic ammonium cation is an N,N-dimethylcyclohexylammonium cation.

9. The method of claim 1, wherein the aliphatic ammonium cation is a monoalkyl ammonium cation.

10. The method of claim 1, wherein the aliphatic ammonium cation is a primary ammonium cation.

11. The method of claim 1, wherein A is represented by the compound of Formula II,

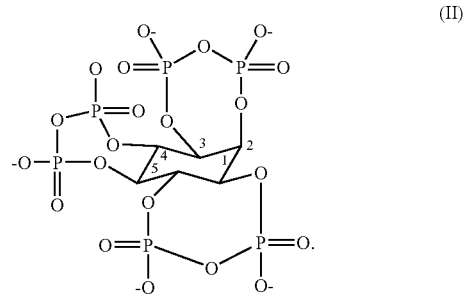

12. The method of claim 11, wherein C is sodium and n is 6.

13. The method of claim 3, wherein the composition is administered orally.

* * * * *